United States Patent [19]

Matzuk

[11] 3,964,296

[45] June 22, 1976

[54] INTEGRATED ULTRASONIC SCANNING APPARATUS

[76] Inventor: Terrance Matzuk, 154 Eileen Drive, Pittsburgh, Pa. 15214

[22] Filed: June 3, 1975

[21] Appl. No.: 583,242

[52] U.S. Cl. .......................... 73/67.5 R; 73/67.8 S; 73/67.9; 128/2 V
[51] Int. Cl.² ................... A61B 10/00; G01N 29/04
[58] Field of Search ........... 73/67.5 R, 67.5 H, 67.6, 73/67.7, 67.8 R, 67.8 S, 67.9, 71.5 US; 128/2 V

[56] References Cited
UNITED STATES PATENTS

| | | | |
|---|---|---|---|
| 3,023,611 | 3/1962 | Howry | 73/67.8 S |
| 3,415,111 | 12/1968 | Chattaway et al. | 73/71.5 US |
| 3,480,002 | 11/1969 | Flaherty et al. | 128/2 |
| 3,780,572 | 12/1973 | Rocha | 73/67.5 R |
| 3,817,089 | 6/1974 | Eggleton et al. | 73/67.8 S |

FOREIGN PATENTS OR APPLICATIONS

| | | | |
|---|---|---|---|
| 865,573 | 4/1961 | United Kingdom | 73/67.8 S |

*Primary Examiner*—Richard C. Queisser
*Assistant Examiner*—John P. Beauchamp
*Attorney, Agent, or Firm*—Arnold B. Silverman

[57] ABSTRACT

An integrated closed ultrasonic scanner having a sealed housing provided with an acoustically conductive liquid disposed therein. Means are provided within the housing to receive acoustical waves and convert the same to electrical signals. Non-contacting commutation means may be provided. These signals may be electrical signals which are converted to convenient data display format, such as a video output, may be in the form of a direct visual output as by light emitting diode arrays or other suitable means. The integrated scanner is adapted to be relatively lightweight such that a user may readily operate the instrument while holding it within one hand.

In one embodiment an endless belt is provided within the housing and adapted for orbital movement therewithin. Piezoelectric transducers are secured to the exterior of the endless belt and drive means disposed within the housing are provided for establishing the desired orbital movement. Non-contacting commutation means energize the transducers and transfer reflected transducer signals toward the exterior of the sealed housing. A flexible fresnel deflecting lens is disposed between the endless belt and a mechanically compliant wall of the sealed housing. Means for reciprocating the fresnel lens in a direction generally perpendicular to the direction of the orbiting transducers is provided. This results in a rapid mechanically reliable B-scan type of reading. The endless belt may be mounted upon a pair of rotatable pulleys which may serve as the armatures of electric motors disposed within the sealed housing. Internal signal handling means disposed within the housing may communicate with external signal processing means through electrical cable means.

In another embodiment the sealed housing which contains an acoustically conductive liquid is provided with an endless belt mounted for orbital movement in a first direction and translational movement in a second direction. At least one transducer and one light emitting diode are secured to the exterior of the belt. Drive means disposed within the sealed housing drive the endless belt in the orbital first direction and translational second direction. Magnetic commutation means commutate acoustical signals received by the transducer, and additional commutation means energize the light emitting diode. Electrical cable means are operatively associated with the drive means and in communication with the exterior of the sealed housing.

In another embodiment of the invention a sealed housing may have a subdivided interior or have two chambers within which an acoustically conductive liquid is disposed. A rotatable drum is disposed within the first chamber. At least two rows of transducers are disposed on the circumference of the drum generally aligned with the central axis thereof with the rows spaced circumferentially from each other. At least two rows of light emitting diodes are disposed on the circumference of the drum generally aligned with the central axis of the drum. Electric drive means are provided for rotating the drum. An array of sound pipes having a generally curved surface adjacent the drum and a generally flat surface at the other end or receiving end thereof is provided. A wall of the sealed housing is preferably flexible so as to permit more intimate contact between a test specimen and the sound pipe array either directly or through an acoustical coupling medium. Acoustical waves impinging upon the flat surface of the sound pipe array will be transmitted to the drum transducers through the curved surfaces.

Another embodiment of the invention involves an integrated closed ultrasonic scanner having a sealed housing which may be provided with an internal division or two chambers and containing an acoustically conductive liquid. A rotatable drum is disposed within the sealed housing and the front wall of the drum is oriented generally transversely to the longitudinal axis of the drum and rotatable therewith. A linear array of receiving transducers is secured to the front wall. A rear wall of the drum is oriented generally transversely to the longitudinal axis of the drum and rotatable wtherewith. A linear array of light emitting diodes is secured to the rear wall. Electric drive means are provided for rotating the drum. Internal electronic means are disposed within the sealed housing and coordinate the energizing of the light emitting diodes responsive to acoustical signals received by the receiving transducers. External electronic means are disposed exteriorly of the housing and energize the electric drive means and cooperate with the internal electronic means.

140 Claims, 63 Drawing Figures

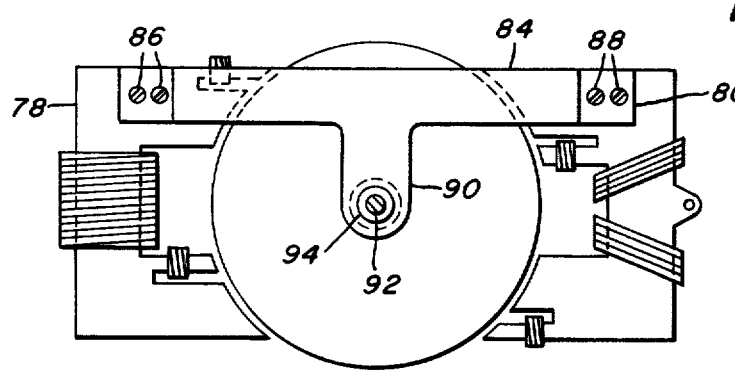
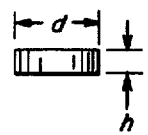
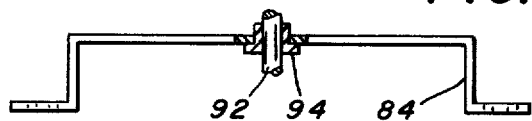
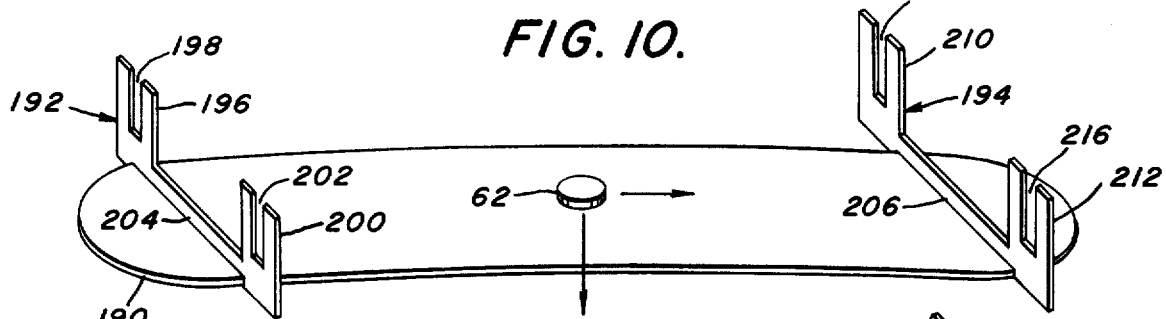
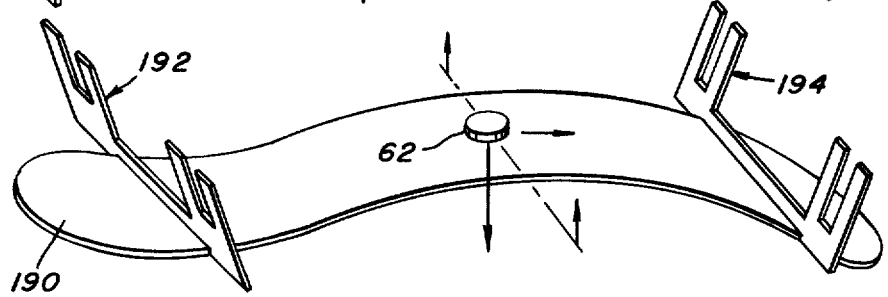
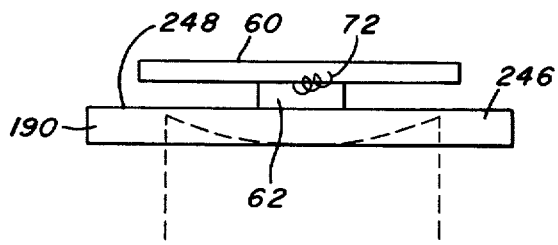
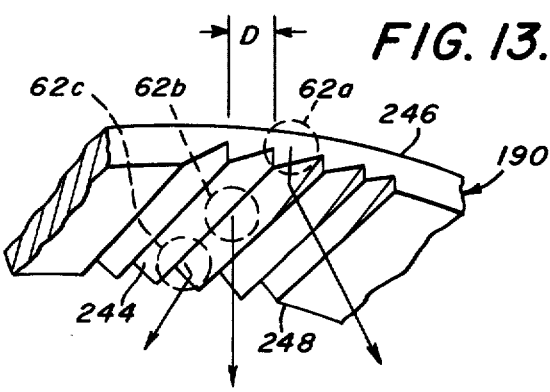

½  1  1½  2  2½  3  3½ etc.

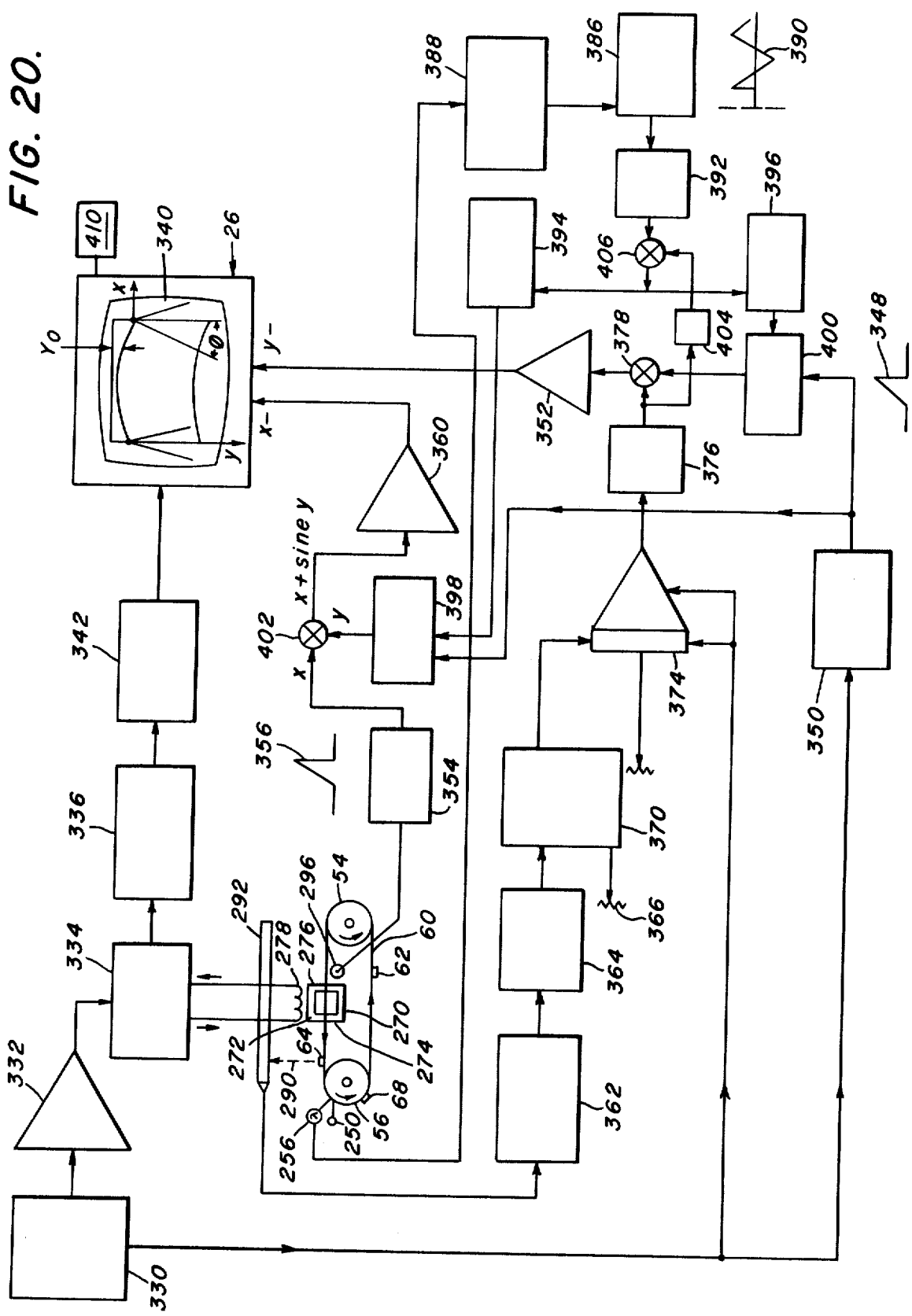

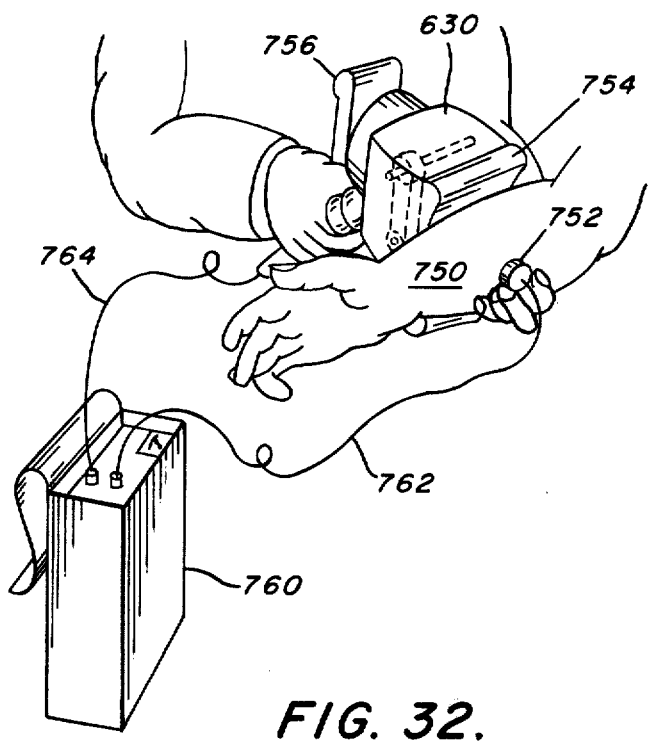
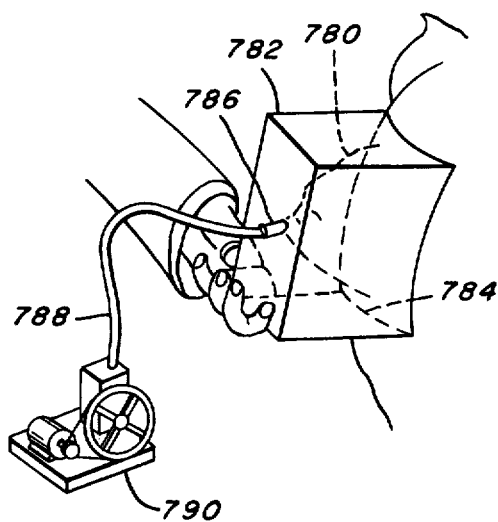
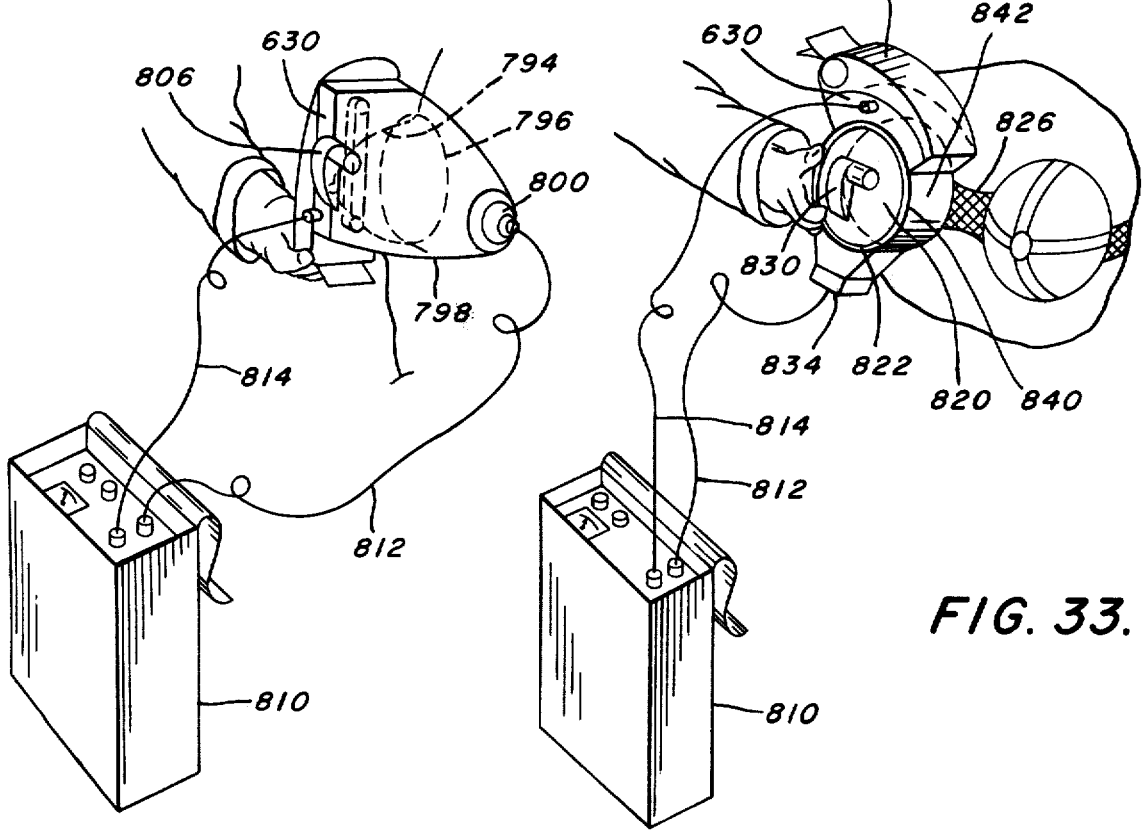

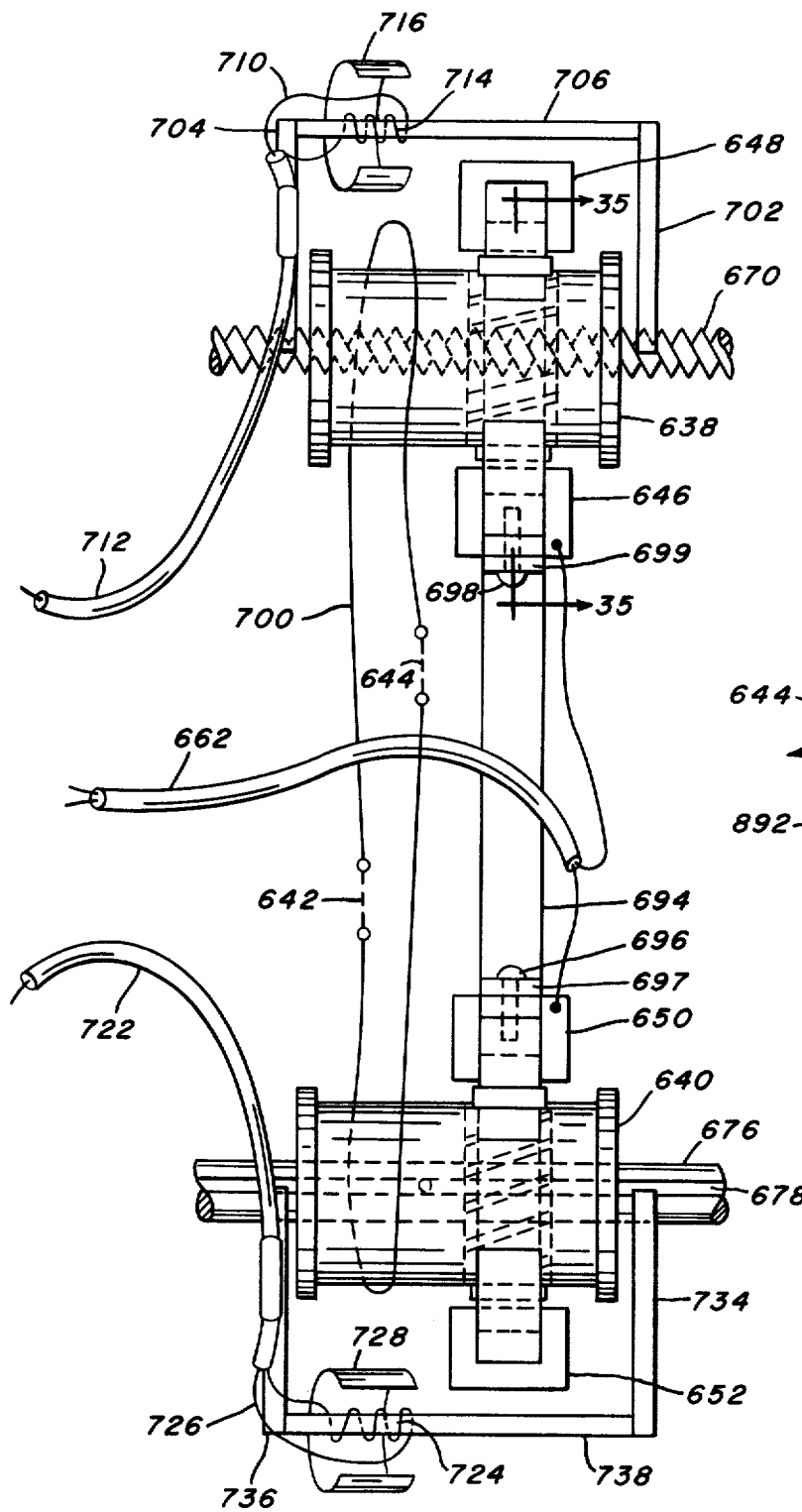
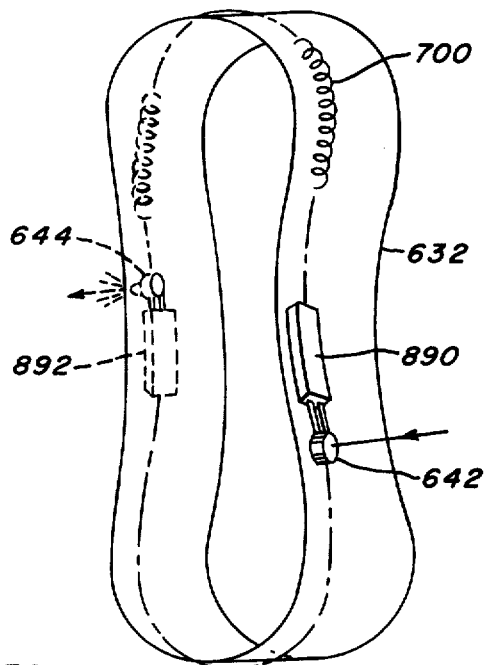
FIG. 34.
FIG. 37.

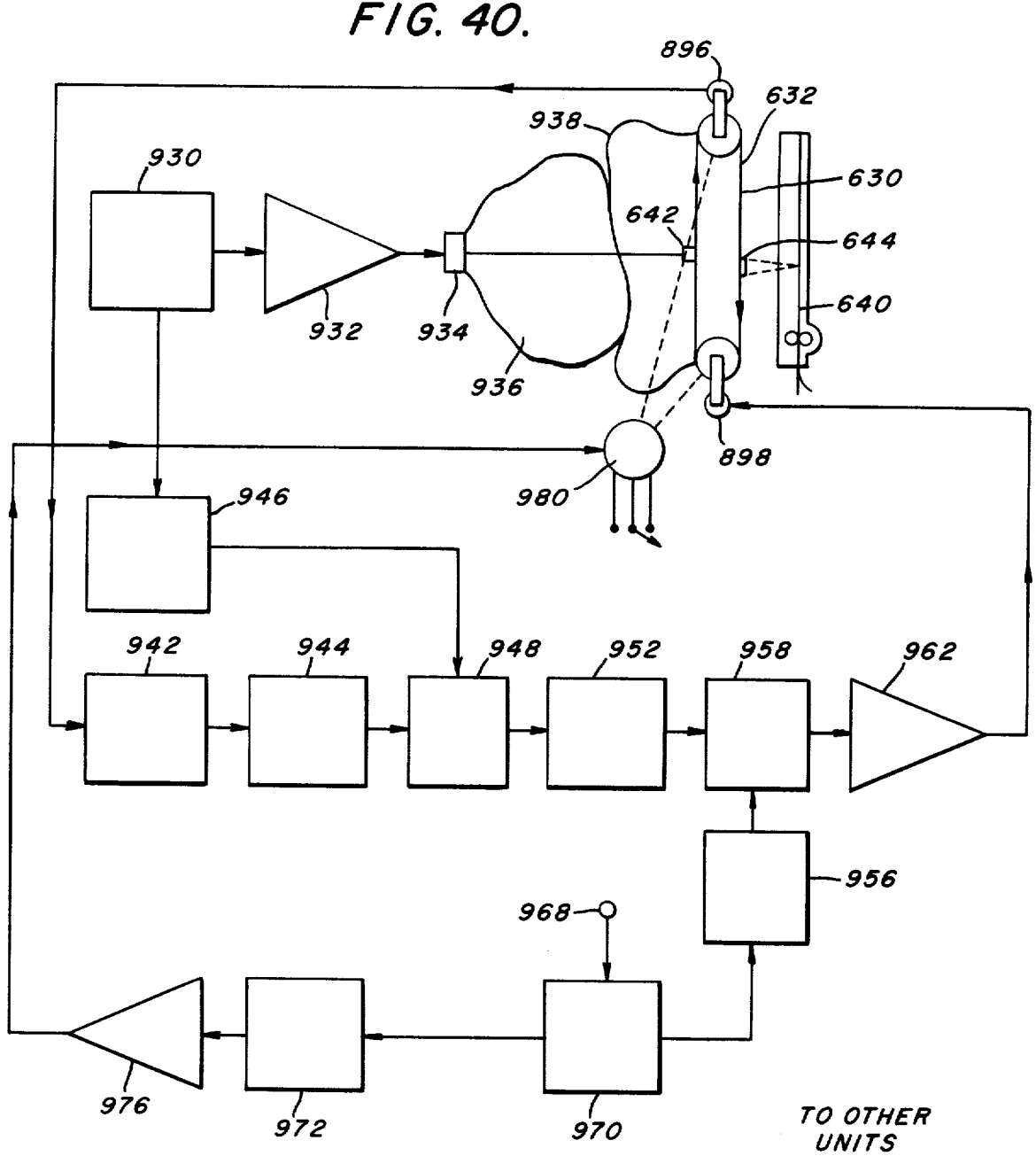
FIG. 40.
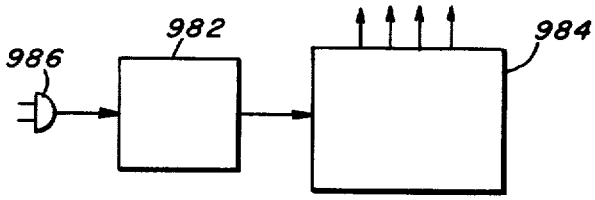
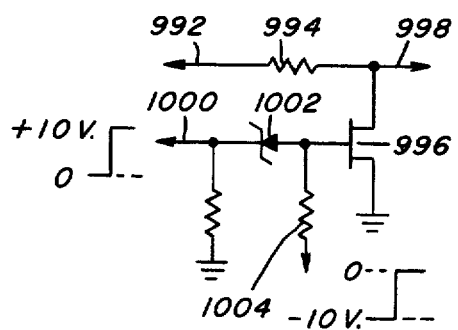
FIG. 41.

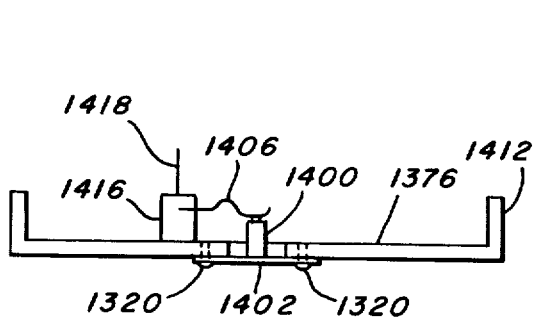
FIG. 55.
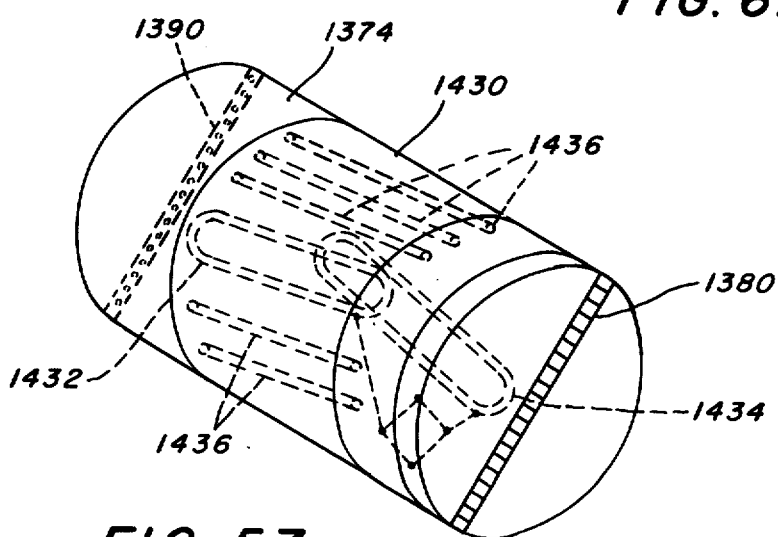
FIG. 59.
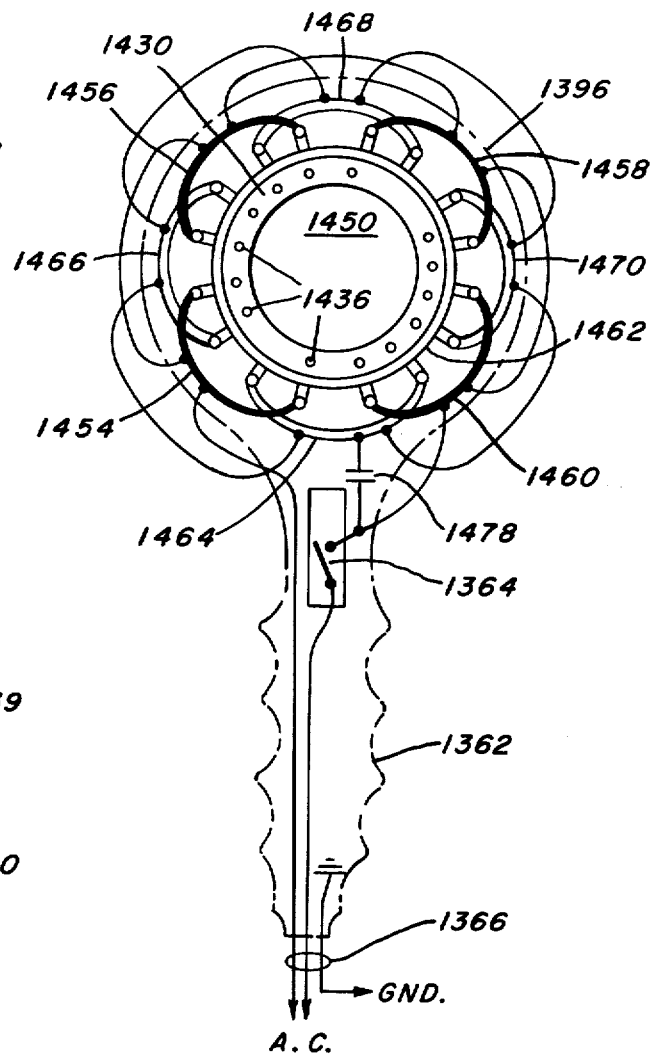
FIG. 61.
FIG. 57.

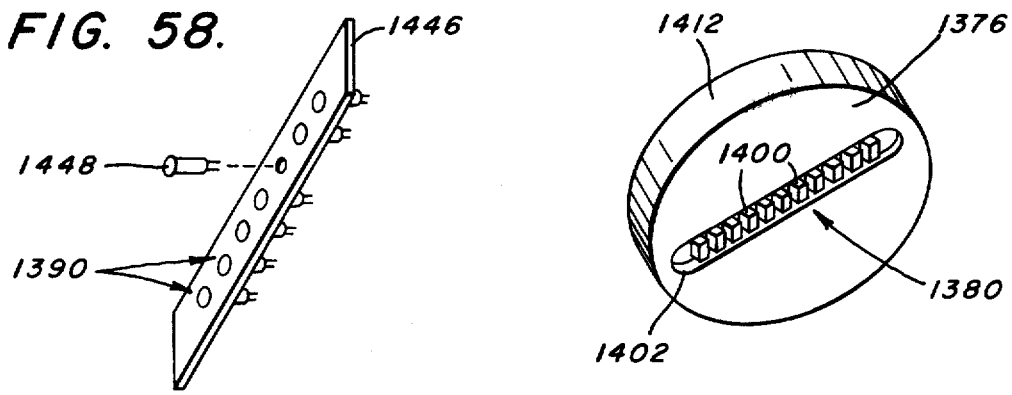
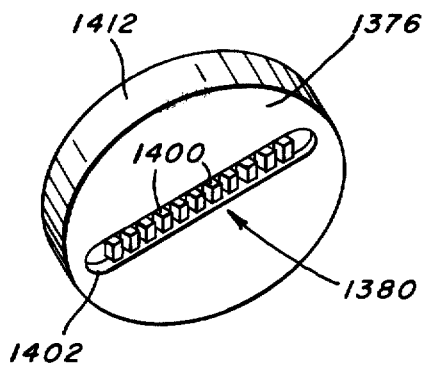
FIG. 58.
FIG. 60.
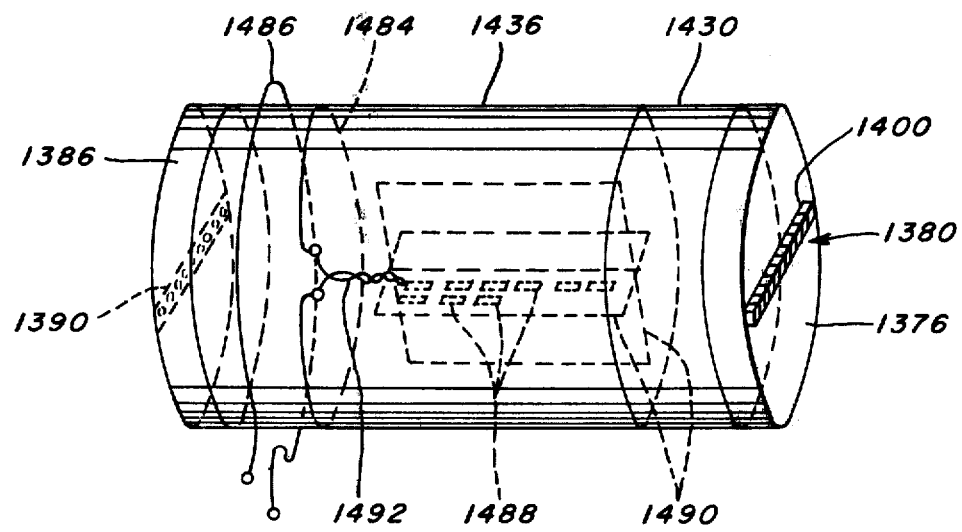
FIG. 62.

INTEGRATED ULTRASONIC SCANNING APPARATUS

BACKGROUND OF THE INVENTION

1. Field of the Invention

This invention relates to integrated closed ultrasonic scanner apparatus and, more specifically, such apparatus which is adapted to be lightweight and provided in a miniaturized housing so as to be readily portable and manually supportable, if desired, when used with a wide range of test specimens including various medical subjects.

2. Description of the Prior Art

In general, with ultrasonic testing of a test specimen in a medical environment, as well as certain other environments, there have been two specific approaches applied to use of ultrasonics. In a first approach, an insonifying transducer may be applied in acoustically coupled relationship with a greased patient or workpiece. In a second more restricted approach, a patient or portion of the patient or other workpiece is immersed in a liquid filled inspection tank. Generally with respect to medical use it has been customary to obtain a B-scan reading, for example, of the patient's abdomen, by manually moving a pressure-wave transducer transversely across the patient's abdomen while angularly rocking the transducer in a direction generally transverse to the direction of travel across the patient's abdomen. A common form of scanning with respect to metal workpieces has involved manually sliding a diagonally directed shear wave transducer along the metal workpiece while maintaining acoustical coupling between the transducer and workpiece.

U.S. Pat. No. 3,159,023 discloses a submergence method wherein an oscillating transducer produces an ultrasonic beam that becomes deflected by a parabolic mirror along its way to a workpiece which is also submerged at the bottom of an inspection tank. A rather complex submergence method intended for medical applications is disclosed in U.S. Pat. No. 3,023,611. This concept requires almost total submergence of the patient in a sitting position. In order to minimize the undesirable inconvenience to patients of requiring liquid tank acoustical environment and submergence therewithin, efforts have been made to minimize the degree of submergence required. In U.S. Pat. Nos. 3,765,403 and 3,585,847 a special mammographic clamping mechanism was disclosed as a means for holding a portion of the patient submerged in the acoustical environment.

U.S. Pat. No. 3,480,002 discloses a further effort to minimize the use of submergence procedures in connection with medical ultrasonic testing. In this disclosure a patient in supine position lies below a small flexible liquid filled bag which is acoustically coupled to the patient's breast or abdomen by means of an acoustical couplant, such as a grease, which is in contact with the bottom of the bag. Linear transverse or B-scan and rocking (sector) scan is thus automated, but required a very complicated and cumbersome suspended mechanical linkage. A variation of this liquid filled bag approach is disclosed in U.S. Pat. No. 3,603,303 wherein a portion of a patient or workpiece is introduced into a shallow pan-like liquid filled bowl and transducers which are disposed exteriorly of the liquid scan along guide lines from below. Further attempts to automate the combined angular and linear scanning motions required for B-scan medical imaging are described in U.S. Pat. Nos. 3,605,724, 3,448,606 and 3,547,101 all of which employ such scanning in combination with X-ray apparatus.

One particular problem in connection with the use of a transducer probe which is to be employed through manual manipulation of both linear and angular scanning motion is that such usage is quite sensitive to operator skill. Both gray level renditions and resolution capabilities which are extremely important to the amount of information and reliability of information produced by the test procedure are highly dependent upon operator skill. For example, one operator may scan the probe across a subject or workpiece much faster than another and thus obtain a darker, more sparsely scanned image. U.S. Pat. No. 3,690,311 attempts to provide compensation for variations in operator dependent scanning systems by adjusting the pulse repetition rates accordingly in order to attempt to establish an improved more uniform display. There remains a further problem in connection with lack of uniformity in scanning line densities and the need for compensation thereof. This type of compensation becomes quite important whenever a circular scan format is employed in lieu of a cartesian format.

As an alternate approach to attempting to substitute mechanical motion subject to variations in operator skill, it has been suggested that an electronically switched array of stationary transducers may be employed. See, for example, U.S. Pat. No. 3,789,833. As is apparent from the disclosure, there is the need to simulate both translational and angular rocking motion of a transducer probe. This disclosure provides multiple arrays in which three linear arrays of transducers are sequentially scanned with each array scanning along different search angles. One severely restrictive obstacle to adoption of such an approach is the requirement for the extremely large number of transducers and electronic circuits needed to simulate a reasonably large number of manual search traverses and angles as commonly executed by the physician during an ultrasonic tomogram manual scan procedure.

A further problem in connection with efforts to electrically or mechanically automate transducer scanning procedures is encountered in connection with the need in respect of rotating or reciprocating transducer scanning movements to effect commutation of the electrical signal to and from the transducer. This has generally been accomplished through the use of a flexible wire or other contacting commutation means familiar to the electrical trade as such means have been applied in the design of rotating machinery or rotating electrical instrument components. U.S. Pat. No. 3,779,234 discloses a rotating scanner within a catheter bulb and the commutation means involving a magnetically actuated reed switch selection of transducer connections. This selection is then commutated to the exterior of the piece of equipment by means of a mercury pool arrangement.

Even in fields unrelated to the area of the present invention there has been lacking a solution to the commutation problem. For example, U.S. Pat. No. 3,652,793 discloses a reciprocating scanning carriage for facsimile means. The connection to the exterior is effected by flexible wires. Examples of the inadequate non-environmental art in respect of belt driven apparatus are disclosed in U.S. Pat. Nos. 3,662,103 and 2,990,184. The former fails to suggest any unique commutation means, while the latter disclosures would be totally unsuitable for use of a belt either near or within a liquid filled region. Also found in the facsimile art is the drum-like facsimile equipment disclosed in U.S. Pat. No. 3,280,251 wherein a method of engaging a feed screw to effect sub-scanning motion is disclosed.

The possibility of generating a display raster of either the holographic or direct imaging type in direct proximity with the scanning plane of the transducer has been investigated, but only in a rather primitive and nonportable forms. For example, U.S. Pat. No. 3,632,183 describes a concept of moving a transducer light bulb pair along a two dimensional lead screw driven scanner format. Not only does the bulb follow the transducer motion, but the intensity of bulb illumination is needed to correspond precisely to the transducer signal by a photosensor-actuated intensity controlling servomechanism. The concept of mapping a transducer's arrays sound distribution by a matrix of lights has been disclosed in U.S. Pat. Nos. 3,450,225 and 3,461,420. U.S. Pat. No. 3,467,216 suggests the idea of mapping the sound distribution of a receiving array of transducers on the same site by locating an indicating lamp next to each transducer. None of these disclosures teach or suggest any form in which the array could be microminiaturized and mounted as a closed integrated system in such fashion as to be highly mobile and adapted for effective rapid scanning to provide a visual output at a faster rate.

U.S. Pat. No. 3,156,110 and 3,292,018 disclose the use of a multicolor display cathode-ray tube in the use of diagnostic ultrasound with particular emphasis on the visualization of benign and malignant tumors. In these disclosures several ultrasonic frequencies are employed and several corresponding color components related to ultrasonic reflection amplitudes at each respective frequency are provided and used to characterize the type of tissues according to the relative reflection voltage amplitudes among these several frequencies.

U.S. Pat. No. 3,564,904 discloses multicolored acoustical holograms for diagnostic medical applications. This disclosure, however, which involves a through-transmission method, is not practical for use as a color-coding scheme to represent changes of velocities of sound such as would be experienced in impinging ultrasonic beams upon bone and adjacent flesh portions. As bones have a higher velocity of sound than soft tissues, the bones would transmit the sound through the subject about 4 to 8 microseconds, for example, sooner than the surrounding tissues.

There is, therefore, lacking in the prior art a teaching of an encapsulated closed ultrasonic scanning mechanism which is readily portable and readily manually supported during operation. There is further lacking such an instrument which is adapted for reliable mechanical movement of transducers of either the B-scan or through-transmission variety within the enclosure coupled with internal electronic means, which may be of the integrated circuit variety, for processing the received acoustical waves after they have passed through the test specimen. There is further lacking in the prior art disclosures teaching non-contacting commutation means which permit ready and effective communication between the interior of the capsule and exterior operating and motive power source and data processing or data readout means. There is further lacking in the prior art means for rapidly moving a transducer or transducer array so as to simulate a B-scan and provide data which may by means of non-contacting commutation devices be communicated exteriorly of the capsule so as to permit data readout which may conveniently be presented on a cathode-ray tube. There is further lacking means for establishing translational and orbital movement of a receiving transducer or array of transducers so as to permit through-scanning of the area. In addition, there is lacking such an encapsulated scanning apparatus adapted for direct viewing or direct photographic recordal of the results when the system is combined with interiorly disposed light emitting diodes, which emit light responsive to receipt of acoustical waves by moving receiving transducers which are electrically coupled to the light emitting diodes.

SUMMARY OF THE INVENTION

The present invention has solved the above-described problems by providing lightweight, portable, encapsulated integrated scanning apparatus adapted to provide rapid and reliable scanning through predetermined mechanical movement of transducers within a sealed housing. Processing electronics disposed within the housing provide electrical signals directly related to the received transducer acoustical waves. Unique commutation means of the non-contacting variety couple the exterior of the housing with the interior thereof. External signal processing means are provided to provide the desired data readout form.

In a B-scan embodiment of the invention an endless belt is provided with at least two transducers which are adapted to both provide insonification as well as receipt of reflected acoustical waves returning from the test specimen. The endless belt having the mounted transducers is disposed within the sealed housing and is driven by electric motor means contained therewithin. A reciprocating fresnel lens disposed within the housing serves to simulate the rocking motion which would be applied during a manual B-scan operation as the transducer probe was moved along a linear path. The electric motor means for driving the belt may take the form of pulleys upon which the endless belt is supported with the pulleys serving as rotors of an electric motor having field windings positioned on stators disposed closely adjacent to the pulleys. Commutators may provide means for transmittal of the electrical output which is related to the reflected acoustical waves received by the transduer. The electrical output of the encapsulated scanner may then be converted to a desired data readout form. One preferred approach is to provide data readout in the form of a cathode-ray tube.

In another embodiment of the invention a through-transmission type of endless belt system is employed wherein the endless belt not only moves in an orbital fashion by means such as pulleys and electrical motors of which the pulleys may form a part, but also unique translational driving means causes the pulleys to move in a direction generally parallel to their axis of rotation.

In another embodiment of the invention a rotating drum is provided within the housing or capsule with rows of acoustical receiving transducers and light emitting diodes positioned about the circumference of the drum generally parallel to the longitudinal axis of the drum. Internal electronic handling means disposed within the drum serves to establish illumination of predetermined light emitting diodes responsive to receipt of an acoustical wave by predetermined transducers. Data conveniently may be transmitted exteriorly of this embodiment by providing a rear display window which may be a magnifying lens or have one disposed adjacent thereto. Either direct viewing or recording in permanent record form as by photographic means may be effected through the viewer window, if desired.

In another embodiment of the invention, the housing may contain a rotating drum provided with end mounted generally radially oriented linear arrays of transducers on one drum face and light emitting diodes on the other drum face. Rotation of the drum establishes rotation of the transducer and light emitting didoe arrays. Electronic means disposed within the housing establishes illumination of predetermined light emitting diodes responsive to receipt of an acoustical wave by predetermined transducers. If desired, a flexible end wall may be provided at the front end or transducer bearing end of the housing in order to facilitate more intimate acoustical coupling with the specimen as a result of more complementary configuration therewith.

It is an object of this invention to provide a high resolution, portable self-contained ultrasonic scanning apparatus which is adapted for use on a wide range of specimens including medical test specimens.

It is a further object of this invention to provide such a scanner wherein rapid continuous ultrasonic scanning may preferably be effected with data output being obtained through non-contacting commutation means in some embodiments and through a window viewer in other embodiments.

It is a further object of this invention to provide means for establishing rapid medical movement of transducers disposed within the housing and, in some embodiments, rapid mechanical movement of light emitting diodes adapted to be illuminated responsive to receipt of acoustical signals by predetermined transducers.

It is a further object of this invention to provide such an acoustical scanner imaging system wherein the human factor involved in B-scan type ultrasonic testing is essentially completely eliminated while providing improved speed of data collection, improved signal processing and improved display.

It is a further object of this invention to provide such a portable ultrasonic scanning system which will eliminate the need for objectionable submergence of the specimen within a tank of liquid.

It is a further object of this invention to provide such scanners which may be adapted for use in either B-scan through-transmission type environments.

It is another object of this invention to provide such a system wherein both electric motor drive means for establishing mechanical movement within the housing and certain electronic data handling means are provided within the housing.

These and other objects of the invention will be more fully understood from the following description of the invention, on reference to the illustrations appended hereto.

BRIEF DESCRIPTION OF THE DRAWINGS

FIG. 8 shows a top plan view of a form of bracket securing a pair of stators associated with a given rotor to each other.

FIG. 9 is a side elevational view partially in section of the bracket shown in FIG. 8.

FIG. 10 is a partially schematic view of a fresnel lens and anchoring plates in undeformed position.

FIG. 11 is a view of a fresnel lens and anchoring plates of FIG. 10 in deformed position.

FIG. 12 is a cross sectional partially schematic view showing the fresnel lens and its relationship with the belt and belt mounted transducer.

FIG. 13 is a fragmentary view showing vane portions of the fresnel lens.

FIGS. 14a and 14b show, respectively, perspective and side elevational views of a form of transducer employed in the present invention.

FIG. 20 is a block diagram showing some of the electrical energizing and external signal processing means employed in the embodiment of the scanner shown in FIG. 2.

FIG. 30 illustrates a form of the embodiment shown in FIG. 29 along with a test specimen and associated external equipment.

FIG. 31 illustrates an optional specimen receiver adapted for use with a female breast test specimen.

FIG. 32 illustrates a modified form of the concept of FIG. 31 used in combination with the embodiment of scanner shown in FIG. 29.

FIG. 33 is a further modification of the FIG. 29 embodiment adapted for effecting tests at various angles with respect to the breast.

FIG. 34 is a partially schematic cross sectional view of the embodiment of the invention shown in FIG. 29.

FIG. 37 shows a partially schematic perspective view of a form of endless belt adapted for use with the embodiment of FIG. 29.

FIG. 40 is a block circuit diagram of the embodiment of scanner shown in FIG. 29.

FIG. 41 is a circuit diagram of linear gate adapted for use with the circuit diagram of FIG. 40.

FIG. 55 is a cross sectional, partially schematic detail of a transducer bearing plate adapted for use in the embodiment of FIG. 54.

FIG. 57 is a fragmentary partially schematic perspective view showing a portion of the drum-like interior of the embodiment of FIG. 54.

FIG. 58 is a schematic illustration of a light emitting diode array.

FIG. 59 is a circuit diagram illustrating a portion of the interior circuitry of the scanner of FIG. 54.

FIG. 60 is a partially schematic view of an array of the scanner of FIG. 54.

FIG. 61 is a partially schematic view of the embodiment of FIG. 54 showing a portion of the electric motor circuitry.

FIG. 62 illustrates another view of the drum-like embodiment of FIG. 54 in perspective and partially schematically with an illustration of the commutation antenna means.

DESCRIPTION OF THE PREFERRED EMBODIMENTS

As used herein the expression "test specimen" will refer to various types of specimens to be tested by ultrasonic B-scan or through-transmission means including medical tests wherein portions of a human or animal body are tested ultrasonically. While for purposes of clarity of description specific reference will be made to use in medical environments, it will be appreciated that other forms of test specimens may be subjected to testing by the apparatus of this invention in addition to the preferred medical use and such other use is expressly contemplated.

First Embodiment (FIGS. 1 through 28)

Figure 1:
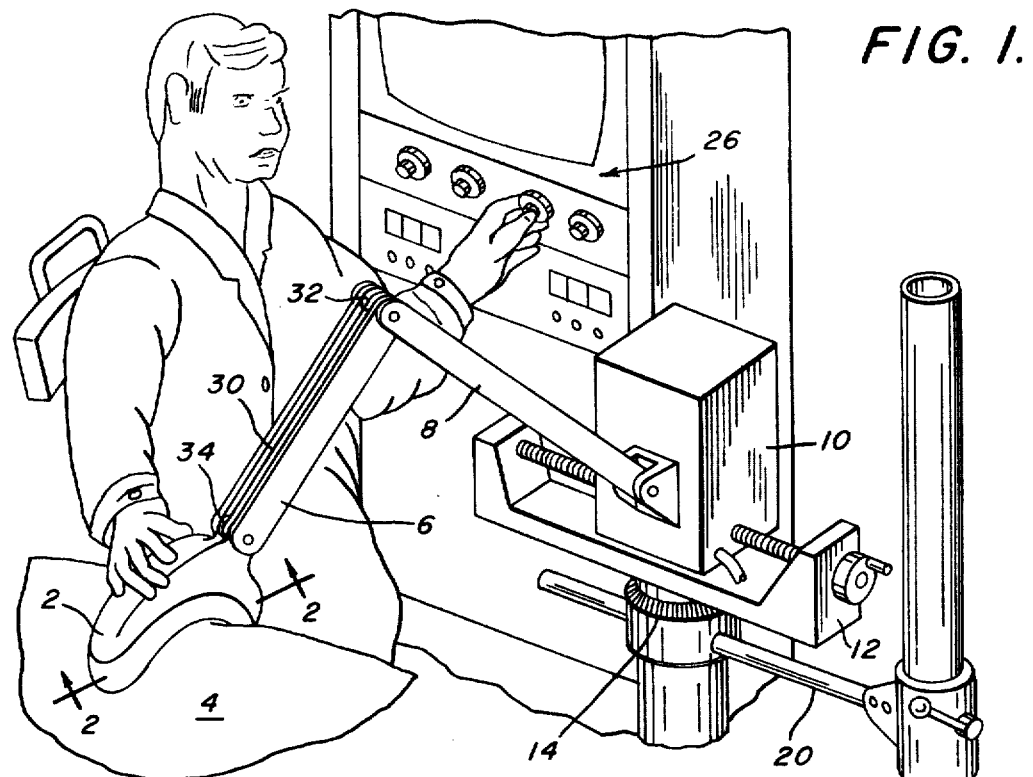
FIG. 1 is a partially schematic view of one form of the invention showing structural support means for holding the scanner in a predetermined relationship with respect to the test specimen and certain data display means.

Referring now more specifically to FIG. 1, there is shown a form of scanner 2 of this invention with the scanner being held against a test specimen 4 which has been illustrated schematically as a representation of an abdomen of a human patient. It is contemplated that the patient would be facing upwardly in a reclining position upon a suitable supporting table (not shown). In this illustration of scanner 2, it is noted that while scanner 2 is readily adapted to being manually supported by a physican or operator, a suitable linkage support mechanism, which may be of any desired variety and forms no part of the present invention per se, is being employed. A suitable form of support arm mechanism is that marketed by Picker under the trade designation "Echoview Model VI". In the specific form shown, linkage arm 6 is pivotally connected to linkage arm 8 which in turn is pivotally mounted on box 10. It should be noted that appropriate adjusting means 12, 14 are provided for assisting with specific positioning of the scanner 2 with respect to specimen 4. Support arm 20 is adapted to be slideable upon post member 22 and placed in a desired fixed position thereon. Post member 22 is supported upon tripped 24.

Appropriate display consoles 26 which permit desired readout of data are provided. Such a display console 26 may conveniently take the form of a visual display monitor, such as a cathode-ray tube system.

In using the scanner 2 of FIG. 1, the operator places a suitable acoustical couplant material between the scanner 2 and the test specimen 4. A suitable material is that sold under the trade designation "Ultraphonic Conductivity Gel" manufactured by Pharmaceutical Innovations, Inc. As will be described in detail below, the lower surface of scanner 2 has a flexible or compliant wall which is adapted to bend upwardly in a concave fashion so as to conform to the outward contour of the contacting portion of the test specimen. Portions of the interior components of the scanner 2 are similarly designed to assume a complementary configuration with respect to the test specimen while maintaining the desired mechanical transducer movement and electronic processing.

The electronic processing converts received acoustical signals into electrical output signals which may be evaluated by means of display consoles 26 or any other desired means. One particularly desirable form of display console 26 is a non-storage cathode-ray tube, as this provides the additional advantage of permitting continuous gray level B-scan images to be observed at a frame rate of about 15 images per second, for example. In addition, such gray level images can be preserved by a time exposure photograph, if desired. In the event the operator desires to see only totally black or white type of restriction in the gray level dynamic range, as is the case when measuring biparietal diameter of a fetal skull, for example, a simple increase in display contrast and threshold adjustment (commonly called "reject") in video presentation causes the non-storage cathode-ray tube to display an image equivalent to the high contrast storage-tube display. In the event that the physican or operator desires to rotate scanner 2 about the test specimen 4 so as to provide a transverse tomogram section, for example, from the side, pulleys 32, 34 cooperate with cable 30 to facilitate such repositioning. Box 10 may contain conventional continuously revolving angular and translational potentiometers which serve to facilitate electrical signals indicating orientation of scanner 2 to display console 26 thereby causing the B-scan image on display console 26 to rotate in step with the physican's or operator's manual movement of scanner 2. As this forms no part of the invention per se and is fully known to those skilled in the art, no further description of this optional complementary feature is necessary.

Figure 2:
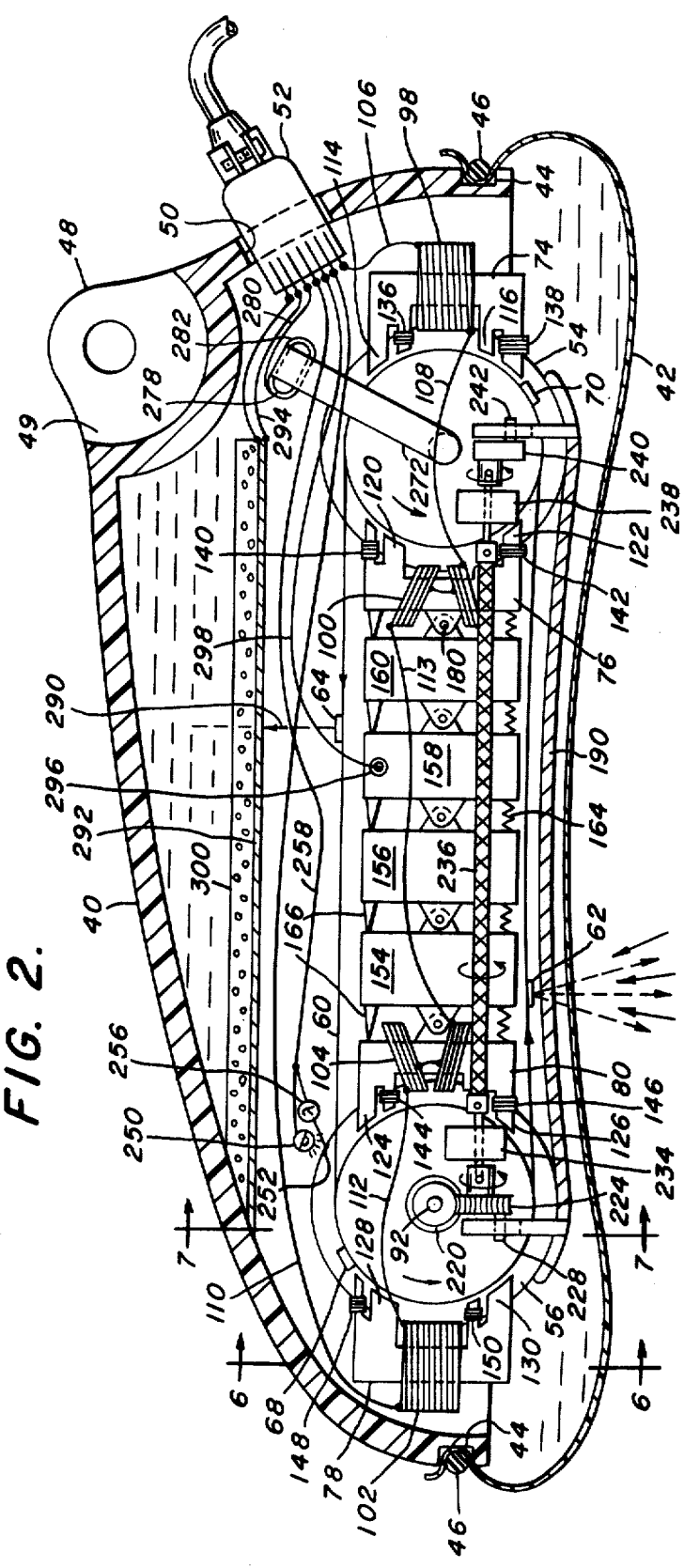
FIG. 2 is a cross sectional illustration of the type of scanner shown in FIG. 1 taken through 2—2 of FIG. 1.

Referring now to the cross sectional illustration of scanner 2 shown in FIG. 2, it is seen that the scanner has a sealed housing which is defined by a substantially rigid case member 40 and a mechanically compliant or flexible web 42. In the form illustrated, a sealed enclosure is established by providing an outwardly open recess 44 within case member 40 preferably substantially continuously about the circumference thereof and securing a portion of flexible web 42 within recess 44 by a suitable retaining member such as O-ring 46. The case member 40 may conveniently be formed from an electrically insulated rigid plastic material such as molded rigid vinyl or polystyrene. The flexible web may conveniently be a plastic material such as soft vinyl or neoprene, for example, or other suitable, durable, non-porous flexible materials. Case member 40 is provided with connecting section 48 which has opening 49 for use in securing scanner 2 to linkage arm 6. Suitable means (not shown) may be employed to secure the internal components of scanner 2 to case member 40, if desired.

The interior of the sealed housing contains an acoustically conductive liquid which preferably fills the same exclusive of the scanner components contained therein. A suitable resealable opening (not shown) for filling the housing with liquid or checking the liquid level may be provided, if desired. Among the preferred conductive liquids for such purposes is silicone oil which provides an effective acoustical coupling, is inherently non-corrosive and also provides lubrication and heat dissipation for the moving parts within the sealing housing. A particular preferred material is the silicone oil sold under the trade designation "Dow-Corning Type 710 Silicone Oil". Among the other suitable materials are glycerine and ethylene glycol. While not preferred, water could be used, but this would necessitate design of the interior components so as to make them corrosion resistant.

Referring still to FIG. 2, there is shown an opening 50 within case member 40 through which passes electrical cable means 52. Cable means 52 provides for electrical communication between the interior of the sealed housing and the exterior thereof. Not shown in FIG. 2 is a suitable sealing material or element which would be disposed betwen the portion of case member 40 defining opening 50 and cable means 52 so as to resist loss of coupling fluid from the interior of the sealed enclosure.

The present embodiment of the invention in its preferred form contemplates the handling or processing of electrical signals within the sealed housing and certain handling or processing of electrical signals exteriorly of the sealed housing. For convenience of reference herein the equipment employed to handle or process electrical signals within the sealed housing will be referred to as the "internal signal handling means" and the equipment for external handling or processing will be referred to as the "external signal processing means". It will be appreciated that external signal processing means may be secured directly to the sealed housing as by creating an outer enclosure or may be in a separate unit electrically connected thereto. The internal signal handling means will generally be in communication with the external signal processing means through cable means 52.

In this embodiment of the invention the electrical signal which the internal signal handling means emits through cable means 52 to external signal processing means will be an electrical equivalent of the reflected acoustical beam received by a belt mounted transducer. For convenience of reference herein, such an electrical signal will be referred to as the "acoustical function electrical signal".

Figure 4:
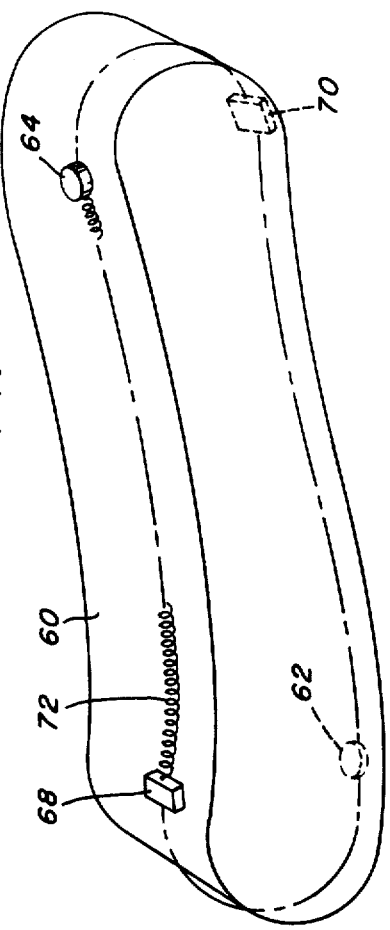
FIG. 4 is a schematic view of the endless belt shown in FIG. 2.

As is shown in FIG. 2, there are a pair of pulleys 54, 56 rotatably mounted within the sealed housing in spaced apart relationship. An endless belt 60 is positioned over the two pulleys 54, 56 under sufficient tension to rotate with the pulleys. In the preferred form of endless belt 60, it is composed of an elastic fabric which is continuously woven and is under elastic tension between pulleys 54, 56. An example of a preferred material for manufacturing endless belt 60 is composed of about 73% cotton, 16% rayon and 11% rubber such as the waistband elastic sold under stock number 49874 by W. T. Grant Company. Another suitable approach would be to employ a relatively inelastic belt with suitable take-up means such as a spring positioned pulley. Secured to the exterior surface of endless belt 60 are a pair of piezoelectric transducers 62, 64. Also secured to the exterior of the belt are a pair of permanent magnets 68, 70. As is shown in FIG. 4, the transducers 62, 64 are circumferentially spaced with respect to each other on belt 60. They are shown as being generally equidistant from each other regardless of which direction along the belt the distance is measured.

Similarly, the permanent magnets 68, 70 are positioned at predetermined distance from the transducers 62, 64. Also secured to endless belt 60 is an extensional commutation spring 72 (see FIG. 4) which serves to connect transducers 62, 64 electrically in series. The spring may conveniently be made of phosphor bronze spring wire of about 0.005 inch diameter, for example.

In the form of the invention illustrated in FIG. 2, the pulleys 54, 56 also act as armatures or rotors of alternating current induction motors. Such pulleys may be comprised of machined nylon or delrin with implanted motor armatures, for example. While this particular form of motor has been selected for illustration, it will be appreciated that the pulley could serve as the armature or rotor of other types of motors including, for example, a permanent magnet rotor of a commutatorless direct current motor.

As is shown in FIG. 2, each pulley 54, 56 is provided with a pair of associated stators. Pulley 54 has a stator 74 positioned on the exterior side thereof and stator 76 positioned on the interior side thereof. Similarly, pulley 56 has exterior stator 78 and interior stator 80.

Referring now to FIGS. 2, 8 and 9, the manner of securing the stators to the associated pulleys will now be considered. Making reference to pulley 56, it is seen that the associated stators 78, 80 are composed of epoxy-coated silicon steel laminations and are secured in fixed spaced relationship with respect to pulley 56 by means of bracket 84 which has its opposed upper ends secured, respectively, to stators 78 and 80 by screws 86, 88 or other suitable fasteners. The bracket 84 has a depending leg 90 which has an opening within which is received pulley shaft 92. For convenience of rocking action associated with scanner placement in contact with a nonplanar test specimen surface about pulley shaft 92, a suitable bushing 94 which may conveniently be made of graphited nylon, for example, is provided. While not shown in this view, an opposed substantially identical bracket 84 will be positioned at the opposite side of stators 78, 80 with the depending leg of such bracket also having an opening receiving pulley shaft 92. In this fashion, the stators 78, 80 are secured in such position with respect to pulleys 56 as to permit relative rocking motion therebetween while preserving the relative spacing between stators 78, 80 and pulley 56. The brackets 84, may preferably be so positioned as to maintain a controlled spacing of about 0.03 inch between the poles and the rotors.

Figures 6, 7:
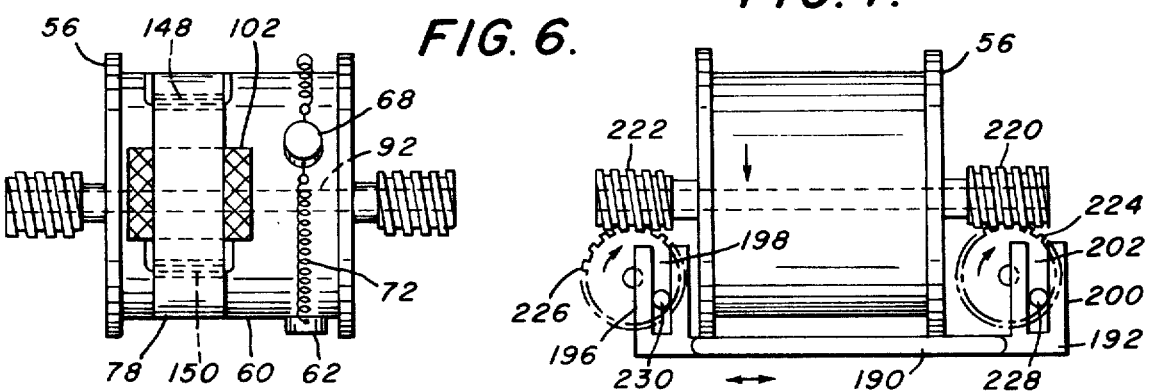
FIG. 6 is a cross sectional view of the scanner of FIG. 2 taken through 6—6 of FIG. 2.
FIG. 7 is a cross sectional view of the scanner of FIG. 2 taken through 7—7 of FIG. 2 and showing a portion of the fresnel reciprocating lens.

Referring now to FIGS. 2 and 6, it is seen that the generally U-shaped stators 74, 76, 78, 80 have primary field windings 98, 100, 102, 104, respectively. In the form illustrated electrical wire 106 connects field winding 98 with cable means 52 thereby providing a source of energy for the same. Electrical wire 108 connects field winding 100 with field winding 98 thereby energizing the same. Similarly, field windng 102 is connected by electrical wire 110 with cable means 52 thereby energizng the same. Finally, electrical wire 112 connects field winding 102 with field winding 104 to provide energy for the latter and electrical wire 113 connects field windings 100 and 104. Field windings 98, 100, 102, 104 provide the main magnetic fields on pole pieces 114, 116, 120, 122, 124, 126, 128, 130. Stators 74, 76, 78, 80 also have pole pieces provided with shorting bars 136, 138, 140, 142, 144, 146, 150, respectively, which produce quadrature phase delayed fields, such as are caused by pole shading which is commonly employed in the electrical trade as applied to fractional horse-power alternating current induction motors. It will, therefore, be appreciated that each pulley 54, 56 comprises a portion of an electric motor not requiring brush or slip-ring type of commutation and that these pulleys drive the endless belt 60 in an orbital path. As the belt has two transducers 62, 64, in the form shown, but may have more if desired, one complete revolution of the belt will correspond with two complete scans. Typically, this could be accomplished in one-fifth of a second, for example.

In considering the motors discussed for pulleys 54, 56, with the split pole pieces, the rotating magnetic field produced could generate a non-slip rotor speed of about 1800 rpm which would correspond to about 30 revolutions per second. Assuming a substantial reduction for the viscous damping action of the liquid contained within the sealed housing, the actual motor speed might be about 1200 rpm correspondng to 20 revolutions per second of the pulleys.

Figure 3:
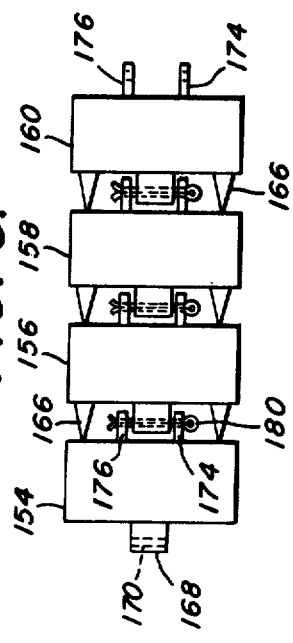
FIG. 3 is a partially schematic top plan view of the flexible mechanical adjustment means disposed between the pulleys shown in FIG. 2.

Referring now to FIGS. 2 and 3, the deformable linkage which permits deformation of the flexible web 42 and other portions of the scanner 2 while maintaining a working relationship between components thereof will be considered. In the form shown in FIG. 2, four vertebrae or connecting links 154, 156, 158, 160 are secured between inner stator 76 and inner stator 80 for relative movement therebetween. As a result of each pair of vertebrae and each vertebrae-inner stator joint having interposed therebetween resilient means, which in the form shown consists of a compression spring 164 in the lower position and a resiliently compressible pedestal member 166 in the upper position, the linkage will normally assume a generally linear undeflected position such as is illustrated in FIGS. 2 and 3. In the form illustrated, each link has a projection 168 from one side thereof which defines a transverse bore 170 and has a second projection in the form of a pair of projecting elements 174, 176 spaced sufficiently far as to receive first projection 168 and having openings for receipt of pin 180 which serves to permit relative rotational movement about the pin 180, while prohibiting translational movement or relative separating movement. If desired, the pin may conveniently be a cotter pin or other suitable fasteners, such as rivets, for example, could be used. The materials and compressive strengths of compressive springs 164 and pedestal 166 may be so selected as to permit the desired degree of relative movement between the respective links 154, 156, 158, 160. It will be seen that the inner stators 76, 80 are similarly secured to end links 160, 154, respectively.

The linkage elements 154, 156, 158, 160 are preferably each individually molded as a unit of material such as plastic. Nylon is a suitable material for this purpose. The receiving openings provided in members 174, 176 may conveniently be of different sizes such that the pin may form an interference fit with the smaller of the two openings and thereby be retained in position, athough cotter pins may be employed, if desired.

Referring now to FIGS. 2 and 10 through 13, the manner in which the B-scan rocking motion is simulated will be considered. As is shown in FIG. 2, a fresnel deflecting lens 190 is positioned between the lower extremities of pulleys 54, 56 and flexible web 42. In order to simulate the rocking action of the transducer, the fresnel deflecting lens 190 is subjected to reciprocating motion in a direction generally perpendicular to the orbital path of the transducers. In FIG. 2 this will represent relative movement into and out of the page.

As is shown in FIG. 10, the undeflected fresnel lens 190 is illustrated with the transducer 62 being shown for convenience of reference with the direction of relative movement thereof being illustrated by the arrow pointing to the right. The fresnel lens 190 is fixedly secured to a pair of anchor plates 192, 194 spaced from each other at a distance generally approximating the distance between the shafts of the two pulleys 54, 56. The anchor plates 192, 194 are secured to the fresnel lens by any convenient means which will resist movement therebetween. Anchor plate 192 has a first upstanding leg 196 which defines an upwardly open slot 198 and a second upstanding leg 200 which defines upwardly open slot 202. A base portion 204 connects legs 196, 200 and is secured to fresnel lens 190. Similarly, anchor plate 194 has a base portion 206 connecting with fresnel lens 190 and upstanding legs 210, 212 which define, respectively, upwardly open slots 214, 216. In the form shown, the anchor plates 192, 194 are secured to fresnel deflecting lens 190 by creating a cut-out in base portions 204, 206 and establishing an interference fit between the anchor plates 192, 194 and the fresnel lens 190.

Considering now the manner in which the fresnel lens 190 is reciprocated with respect to endless belt 60, reference is made to FIGS. 2 and 7. As is shown in FIG. 7, pulley 56 has axial projections on either side thereof which are provided with worm gears 220, 222. Gears 224, 226, respectively, mesh with worm gears 220, 222 and have, respectively, eccentrically mounted pawls 228, 230 which are received in upwardly open slots 202, 198, respectively. As a result, as pulley 56 rotates in the direction indicated by the arrows on FIGS. 7 and 2, the gears 224, 226 will rotate in the direction indicated by the arrows thereon. This causes responsive reciprocating movement of fresnel lens 190 in the direction indicated by the double headed arrow immediately underlying fresnel lens 190 in FIG. 7.

The reciprocating motion of the portion of fresnel lens 190 to which anchor plate 192 is secured is duplicated with respect to the end of fresnel lens 190 adjacent to anchor plate 194. In the form illustrated this is accomplished by means which connect the drive means for anchor plate 192 with anchor plate 194. While only one side of the connecting drive means is shown in FIG. 2, it will be appreciated that an identical arrangement to that described is provided on the other side of the linkage means 154, 156, 158, 160. For simplicity of description the one-half which is illustrated will be described. Referring to FIGS. 2, 7 and 10, gear 224 is by means of coupling member 234 secured to flexible shaft 236. Flexible shaft 236 is at its other end connected to coupling member 238 to which is secured a wheel 240 having an eccentrically mounted pawl 242 which is received within slot 216 of leg portion 212 of anchor plate 194. As a result, rotational movement of gear 224 will cause pawls 228 and 242 to establish reciprocating movement of anchor plates 192, 194 with similar movement being duplicated by pawl 230 within slot 198 and a second flexible shaft (not shown) coupled to gear 226 and another wheel mounted pawl (not shown) within slot 214.

Referring now to FIG. 11, it is noted that the fresnel lens 190 is shown in deformed position in which it has a downwardly concave configuration which is created responsive to effecting complementary contact with the underlying test specimen. It is noted that the transducer remains in motion in the direction indicated by the arrow pointing toward the right and that the deformation has not inhibited freedom of movement of the transducer or altered its position tangent to the lens 190.

Referring to FIGS. 12 and 13, it is seen that the undersurface of the fresnel lens 190 has a plurality of vanes shown generally as having a replication distance "D", which vanes are generally oriented transversely with respect to the direction of orbital path of the transducers 62, 64. The reference numeral 246 has been employed to indicate the front end of the fresnel lens vanes and the reference numeral 248 has been used to designate the rear end of fresnel lens 190. The lens vanes are so configurated as to provide means for deflecting the reflected acoustical waves (which have originated with the transducer on the endless belt, have impinged upon the test specimen and have reflected back into the scanner) in such fashion that for a particular relative position of the transducer and fresnel lens 190 the angle of receipt of the reflected wave by the transducer will simulate variations in angles of receipt such as would be encountered in connection with the manual rocking motion of the transducers during the conventional (manual) B-scan procedure. Such a fresnel lens, including the vane structure thereof, may preferably be composed of a molded nylon whose velocity of sound exceeds the velocity of sound in the surrounding liquid. This concept is shown schematically in FIG. 13 by phantom circles 62a, 62b and 62c and the associated arrows.

It should be noted that regardless of where the transducer appears in its scanning position, its surface will be generally tangent to any local curvature of the fresnel deflecting lens 190. The lenticular vane structures 244 (FIG. 13) are so configured as to change the orientation from the front 246 to rear 248. The effect on the acoustical beam is to angularly deflect such beam depending on whether the fresnel deflecting lens is offset sideways with respect to the direction of the transducer's orbital movement. As is shown in FIGS. 12 and 13 and the represented relative positions of transducer 62 in positions 62a, 62b, 62c, when the fresnel deflecting lens is shifted to the rear of transducer 62 as represented by position 62a, the received acoustical reflected beam will be deflected in a counterclockwise direction and when the fresnel lens is shifted in front of the orbiting transducer 62 as represented by position 62c the received acoustical beam will be deflected in a clockwise direction. The lenticular vanes 244 are so configured that the extent of such angular deflections will be proportional to the lateral displacement of the fresnel lens 190 from the central position. It is of significance to note that the individual lenticular vanes 244 of the fresnel deflecting lens 190 replicate within a distance D less than the diameter of transducer 62. This short replication distance may typically be in the neighborhood of 4 millimeters while the transducer 62 may typically have a diameter of about 10 millimeters. The effect of the short replication distance D is to minimize loss of transducer resolution while transmitting an acoustical beam through a periodic interferometric approximation of what could be a continuous transmitting lens structure. The maximum angular direction of the received acoustical beams established by fresnel lens 190 will preferably be about ± 30° from the usual undeflected perpendicular beam.

With regard to speed of reciprocation of the fresnel lens, this would generally correspond to an angular rocking speed which would be considerably slower than the time required for each B-scan. By way of example, for a typical fresnel lens reciprocating cycle, assuming that the endless belt effects a full cycle of rotation for each four revolutions of the pulley, five complete endless belt rotations would equal ten complete B-scans (two transducers 62, 64 on the belt) which in turn would equal twenty pulley rotations. In order to synchronize the electrical handling or processing with fresnel deflecting lens reciprocation, the pulley rotations are counted and the count is sent by electrical means through cable means 52 to counter circuitry disposed outside of the housing. In the form illustrated, this counting is accomplished by means of a lamp 250 (FIG. 2) which is disposed within the sealed housing closely adjacent to pulley 56. Pulley 56 is provided with a highly reflective spot 252 which may consist of a piece of polished stainless steel or similar highly reflective material secured to pulley 56, as by a suitable adhesive, and photocell means 256 is so positioned as to have its electrical resistance momentarily and periodically drop as a consequence of receiving reflected light flashes when pulley spot 252 is in a predetermined location with respect to lamp 250, i.e., one per revolution of pulley 56. Electrical conductor means 258 energizes lamp 250 and emits a signal through cable means 52 responsive to a photocell reduction in resistance. It will be appreciated that twenty such output signals from photocell 256 will thus correspond with ten B-scans or five complete belt rotations.

Figure 5:
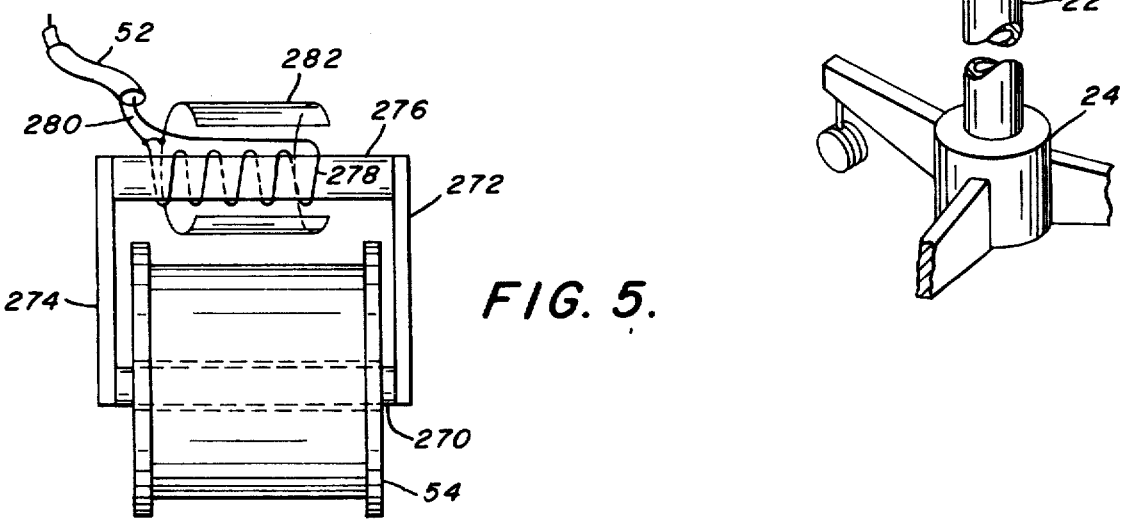
FIG. 5 is a partially schematic illustration of a form of magnetic commutation means of one embodiment of the invention.

Referring now to FIGS. 2 and 5, the non-contacting magnetic commutation means which functions to transfer energizing electricity between cable means 52 and the transducers and motors will now be considered. Shaft 270 of pulley 54 is highly magnetically conductive. It preferably consists of a finely powdered ferrite rod having good magnetic transformer properties in the frequency range of about 100 kilohertz to 10 megahertz and preferably in the frequency range of about 600 kilohertz to 4.2 megahertz. Shaft 270 serves as a portion of a closed magnetic loop which has connected thereto side members 272, 274 to which in turn is connected upper magnetic member 276. Side members 272, 274 and upper member 276 are also composed of materials having high magnetic permeability such as manganese zinc ferrite oxide ($Fe_2O_3$), e.g. Type A as sold by Magnetics, Inc. An electrical coil 278 which is wrapped around upper member 276 and is in electrical connecting relationship with cable means 52 through conductor 280 is provided. The coil is protected by Faraday shield 282 which may consist of a thin piece of copper preferably having a thickness of about 0.002 to 0.006 inch. As a result of this arrangement, electrical pulses arriving through cable means 52 will pass through electrical conductor 280 and into coil 278 and excite magnetic pulses in the loop created by elements 270, 272, 274, 276. Such magnetic pulses will induce electrical currents in extensional commutation spring 72 (FIG. 4) and these currents will pass through transducers 62, 64 thereby energizing the same and causing them to generate acoustical waves which will radiate outward from the transducers 62, 64 on endless belt 60 and pass downward toward the test specimen. After a suitable time delay ranging from about 16 to 300 microseconds, but most usually in the range from about 25 to 180 microseconds, a reflected acoustical pulse will impinge upon the downward facing ultrasonic transducer 62, 64 thus generating an acoustical function electrical signal whose amplitude depends upon the acoustical reflection coefficient between the various portions of the test specimen through which the emitted acoustical wave has passed, e.g., adjacent internal organs, fascia and tissue interfaces of the patient, and whose time of arrival depends upon the depth of the particular interface. The electrical pulse emitted by the transducer 62, 64 will typically fall within the range of about 3 microvolts to about 100 millivolts and will preferably be in the range of about 10 microvolts to 20 millivolts thereby creating a signal current pulse ranging from about 0.03 microamps to 1 microamp and preferably about 0.1 microamp to 0.2 microamp. This small current passes along extensional commutation spring 72 and in turn induces a small magnetic field in the magnetic loop which consists of elements 270, 272, 274, 276, which magnetic field in turn induces voltages in coil 278 of a magnitude that is about one-half the voltage generated by the downward facing transducer. The voltages in coil 278 that correspond to reflected acoustical pulses travel out through conductor 280 and cable means 52. These imaging pulses are then electrically directed away from the source of pulses (in a fashion to be described later) to a receiver that conditions these voltages to produce a desired output such as a suitable acoustical image on display console 26 (FIG. 1).

The commutational magnetic loop consisting of elements 270, 272, 274, 276 may typically have a length of about 16 centimeters with the elements having a cross sectional area of about 0.6 cm.$^2$ and relative permeabilities in the range of from about 200 to 800 and typical frequency ranges from about 600 kilohertz to about 4.2 megahertz. The coil 278 may typically have about 6 to 20 turns of enamelled magnetic wire wound with an inductance of about 200 microhenries. When considering the commutation spring 72 as a transformer winding, an effective transformer is created with a turns ratio of preferably in the neighborhood of about 10 to 1 and a coupling coefficient of about 0.5. This will result in extremely reliable and electrically noise-free operation.

As it is known that the reflections of acoustical waves from very shallow penetration in the test specimen are of questionable medical value as contrasted with those penetrations which extend beyond upper skin, fascia and fat layer structures for most purposes, the present scanner has means for making use of such shallow transmitted pulses to obtain an indication as to the degree of deformation of the flexible web 42, fresnel lens 190, adjustable linkage means 154, 156, 158, 160 and endless belt 60 caused by the force of the test specimen against the scanner housing. As both transducers 62, 64 are simultaneously emitting acoustical pulses, but neither pulse can be reflected until the elapse of about 16 microseconds, the upward pointing of the transducers, which in FIG. 2 is transducer 64, is used to send a reference beam 290 to a contour identification plate 292 which is disposed within the sealed housing in spaced overlying relationship with respect to endless belt 60. The contour identification plate 292 is preferably an elongated piezoelectric receiving-only transducer whose purpose is to receive only the first arrival acoustical pulse from the upward facing transducer 64. It will be appreciated that as the belt moves in its orbital path the transducers 62, 64 will alternate in their roles. The upwardly facing transducer in FIG. 2 is 64. The downwardly facing transducer 62 will be emitting acoustical wave which impinge upon the test specimen and are reflected back. The signals emerging from the contour identification plate 292 will be carried by electrical conductor 294 to cable means 52. The signals emerging from cable means 52 through electrical conductor 294 will be electrically processed to determine the actual deformed shape of endless belt 60 during the period the scanner is in contact with the test specimen and B-scanning is being accomplished. The reference beam 290 will ultimately provide a depth correction factor (to be designated below as "$Y_o$") which will be applied to the vertical direction signal on display console 26.

In the form shown in FIG. 2, both pulleys 54, 56 rotate in a counterclockwise direction and the transducers 62, 64 on the endless belt 60 scan from left to right. In order to coordinate the horizontal motion of the scanning lines on display console 26 with the start of scan procedures under the left pulley, reed switch 296, which in the form shown is secured to linkage element 158 and electrically connected to cable means 52 by conductor 298, momentarily closes due to action of permanent magnets 68, 70 which periodically are in close proximity to the reed switch as the endless belt upon which the magnets 68, 70 are mounted revolves. The period of closing of the reed switch may be about 2 milliseconds repeating about every 100 milliseconds. Closure of reed switch 296 completes a circuit through cable means 52 to external electronics causing scanning lines on display console 26 to start from the left side of the screen of console 26 in direct synchronization with the start of scan as one downwardly facing transducer 62, 64 is beginning to scan from a position underlying pulley 56.

As, in the form shown, only one of the transducers 62, 64 will be viewing the specimen at a given time, the other of the transducers 62, 64 should be made non-responsive to spurious echoes from the top of the housing as well as from the hand of the operator who may periodically have his hands in contact with the sealed housing. In order to accomplish this objective, an isolating layer 300 is positioned in overlying relationship with the contour identification plate 292 and is composed of a highly acoustical absorptive material. For example, an expanded polystyrene closed-pore material such as that sold under the trademark "Dylite" by Sinclair-Koppers Co. may advantageously be employed.

The type of transducer which may be used in this embodiment of the invention is generally a so-called B-scan type of transducer which is adapted to generate and emit an acoustical pulse and receive the reflected acoustical returning wave. In connection with the next embodiment to be described a similar type of transducer may be employed except that as it is a through-type ultrasonic system the receiving transducer need not have acoustical wave generating capabilities. While these types of transducers are fully known to those skilled in the art and do not form a part of the invention per se, it is believed that some discussion of certain preferred forms may be helpful to those skilled in the art.

Figure 15:
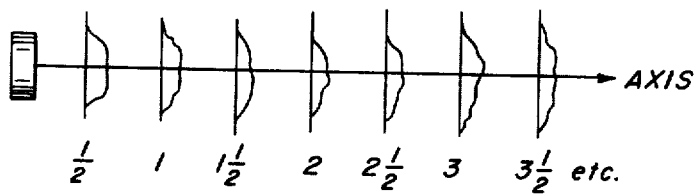
FIG. 15 illustrates schematically the transducer of FIGS. 14a and 14b and the associated emerging sound waves.
Figure 16:
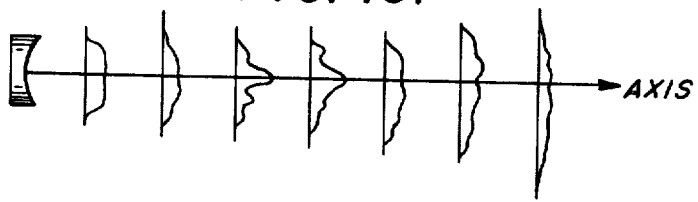
FIG. 16 illustrates a modified form of transducer and modified sound wave emerging therefrom.
Figure 17:
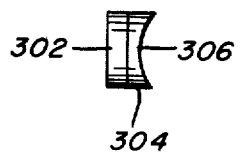
FIG. 17 illustrates a transducer and lucite lens combination.

In general, a cylindrical type of transducer having a diameter of about ¼ to ½ inch can efficiently be employed in connection with the endless belt mounted embodiments of this invention. Among the preferred transducer materials are the Glennite ceramic compositions manufactured by Gulton Industries, Inc. with the HS-21 being a barium titanate material and the G-2000 model being a lead metaniobate material. The barium titanate material has a high receiving sensitivity and a high dielectric constant which produces good drive capability to operate transistor input circuits. The lead metaniobate material has a low mechanical Q-factor of about 10 to 15 and results in a wider relative band width of about 10 to 20%. The lead metaniobate has a low dielectric constant of about 250 while the barium titanate has a dielectric constant of about 1050 and, as a result, the lead metaniobate is not believed to have the signal drive power capability to efficiently send a received acoustical pulse through long cables or to effectively drive conventional transducer circuits. This weakness can be overcome by employing a field-effect transistor, such as type 2N5459 sold by Motorola, in close proximity to the transducer. One of the most desirable characteristics of the lead metaniobate is that it is softer than most other transducer ceramics and can be easily shaped by lapping and grinding methods. Shown in FIGS. 14a and 14b are representations of a cylindrical transducer having a height h of about 0.04 inch and a diameter d of about 0.3 inch. Such a transducer can produce an approximate collimated acoustical beam. As is shown in FIG. 15, the transducer of FIGS. 14a and 14b produces a broad beam pattern generally equal to the transducer diameter for a distance of several inches. By grinding a hollow concave shape into the emitting face, such as is shown in FIG. 16, the beam pattern can be made to constrict at the focal length. Such constriction results from the spherical wavefront generated at the front concave surface of the transducer. When a transducer is ground to focus, the radius of the spherical concave depression corresponds to the desired focal length. In order to effect the same benefits as the concave surfaced transducers shown in FIG. 16, a cylindrical transducer may be secured to a lucite lens having the same concave configuration. In FIG. 17, there is shown a transducer 302 which may be of the type illustrated in FIGS. 14a and 14b and 15 secured to which is a lucite lens 304 having a concave face 306.

In general, as between the materials described up above, the version shown in FIG. 16 is most easily created out of the lead metaniobate material as it is relatively soft and the alternate shown in FIG. 17 may best be employed with the barium titanate material as it is relatively hard. Comparing further the relative advantages of the collimated approach of FIGS. 14a and 14b and 15 as contrasted with the focused approach of FIGS. 16 and 17, it is noted that the collimated approach has a relative depth of field of about 3 inches, while the focused design obtains better resolution for a more restricted depth of field of about 1 inch. As the diameter of the transducer (of either the collimated or focused type) increases, the far field (about 2 to 3 inches) range behavior improves, at the expense of loss of resolution in the near field (about ½ to 1 inch) region. The transducer thickness generally determines the resonant frequency of operation. For the specific materials discussed above, the resonant frequency is about 2.3 megahertz (MHz) for a thickness of about 0.040 inch. Also, the resonant frequency varies generally inversely with transducer thickness. Such reverse variations means that a transducer with variations in thickness such as those shown in FIGS. 16 and 17 has the additional advantage of obtaining a more diverse frequency response as a result of the different thicknesses along the surface. In connection with through-transmission acoustical signals, the special resolution of the individual transducers is not as important and correspondingly small diameters are generally used.

When the lucite lens approach of FIG. 17 is taken, the plano-concave lens is made wherein the spherical cut-out is approximately one-half the previous radius owing to the refractive index (about 1.4 to 1.6 for sound, referring to water as the reference medium).

When a transducer is employed as both a transmitter and a receiver, the typical received acoustical reflection from a strongly reflecting surface, such as a copper plate, for example, is about 40 decibels below the transmitted voltage level, while weak reflectors such as the human body return reflection signals ranging from about 60 to 80 decibels below the transmitted voltage level. The electrical loading factor of the receiver circuits generally cause about another 10 decibel loss in signal strength. For example, as a B-scan type of sending and receiving transducer receives a 300 volt pulse, typical acoustical reflections from medical test specimens will fall within the range of about 3 to 30 millivolts as sent across the input circuit of the receiving electronics.

Figure 18:
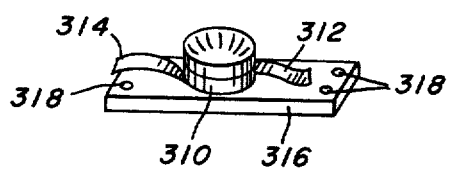
FIG. 18 illustrates a form of transducer mounted on a base which may be readily secured to an endless belt of this invention.
Figure 19:
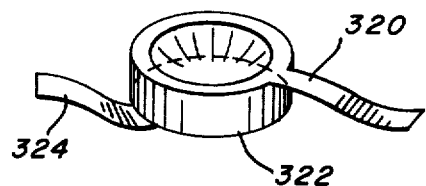
FIG. 19 is a modified form of transducer construction adapted for securement to a belt of this invention.

Considering now a method of attaching a transducer to endless belt 60 and using for purposes of example the composite transducer of FIG. 17, reference is made to FIG. 18 wherein a transducer 310 has a phosphor bronze spring temper shim element with projecting portions 312, 314 cemented thereto by means of a suitable adhesive such as a silver, conductive adhesive. An example of such an adhesive is the material sold under the trade designation Poly-Comp 21–301 by Polymer Composites of Arvington, New Jersey. The phosphor bronze shim could be type ASTM B-103, B & S Gage No. 44 (0.002 inch thick), for example. A suitable plate member 316, such as a lucite plate, is provided with holes 318 by means of which the plate may be secured to the endless belt 60. In the event that a transducer of the type shown in FIGS. 15 or 16 were employed, the upper cemented seam could take the form of an annular contact 320 as is shown in FIG. 19 with lower seam 322 also being adhesively secured thereto. It is preferable, however, to coat the upper and lower transducer surfaces with a conductive cement in order to couple all acoustical signal areas with the external electronic coil 278 (See FIG. 20).

Considering once again the function of the liquid within the sealed housing, it should be noted that the liquid not only serves the function of the acoustical couplant and the above mentioned lubricating function, but it may also function as a coolant for the field windings and stators. While the motors would not tend to generate an excessive amount of heat, it would be desirable to have the benefit of maximum cooling action in the interest of motor efficiency. The movement of the belt and pulleys will tend to create a laminar region of liquid flow following the belt. The moving liquid will tend to absorb heat from the motor and transfer the same to the surrounding sealed housing. As the amount of heat generated would not normally be great, it is not anticipated that the heat will reach a human subject's body temperature. In order to maximize human comfort, if desired, an internal heating element and controlling thermostat (not shown) could be provided to keep the housing at body temperature prior to activation of the motors and to generate only so much heat as would be required to make up for the difference between dissipated motor heat being transferred to the exterior of the sealed housing and that needed to maintain the housing at body temperature.

Referring now to FIG. 20, a description of the functioning of the integrated scanner and the coordination of the internal signal handling means with the external signal processing means will be considered. As is shown in FIG. 20, a pulse generator 330 acts as a master timer for the entire system. This generator emits short pulses which may, for example, be about 2.0 microseconds in duration and about 5 volts in amplitude, positive going and have a repetition rate in the range of about 200 to 4000 pulses per second and preferably within the range of about 700 to 2000 pulses per second. Pulses emitted by generator 330 are received by pulse amplifier 332. The pulse amplifier 332 amplifies the received pulses and may, for example, produce a peak height of about 300 volts. The amplified pulses pass through the transmit-receive box 334 and from there pass to the magnetic commutation device (see FIG. 5) which consists of coil 278 with Faraday shield 282 and the magnetic loop consisting of elements 270, 272, 274, 276 which for convenience of reference in this portion of the text will be referred to as the "commutation device".

Another function of the transmit-receive box 334 is to direct received acoustical function electrical signals from the commutation device toward logarithmic receiver 336. It will be appreciated that one of the functions of the transmit-receive transmitted high-voltage pulses from overloading the logarithmic receiver 336. The logarithmic receiver develops a rectified low pass filtered video voltage which is proportional to the logarithm of the amplitude of the acoustical pulse voltages caused by acoustical reflection from the test specimen. By way of an example of a typical change in receive voltage amplitude ranging over 66 decibels (from 10 microvolts to 20 millivolts), the output of the logarithmic receiver 336 varies at the rate of +1 volt increase in output for every factor of ten increase in input signal voltage. Such logarithmic compensation and dynamic response is provided in order to display conveniently both intense near reflections and far weak reflections on the cathode-ray tube 340 of display console 26. The output voltage of receiver 336 which may, for example, be on the order of about 4 to 10 volts in amplitude, is amplified by video amplifier 342 to a high voltage amplitude which may, for example, range from about 30 to 80 volts peak to peak. Such amplified voltages are fed into the variable intensity input (grid No. 1) of cathode-ray tube 340 of display console 26.

As electrical pulses are commutated to and away from endless belt 60, transducers 62, 64 emit and receive pulses from the patient and generate reference beam 290. In order to display the received reflected acoustical signal coming from the test specimen, the cathode-ray tube should preferably have a spot on the screen deflected downward at the rate of about 6 to 8 inches per 200 microseconds in order that about 6 inches penetration depth within the test specimen is indicated on the cathode-ray tube. Pulse generator 330 triggers a ramp function output wave 348 from Y-sweep generator 350. Ramp waveform 348 eventually feeds the Y-deflection amplifier 352 which in turn feeds the Y-deflection coils within display console 26.

During operation of the scanner, momentary closures of reed switch 296 provide a trigger signal to X-sweep generator 354 which causes it to emit a ramp waveform 356 which may be about 100 milliseconds in duration. This ramp waveform 356 eventually feeds the X-deflection amplifier 360 which then operates the X-deflection coils within display console 26. The effect of the X-deflection in the display format is to cause the scanning lines in the Y-deflection to process across the screen of the cathode-ray tube 340 synchronously with the transducer 62 or 64 motion across the test specimen from left to right within a 100 milliseconds interval.

In order to follow the contouring of the scanner 2 and path of the transducer 62, 64 that scans the patient, the reference beam 290 is received by the contour identification plate 292. The voltage output from the contour identification plate 292 occurs after the leading edge of the master timing pulse and the time interval between both signals is proportional to the physical distance between (1) the upper of the belt mounted transducers 62, 64 and (2) the contour identification plate 292. The signal from the contour identification plate is sent to second logarithmic receiver 362 and the receiver output drives video amplifier 364 which in turn compares the amplified voltage against a reference voltage 366 in threshold detector 370. This sequence of signal processing steps is taken to positively identify the reception of the reference beam 290 by the contour identification plate 292 and is used to create a direct current voltage whose value depends upon the physical contour of scanner 2. This voltage is generated by integrator 374 and accumulates a ramp voltage upwards going from the time the master pulse starts until such rise is quenched by a stop trigger signal from the output of threshold detector 370. As integrator 374 provides many rapidly slewing voltage outputs and only a steady direct current output equal to the peak of each slewing waveform is required, a peak detector 376 is provided to follow only the crests of the integrator output. This peak value voltage ($Y_o$) is combined with the normal Y-deflection signal at adder 378 in order to vertically offset the Y-deflection line on display console 26 in proportion to the physical contour of scanner 2 upon the test specimen. Voltage supply means 410 provides high voltage and focus voltage to cathode-ray tube 340.

Inherent in the system as described to this point is the fact that the contour correction system is devised to operate when the test specimen is substantially symmetrically deforming the scanner 2 as the signal from contour identification plate 292 is in technically reversed time sequence as compared to the transducer to test specimen scan motion. In order to provide accurate correction for asymmetrical contouring the $Y_o$ voltage values should be stored in a small conventional digital "buffer memory" which enables the $Y_o$ voltages to be read in reverse order with respect to the sequence in which they are generated.

In the form described above, the reflected acoustical beam deflects in an angular fashion of about 60° arc as the fresnel deflecting lens 190 undergoes reciprocating motion. In order to bend the Y-deflection scanning lines to conform to the slowly changing acoustical beam orientation through the test specimen, several signal processing steps take place. First of all, the rotation of pulley 56 is counted by means of the lamp 250 and photocell 256 to provide a pulse output voltage after a predetermined number of revolutions of the pulley. In the example stated above, the figure of 20 revolutions was employed. The photocell output signal passes through a digital divide by 20 circuit 388. The output from counter 388 triggers a ramp generator 386 that provides a triangular waveform output 390 which drives a sine generator 392. The output of the sine generator 392 is a sine wave whose voltage value and polarity are directly proportional to the relative position of fresnel lens 190. The output of sine generator 392 eventually feeds sine generator 394 and cosine generator 396 whose output operates, respectively, modulator 398 and modulator 400 (both of which may conveniently be multipliers). By providing control signals that represent the sine and cosine of the direction of the acoustical beam angles, the Y-deflection signal initially fed only through the Y-deflection circuits now becomes mixed into both the X and Y-deflection circuits so that the Y-scanning line on display console 26 bends in proportion to the bending of the acoustical reflecting beam. The Y-deflection voltage is diminished in proportion to the cosine of the beam angle deviation and the X-deflection voltage has a small amount of Y-deflection voltage mixed in mixer 402 in proportion to the sine of the beam angle deviation.

As the contouring of this scanner as it is deformed in contact with the test specimen causes the transducer beam to depart from the vertically downward direction into the test specimens for reasons other than lateral movement of the fresnel lens 190, additional Y-deflection compensation is preferably provided. Such compensation is achieved by taking the first time derivative at differentiator 404 of the $Y_o$ signal and mixing this derivative at mixer 406 with the previous control signal from sine generator 392. The rapidly changing $Y_o$ value must refer to a steep slope on the contour while a stagnant $Y_o$ value means that the contour is either non-existent or the contour signal is riding a crest along the contour where the acoustical beam returns to the vertically downward direction. As a result, the steep slopes on the contour of the scanner 2 generate relatively large contour voltages in order to angularly deflect the Y-deflection beam to follow the inward bend of the transducer beam.

While the particular external signal processing means illustrated and described in connection with the block circuit diagrams of FIG. 20 form no part of the present invention per se and may consist of conventional circuit elements such that one skilled in the art should require no further guidance in practicing the present invention, in order to provide additional assistance and guidance some illustrative components will be discussed and considered at this point.

EXAMPLE

A suitable voltage supply means 410 is that sold under the trade designation Series HV by Gould, Inc. of Newton, Mass. These units typically require an input voltage of about 105 to 125, a current of about 1.5 amperes and a frequency (single phase) of about 57 to 420 Hz. The output voltage ranges from about 10 to 25 kilovolts DC and an output current of about 1 milliampere. The filament output is about 6.3 VAC and about 1.0 ampere. The turn on delay range is about 0 to 20 seconds and the operating temperature is about 0 to 60°C.

A specific form of suitable video amplifier 342 is that sold under the trade designation Model BBA 4324 Unblank/Video Amplifier by Gould, Inc. This unit is an all silicon solid state unit and requires a video input of 3 volts maximum, an impedance of 75 ohms or 5 K ohms and has a positive polarity. Video section output has an amplitude of 60 volts, positive polarity, a band width of −3 db points from direct current to 1.2 MHz. The output level (grid No. 1 bias) is variable from −40 to −120 volts and the temperature range is +10 to +60°C, with a temperature stability of about 0.075%/°C.

The X-sweep generator 354 and Y-sweep generator 350 may both be contained within one unit and be of the type sold under the model designation SG1190 by Gould, Inc. The saw tooth generator is an all silicon solid state unit. Connections to this generator should be modified in order to accept the external trigger signal from reed switch 296. With respect to inputs of the X and Y-drives, the application of 3 to 5 volts negative causes the saw tooth output to be in the resting or "off" state, while the application of 0 ± 0.5 volts causes the saw tooth output to be ramping, in the "on" state. This saw tooth output swings from +5 to −5 volts, with negative-going slope. The input power is 20 volts at 100 MA, −20 volts at 60 MA and −35 volts at 20 MA. With respect to output the X and Y saw tooth amplitude ranges from +5 volts to −5 volts with an impedance of 100 ohms maximum. The width is 6 microseconds to 100 milliseconds. Adjustments to width or amplitude of ±50% may be made. The operating temperature is 0°C to +60°C and the non-linearity is ±0.1% maximum.

Figure 21:
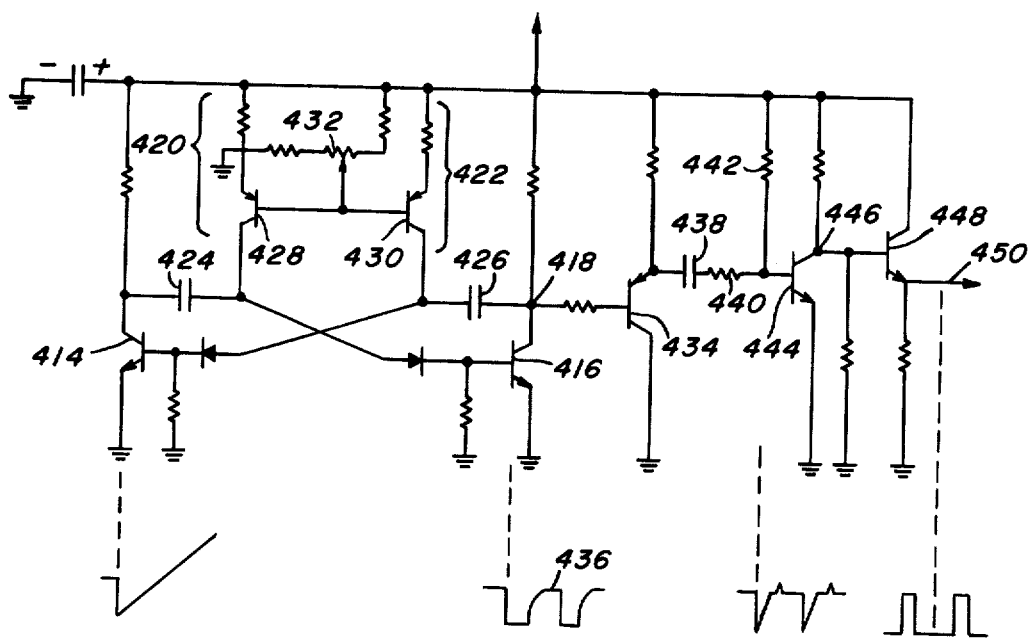
FIG. 21 illustrates a circuit diagram of a form of pulse generator employable with this invention.

Referring now to FIG. 21, transistors 414 and 416 form the working parts of a conventional Eccles-Jordan multivibrator, whose operation is well known to those skilled in the art. This multivibrator produces a square-wave output at collector 418 of a transistor 416. (The waveforms are shown in FIG. 21 underlying the related circuit portion.) The only modification made on the well known Eccles-Jordan design in the form shown is the substitution of constant-current source circuits 420 and 422 in place of the usual resistors to discharge capacitors 424 and 426. This substitution is made in order to improve the frequency stability of the multivibrator, and to afford a greater adjustable frequency range. In addition, such frequency adjustment is frequently made remotely from the circuit board containing such a multivibrator, and the possibility of eliminating the second (normally required) ganged potentiometer offers savings in lead-connections and in cost of the potentiometer. The inclusion of the relatively inexpensive constant-current circuitry, consisting of transistors 428 and 430 and associated resistors and single frequency-adjustment potentiometer 432 is provided both to improve circuit performance and to reduce production and assembly costs. Transistor 434 is a conventional emitter-follower stage, whose function is to duplicate the incoming waveform 436, but with improved current-supplying capability into capacitor 438. Capacitor 438, in concert with resistors 440 and 442, forms a current-runup system that times a short negative-going discharge during the negative-going voltage swing output from the multivibrator. This discharge is frequently chosen to be a small fraction of the period of the multivibrator. For instance, if the multivibrator operates at a frequency of 2000 Hz, corresponding to a period of 500 microseconds, the capacitor 438 would be selected to provide a negative-going discharge of about 5 microseconds. Once such a discharge is obtained, it turns transistor 444 off for the discharge time-duration, causing the collector 446 to provide a positive-going voltage pulse which is generally square in shape, and lasting the same duration (5 microseconds, typically) as the discharge time. Another emitter-follower stage, designed around transistor 448 duplicates the voltage waveform from collector 446 to provide increased current drive capability at the output connection 450. This output provides the needed synchronization pulses that initiate the cooperation among other functional blocks of the acoustical imaging operation. For instance, the output at 450 initiates the insonifying transducer acoustical pulse while providing the zero-time reference marker for the Y-direction scanning process.

Figure 22:
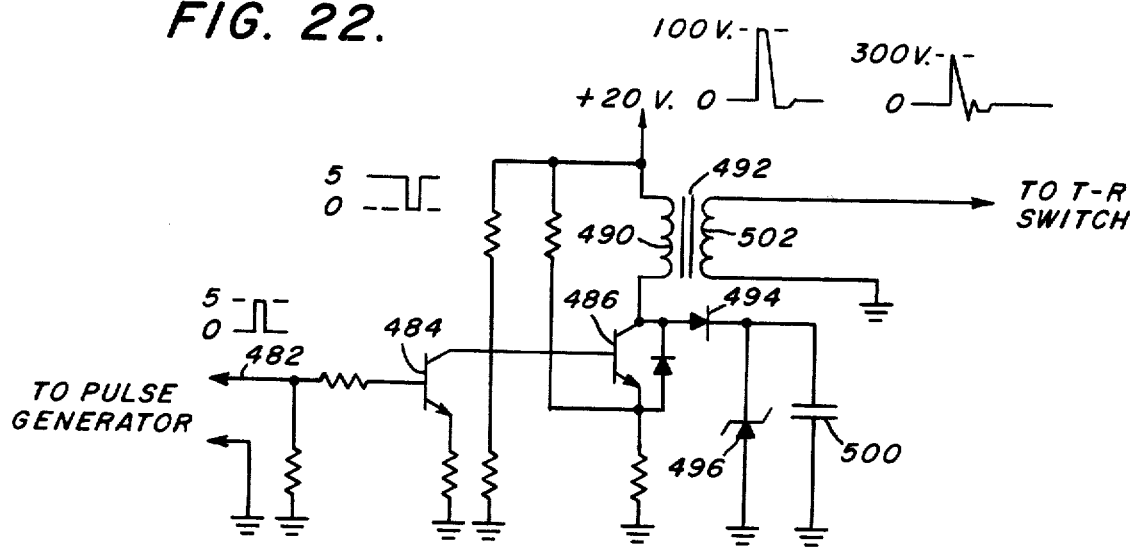
FIG. 22 illustrates a form of pulse amplifier circuit of this invention.

As is shown in FIG. 22, a preferred form of circuitry for pulse amplifier 332 which cooperates with pulse generator 330 and transmit-receive box 334 is illustrated. The amplifier illustrated is unique in that it subjects the transistor 486 to more conservative operating conditions than do conventional pulse amplifiers which usually use an avalanche-breakdown principle in transistor 486. Upon arrival of a pulse at 482 from pulse generator 330, transistor 484 is turned on thus causing transistor 486 to stop conducting. When the primary of transformer 492 stops conducting, the inductive "kick" in the primary 490 of transformer 492 attains a high voltage of 100 volts which is limited by the diode 494 and capacitor 500 to prevent transistor 486 from burning out due to possible voltage breakdown. Transformer 10 increases the primary voltage to 300 volts at secondary coil 502 and this is the voltage that goes to the transmit-receive box 334. Zener diode 496 prevents capacitor 500 from accumulating a charge above the 100 volt limit during successive pulsing action.

Figure 23:
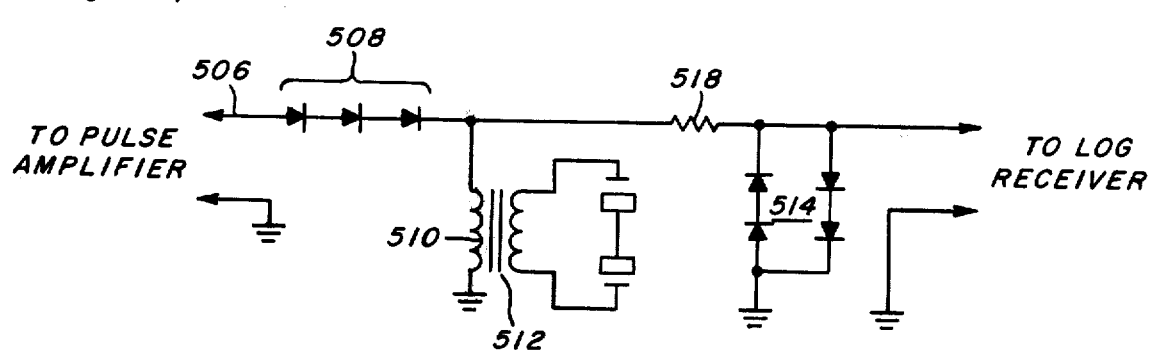
FIG. 23 illustrates a circuit diagram of a form of transmit-receive switch of tnis invention.

A specifically preferred form of transmit-receive box or switch 334 is illustrated in FIG. 23. As is shown in this figure, voltage pulses 506 are received from pulse amplifier 332 and cause diode assembly 508 to overcome the voltage drops of 0.6 volts per diode, thereby engaging the input pulse into the primary 510 of the commutation transformer 512. During this period diode network 514 prevents more than 1.5 volts from entering the region during the transmitted pulse. Resistor 518 limits the current in diode network 514 during the transmitted pulse.

Figure 24:
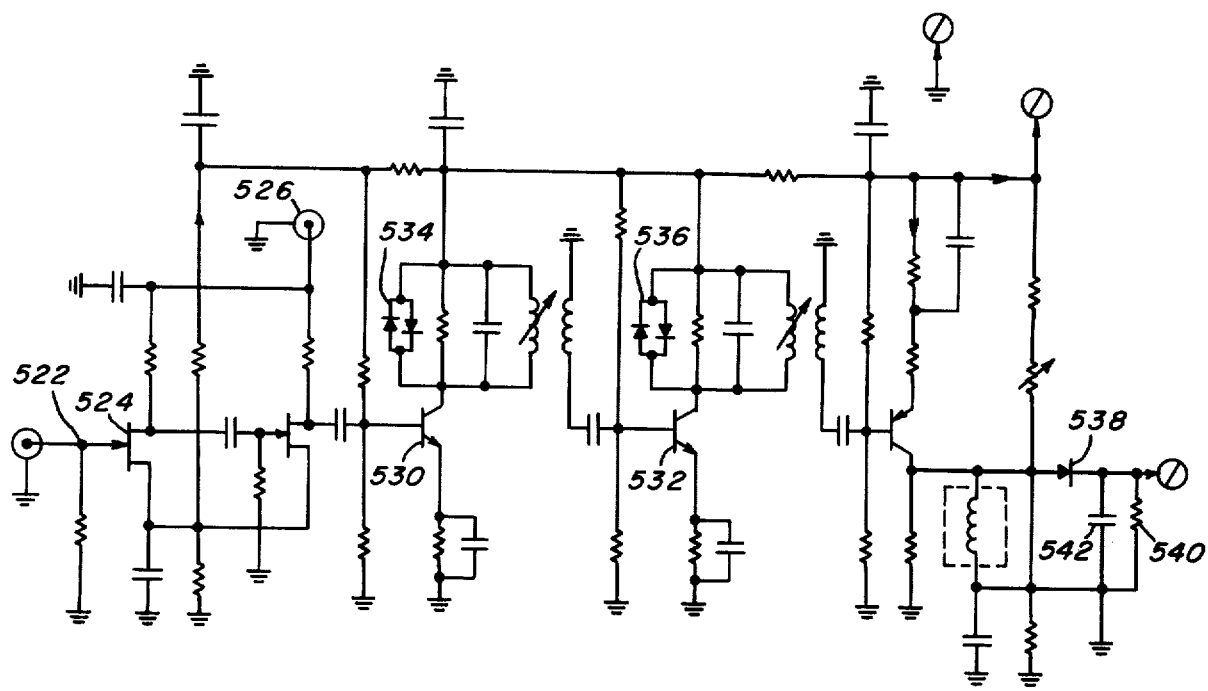
FIG. 24 illustrates a logarithmic wide band receiver suitable for use in the present invention.

Referring now to FIG. 24, a form of preferred logarithmic wide band receiver 336 is illustrated. The signal coming from the transmit-receive box 334 enters the receiver at point 522 to operate input stage field effect transistor 524. A provision for an external gain control 526 enables the receiver sensitivity to be increased as the elasped time after each acoustical pulse increases. This feature is optional, however. External gain control 526 could be connected to the Y-deflection ramp waveform to provide increasing gain with time, if desired. Transistors 530, 532 employ tuned circuits with shunting diode networks 534 and 536 limiting the amplitude signals to be proportional to the logarithm of the range of input signal voltages of approximately a 60 decibel dynamic range. The output signal is rectified by diode 538 and filtered by resistor 540 and capacitor 542 to produce the video signal that goes to the cathode-ray tube 340 in display console 26.

The logarithmic receiver 362 and video amplifier 364 may be essentially the same circuits as logarithmic receiver 336 and video amplifier 342 which have been described above.

Figure 25:
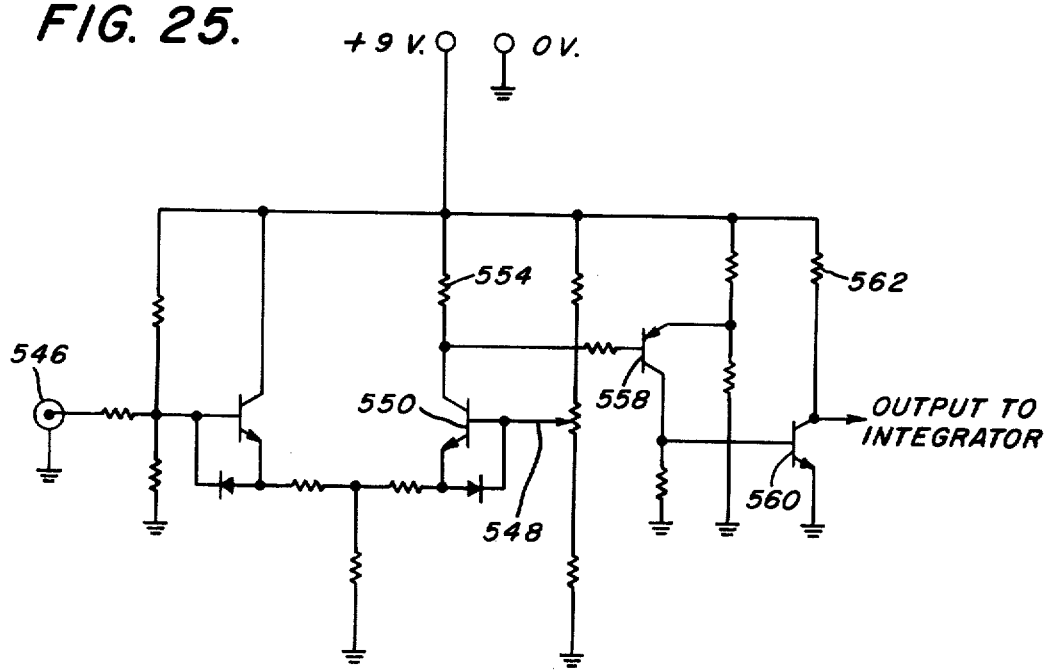
FIG. 25 illustrates a form of threshold detector which may be used in the present invention.

A form of suitable threshold detector 370 is shown in FIG. 25. Whenever video input 546 from amplifier 364 exceeds the reference voltage at point 548, transistor 550 turns off and the voltage across resistor 554 increases thereby causing transistor 558 to also turn off. Thus, the transistor 560 turns off and the voltage across resistor 562 increases and this increased voltage constitutes the trigger signal that stops the integrator 374.

Figure 26:
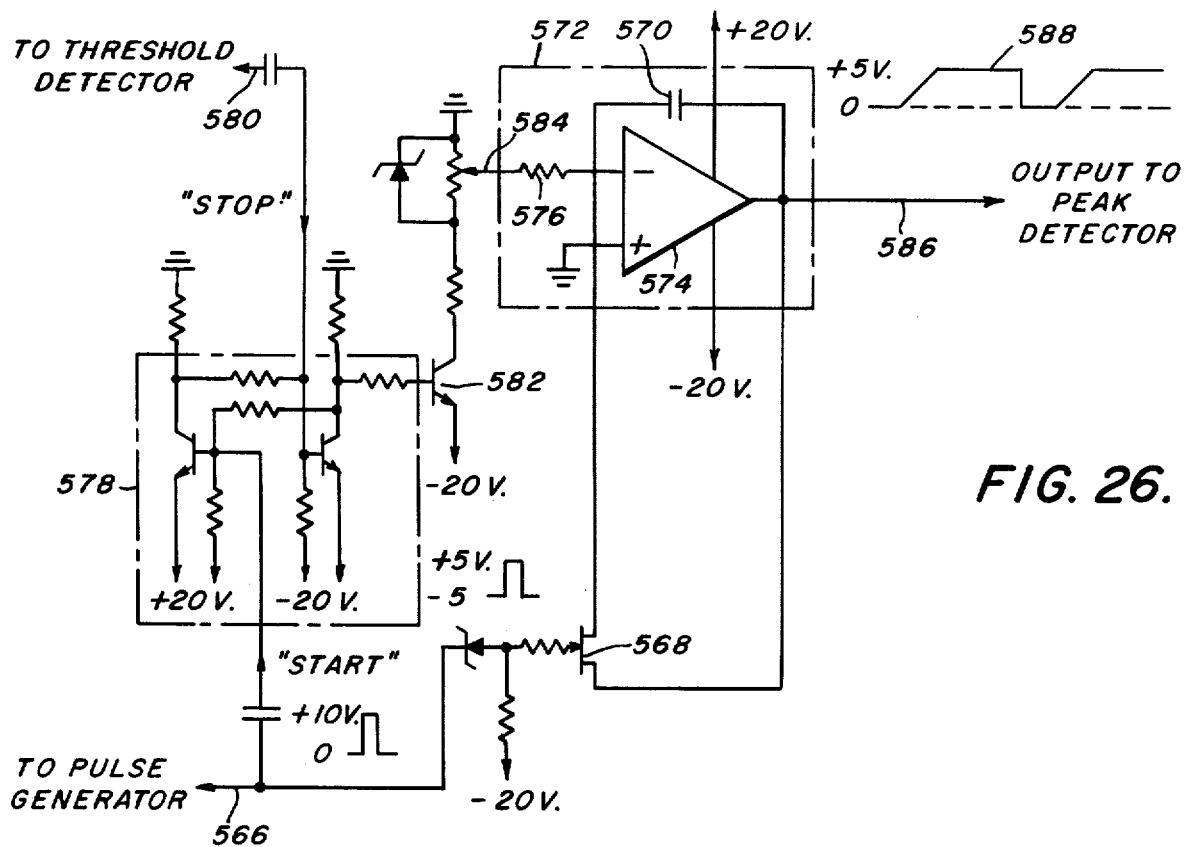
FIG. 26 illustrates a form of integrated circuit which may be employed with this invention.

Referring now to FIG. 26, a preferred form of integrator 374 is shown by way of example. Pulse 566 from the master pulse generator 330 causes field effect transistor 568 to act as a short circuit that discharges the capacitor 570 of integrator 572 which is built as the combination of capacitor 570, operational amplifier 574 and resistor 576. As a result whenever a pulse 566 arrives from the master pulse generator 330, integrator 572 has its output voltage reset to 0 volts Operational amplifier 574 could be type $\mu$A 741 CV sold by Signetics available from numerous integrated circuit manufacturers. Pulse 566 drops to 0 volts in a matter of a few microseconds and field effect transistor 568 then becomes an open circuit. However, flip-flop 578 gets "turned on" by pulse 566 and flip-flop 578 stays on until after signal 580 from the threshold detector turns flip-flop 578 to the off position. While flip-flop 578 is in the on position, transistor 582 acts as a closed switch, thereby enabling reference voltage 584 to be activated only during the on time. While this reference voltage exists, the integrator output voltage 586 of integrator 572 starts to climb from 0 to increasing values in proportion to the on time of the flip-flop 578. The final voltage 588 represents the on time and hence the physical distance to be measured back in the belt mechanism, and the sub-circuit of FIG. 26 is in fact unique because it comprises a special-purpose analog computer.

The peak detector 376 may be a simple RC time constant type of rectifier circuit. The mixers 378, 402, 406 can be built around operational amplifiers by simply adding a second resistor to the inverting input connection of such operational amplifiers, as is well known in the field of analog computation. A suitable amplifier for such use is the Signetics type $\mu$A 741 CV. The digital divide by twenty circuit 388 could be built around binary integrated circuits (such as Texas Instruments type MC 7493, for example) so that two such integrated circuits are required to reset their count whenever their count reaches twenty in binary form.

The sine and cosine generators 392, 396 may be standard slope-breakpoint function generators such as are commonly employed in analog computers. A specific suitable type is that sold under the designation Model TR-48 Analog Computer by Electronics Associates, Inc. which contains a function generator which can be programed for the sine-cosine operations discussed herein.

Figure 27:
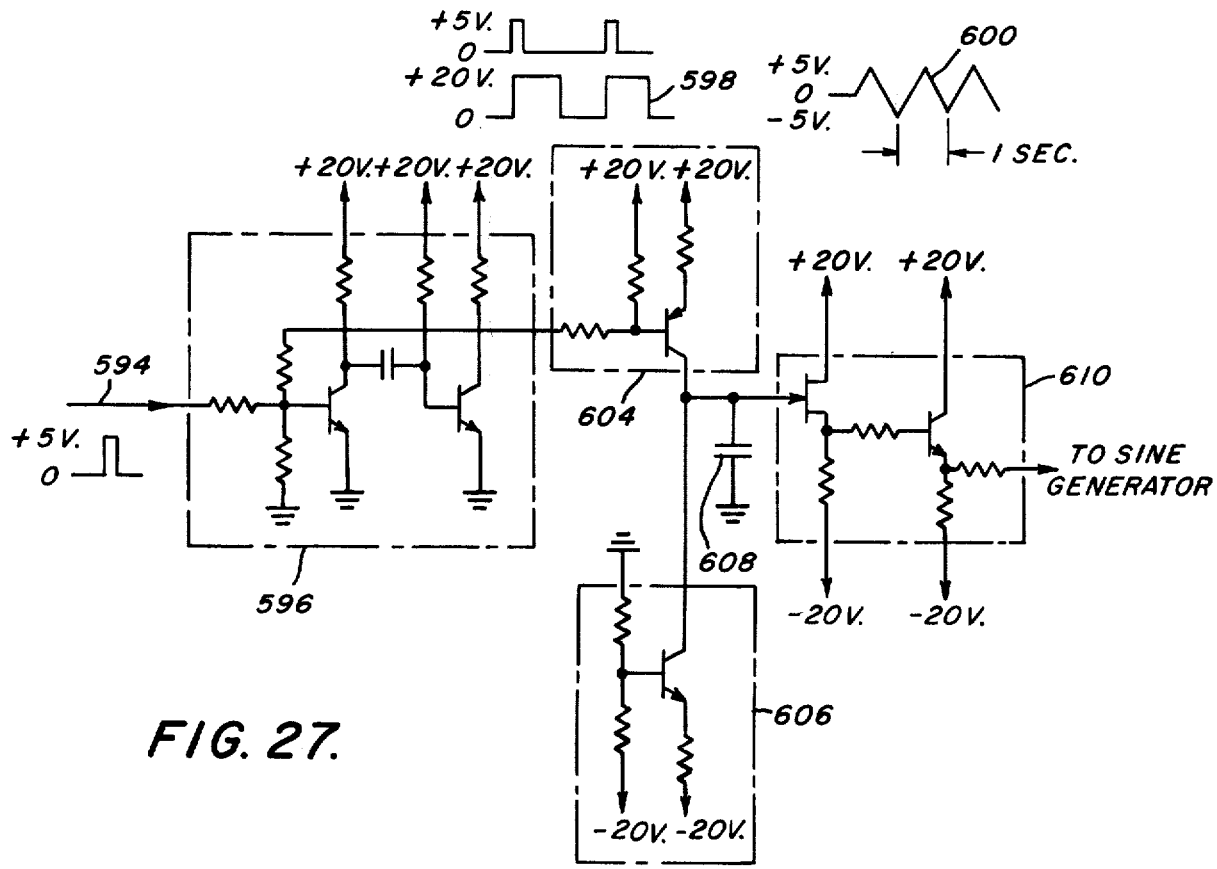
FIG. 27 illustrates a portion of the processing circuitry including a multivibrator and output amplifier for cooperation with a sine generator.

With respect to the triangular waveform or ramp generator 386, for a specific example of the "divide by 20" form used for purposes of illustration, reference is now made to FIG. 27. The trigger pulse 594 initiates 500 millisecond pulses in the one shot multivibrator unit 596. The repeated trigger pulses 594 initiate a pulse train 598 which represents a square wave. This square wave 598 intermittently turns a first current source 604 on and off. When first current source 604 is turned on, its current is twice the continuously running current from second current source 606. The fluctuating currents, cyclically repeated over a one second interval, causes the voltage across the capacitor 608 to rise and fall along a triangular waveform 600, which is then amplified at 610 before being passed to operational sine generator 392.

Figure 28:
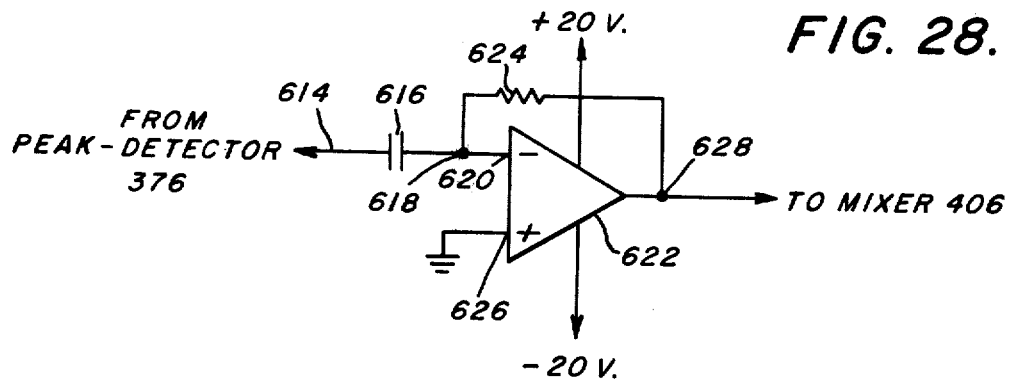
FIG. 28 illustrates a form of derivative function means which may be employed in the present invention.

The derivative function 404 shown in FIG. 20 could be built around a conventional operational amplifier, such as Signetics type $\mu$A 741 CV, for example, by using the circuit illustrated in FIG. 28, if desired. The voltage waveform from peak detector 376 at 614 passes through capacitor 616. The other connection 618 of capacitor 616 terminates at the null-junction 620 (the inverting input) of operational amplifier 622. Meanwhile, the output signal from the operational amplifier 622 is fed back through resistor 624 to the null-junction 620. Since the amplification factor of operational amplifiers are typically of the order of 100,000 times the difference voltage between points 620 and 626, substantial signal voltages are obtained at output 628 while null-junction 620 remains essentially at ground potential (zero volts). Since the current in capacitor 616 is proportional to the time rate-of-change of applied voltage from peak detector 376, the current through resistor 624 must approximately equal the capacitor current. However, the current through resistor 624 also corresponds to the output voltage at 628. As a result, the output voltage value at 628 corresponds to the time rate-of-change of the original input voltage 614. Such a differentiated output voltage is delivered to mixer 406. This differentiated voltage provides information about the tilting action of the scanning transducers when the scanner 2 bends to conform to the shape of the test specimen.

In the embodiment illustrated in FIGS. 1 through 28, only one transducer 62, 64 actively retrieves acoustical data from the test specimen at any given time. As alternate scans occur among the two transducers 62, 64, the paired scans need not lead to displayed scanning lines that overlap from scan to scan. If such overlap does not occur, then the effective number of scanning lines is doubled, resulting in a more detailed acoustical image. In order to cause a second scan not to effectively overlap with a first scan, a slight non-uniformity of spacing may be introduced between transducers 62, 64, i.e., the circumferential distance between transducers in one direction will be very slightly greater than the distance between the transducers 62, 64 circumferentially in the opposite direction. As pulse generator 330 may operate at 1000 pulses per second, for example, and the endless belt 60 may scan a 10 inch sweep across the test specimen in 1/10 of a second (100 milliseconds), for example, the timing adjustment needed to produce interlacing action (500 microseconds) corresponds to a space mis-alignment of 0.05 inch between transducers 62, 64. This results in a belt having a circumference of 24 inches in measured distance between centers of transducers being 12.025 inches in one direction and 11.975 inches in the other direction. The spacing between transducers 62, 64 shall be deemed "generally equal" for purposes of this embodiment in spite of minor differences effected to create such interlacing action. The spacing between magnets 68, 70 and the adjacent transducers 62, 64 should be maintained substantially identical as the X-motion scan is initiated when the transducers 62, 64 are at their precise start positions.

Second Embodiment (FIGS. 29 Through 43)

Figure 29:
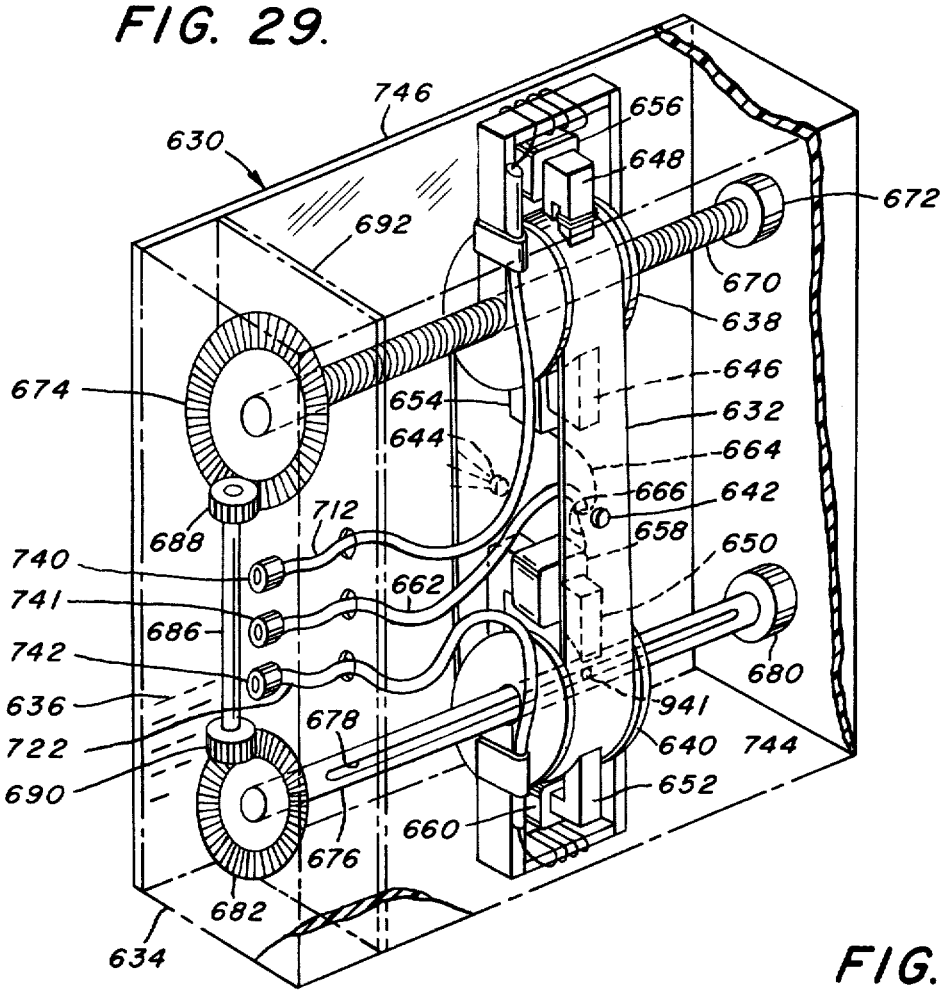
FIG. 29 is a partially schematic view of a second embodiment of the scanner of the present invention.

Referring now to FIG. 29, there is shown a modified form of integrated scanner 630 which is adapted for use in through-transmission ultrasonic testing. This embodiment is similar in certain respects to the first embodiment described above in that an endless belt 632 is secured within a sealed enclosure 634 which contains an acoustically conductive liquid 636. The endless belt is mounted over a pair of pulleys 638, 640 at least one of which is driven by an electrical motor wherein the pulley 638, 640 serves as the rotor thereof. In this fashion orbital movement of the endless belt 632 is established.

A transducer 642 is secured to the endless belt as is a light emitting diode 644 with the circumferential spacing between the transducer 642 and the light emitting diode 644 preferably being substantially equal regardless of direction in which the measurement is taken along the belt 632. Stators 646 and 648 cooperate with pulley 638 to create an electric motor for driving the belt 632. Similarly, stators 650, 652 cooperate with pulley to create an electrical motor. Brackets similar to those shown with the reference designation 84 in FIGS. 8 and 9 may be employed in this embodiment, but have been deleted from FIG. 29 in the interest of simplicity of illustration. Stators 646, 648, 650, 652 have, respectively, field windings 654, 656, 658, 660. Electrical cable 662 which is in electrical contact with connector 741 which in turn is in electrical contact with the exterior of the sealed housing 634 through cable means (not shown in this view) provides energy for the field windings 654, 656, 658, 660. Conductor 664 connects cable 662 with field winding 654. Conductor 666 connects conductor 662 with field winding 658. Electrical connections (not shown) connect field winding 654 with field winding 656 and field winding 658 with field winding 660.

The embodiment illustrated in FIG. 29 contemplates not only orbital movement of the transducer 642 and light emitting diode 644 which are mounted on endless belt 632, but also that the belt 632 will be subjected to translational movement, in a direction generally perpendicular to the direction of the orbit of the belt 632. To accomplish this, a first pulley shaft 670 is exteriorly threaded and has one end rotatably secured within journal 672 and the other end fixedly secured to gear 674. Pulley 638 is threadedly engaged with first pulley shaft 670 such that relative rotation therebetween will cause longitudinal movement of the pulley 638 along the first pulley shaft 670.

Second pulley shaft 676 is provided with an elongated slot 678 and the pulley 640 is so configurated with an internal pawl 941 as to rotate with rotating second pulley shaft 676. The second pulley shaft 676 has one end rotatably secured within journal 680 and has gear 682 fixedly secured to the other end. Shaft 686 which is secured in rotatable position by means not shown has gear 688 fixedly secured thereto and has teeth in engagement with teeth of gear 674. Similarly, gear 690 is secured at the lower extremity of shaft 686 and teeth engaged with teeth of gear 682. As a result of this arrangement, operation of the motor of which pulley 640 forms a part will cause rotation of the pulley 640 which in turn causes responsive rotation of second pulley shaft 676 and gear 682. Rotation of gear 682 results in gear 690 transmitting the rotational movement to gear 688 through shaft 686 with the result that gear 674 rotates creating responsive rotation in first pulley shaft 670, thereby subjecting the pulleys 638, 640 to translational movement along the pulley shafts 670, 676. It will be appreciated that once translation has been effected in a first direction to the limit of travel permitted by the mechanical system reversal of the direction of rotation of the pulleys 638, 640 will result in translation of the endless belt-pulley assembly in the opposite direction.

It will be appreciated that upper pulley shaft 670 serves both as a lead screw and as a bearing member.

In one preferred form of this embodiment, gear 674 will be slightly larger than gear 682 such that gear 674 will rotate at approximately 80% of the angular velocity of lower pulley 640. Because of the slightly lower angular velocity of the upper pulley 638, the screw advancement action occurs much more slowly than if pulley 638 rotated on a stationary screw-threaded shaft. The net effect is to achieve the translational motion expected of a screw thread with a much finer thread pitch. Divider wall 692 has openings through which pulley shafts 670, 676 pass and serve as journals therefor.

Referring now to FIGS. 29 and 34, the non-contacting commutation means of this embodiment will be considered. As is shown in FIG. 34, a spacer member 694 is secured by fastener means 696 to stator 650 and by fastener 698 to stator 646. This form of spacer serves to preserve the position of the stators 646, 650 with respect to each other and may conveniently take the form of non-corrosive bar or sheet-like elements having securement flanges 697, 699. A preferred material for this use is extruded nylon or Debrin.

Endless commutator spring 700 which may be a phosphor bronze spring such as has been disclosed in connection with the previous embodiment is secured to endless belt 632 which has not been illustrated in FIG. 34 and provides a series electrical connection between receiving transducer 642 and light emitting diode 644.

An upper magnetic commutation loop is provided by pulley shaft 670 which may conveniently be a ferite rod in combination with side magnetically conductive members 702, 704 and upper magnetic member 706. A suitable material is that manufactured by Magnetics, Inc. and sold under the trade designation Type A Manganese-Zinc Ferrite material. Electrical cable 712 is in electrical contact with cable means (not shown) which are disposed exteriorly of the sealed housing and energize electrical coil 714 which is wound around upper magnetic member 706 by means of wire 710. A Faraday shield 716 which may conveniently consist of thin copper foil is in protective surrounding relationship positioned adjacent coil 714. Similarly, a lower magnetic loop is energized through cable 722 which is in electrical continuity with coil 724 through conductor 726. Faraday shield 728 surrounds the coil. The lower magnetic loop is defined by slotted ferrite pulley shaft 676 in combination with side magnetic members 734, 736 and lower magnetic member 738.

Commutation spring 700, which is secured on endless belt 632, is magnetically coupled with the upper and lower magnetic loops. Acoustical waves impinging upon receiving transducer 642 are converted into acoustical function electrical signals in the form of pulses on commutation spring 700. These current pulses set up a magnetic field in the upper magnetic loop consisting of elements 670, 702, 704, 706, all of which are preferably fabricated from ferrite antenna material of a thickness of about 0.2 to 0.5 inch. Coil 714 then converts these currents into voltages that travel along conductor 710 to electrical cable 712 to connector 740 which is in communication with cable means (not shown) disposed exteriorly of the sealed housing. The cable means put out a signal which travels to external signal processing means. Such voltages are electrically converted exteriorly of the sealed housing into meaningful pictorial signals which signals arrive from the external signal processing means into connector 742 from cable means (not shown) and travel along cable 722 into the lower magnetic loop which consists of elements 676, 734, 736 and 738 and establish magnetic fields in the lower magnetic loop. These fields are picked up by commutation spring 700 and serve to energize light emitting diode 644.

In a preferred form of the invention, the liquid tight sealed enclosure 634 will be fabricated out of a suitable rigid material. For example, a 1/16 inch thick rigid vinyl sheet might be employed. A front wall 744 is preferably acoustically transparent but optically opaque. If desired, the front wall 744 may be mechanically compliant so as to assume complementary relationship with respect to the test specimen. The rear wall 746 is preferably fabricated out of an optically transparent material such as a clear Lucite, for example. (For clarity of illustration the enclosure 634 has been shown as being transparent.)

The light emitting diode 644 may preferably have a convex converging lens that focuses the light output from the light emitting diode on a plane approximately ⅜ to ¾ inch from the rear surface of endless belt 632. It is contemplated that in order to obtain a photographic record of the light emitting diode responses to acoustical energy received by transducer 642, a camera or other photographic record making means would be positioned rearwardly of the sealed enclosure 634 so as to record through the optically transparent rear wall 746.

Referring now to FIG. 30, there is shown a test specimen 750 in the form of a human arm. Insonifying transducer 752 is positioned on one side of the test specimen 750 and the scanner 630 is positioned on the other side. In this embodiment the front wall 754 of the scanner 630 is mechanically compliant so as to assume a complementary relationship with respect to the contour of the test specimen 750. A photographic record making means 756 which in the form shown is a plate/film-/holder (such as that sold by Polaroid) is positioned immediately rearwardly of the scanner 630 so as to permit making of a photographic image of the scanned raster imaging format from light emitting diode 644. External electronic box 760 is positioned closely adjacent to the environment of use. In addition to containing the external signal processing means which will be described below, box 760 is connected by cable 762 to insonifying transducer 752 in order to energize the same. Similarly, cable means 764 connects the external signal processing means with scanner 630.

It is noted that the scanner 630 is of relatively small dimension and is readily manually supported by the operator and the electronic box 760 is also relatively small and readily supported. As a result, the equipment of the present invention is adapted for ready manual support by the operator and high portability so as to permit ultrasonic testing in a wide range of physical environments. If desired, scanner 630 could be so designed as to have electronic box 760 secured to the exterior thereof.

In operation, the system of FIG. 30 has the external signal processing means within box 760 and includes a power supply for supplying high voltage electrical pulses to insonifying transducer 752. The acoustical wave emitted by transducer 752 passes through the test specimen 750 and is received by the transducer 642 which in turn sends acoustical function electrical signals in the form of voltages through the processing equipment to illuminate light emitting diode 644. The photographic record making means positioned at the rear of the scanner 630 exteriorly of the sealed housing may conveniently be a 35 millimeter camera, a camera containing means for developing a picture of the photographically recorded images of the light emitting diode, another type of camera or merely a film plate holder of the type distributed under the trademark Polaroid Type 57 film holder.

In connection with the avoidance of undesired immersion techniques with portions of the human body such as the female breast, reference is made to FIG. 31 wherein a block of acoustically conductive material, such as silicone rubber, vinylsols or plastisols, for example, which can be molded to the general shape of the specimen is provided. A suitable silicone rubber is that sold under the trade designation Type 615 RTV Rubber by General Electric. Molded polyvinyl-chloride would also be a suitable material. The acoustically conductive block 782 receives breast 780 within recess 784. By means of suction hole 786 a tube 788 is connected to vacuum pump 790 and the interior of block 782. An acoustical couplant such as grease is applied to the breast and the breast introduced into the block recess 784. The suction results in the creation of a mild partial vacuum and intimate acoustical coupling contact between the specimen and block recess 784. As a result of the intimate acoustical bond between the breast 780 and the block 782, effective acoustical transmission may be effected through block 782. Block 782, in essence, creates the equivalent of the liquid tank without burdens of the same. Further, silicone rubber communicates pressure (dilatational) ultrasonic waves at approximately 7/10 of the velocity of sound in breast tissues providing an efficient means of transmitting such waves, but cannot transmit shear acoustical waves. As a result, block 782 is acoustically effective.

Referring now to FIG. 32, an adaption of the concept described in the context of FIG. 31 in connection with the scanner of the present invention is considered. A female breast 794 is received within recess 796 of specimen retaining block 798. Insonifying transducer 800 is secured to one end of block 798 and scanner 630 is in contact with the other end thereof. Vacuum pump 806 evacuates the recess 796 and produces intimate acoustical contact between block 798 and breast 794. Photographic record making means, which in this instance is a film holder, is positioned adjacent to the rear face of scanner 630. External signal processing means are disposed in box 810 and energizes transducer 800 through cable 812 and also energizes the scanner 630 through cable 814.

A modification of the construction shown in FIG. 32 is shown in FIG. 33 wherein the apparatus is adapted for taking of ultrasonic readings at a wide range of angles with respect to the test specimen.

In this embodiment of the invention the patient is wearing an annular acoustically conductive block 820 which has a circular exterior surface 822. For convenience of securement, in the form shown, the block 820 is formed as part of a brassiere type structure 826. Vacuum is drawn by means of vacuum pump 830. The insonifying transducer 834 is energized from electronics box 810 through electrical cable 812 while the scanner 630 is energized through electrical cable 814. It is noted that the scanner has a generally curved configuration which is substantially complementary with respect to the exterior surface 822 of block 820. Camera means 836 also is of complementary curved configuration and is mounted on the rear of scanner 630. For convenience of establishing relative rotational movement while maintaining the generally diametrically opposed relationship between insonifying transducer 834 and scanner 630, both elements are mounted upon a ring-like outer member 840 which is concentric with block 820 and mounted for relative rotational movement therewith while maintaining good acoustical coupling therebetween. Vacuum pump 830 could conveniently be energized by an additional cable means (not shown) similar to cable 814. This embodiment provides the distinct and substantial advantage of permitting through-transmission images of the test specimen from a number of orientation angles in a very simple and rapid manner. In order to maintain the desired acoustical coupling, the region between the outer surface 822 of the block 820 and the inner surface of outer ring 840 should contain an acoustical couplant. Also, the outer surface 842 of ring 840 should preferably contain an acoustical couplant to acoustically engage scanner 630 and the transducer assembly 834.

Figure 35:
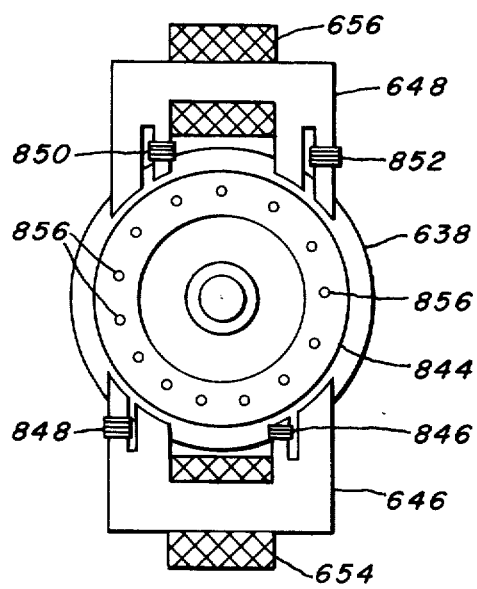
FIG. 35 is a cross sectional illustration showing a portion of the drive motor employed in the embodiment of FIG. 29.

Referring now to FIG. 35, there is shown a cross sectional illustration of the upper motor. It is noted that the pulley 638 may be conveniently formed of plastic such as molded nylon. The squirrel cage rotor 844 contains a plurality of shorting bars 856 which are typical of the squirrel cage rotor design of alternating current induction motors. The rotor 844 may be formed separately and joined to pulley 638 or the pulley 638 may be impregnated in the plastic material during the plastic molding process. As is shown also in FIG. 35, the stator 648 is provided with shorting bars 850 and 852, and stator 646 is provided with shorting bars 846 and 848.

Figure 36:
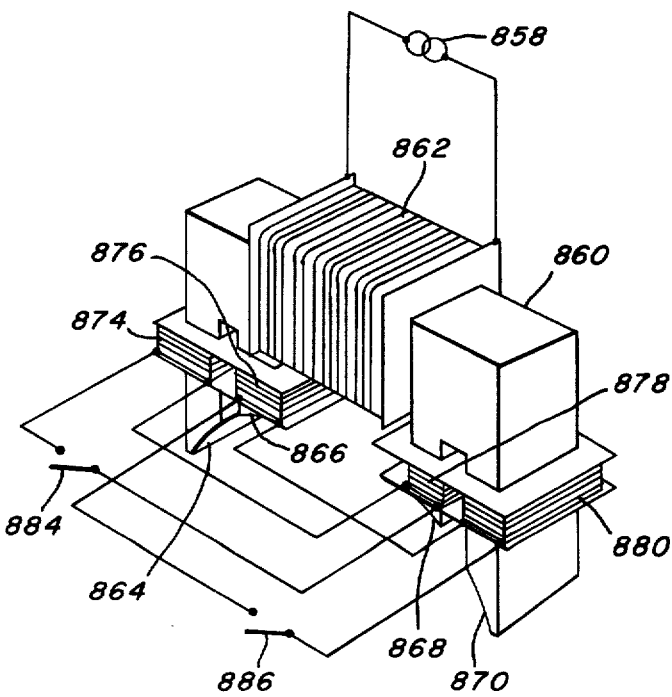
FIG. 36 is a modified form of drive motor adapted for use with this invention.

Referring now to FIG. 36, there is shown a modified form of stator which may be employed in this invention, for example, in lieu of the form of stator 648, 646 shown in FIG. 35. In this form of stator, an AC power source 858 excites coil 862 which sets up magnetic field in pole pieces 864, 866, 868, 870. Tertiary coils 874, 876, 878, 880 act as shorting bars when such coils are short circuited in pairs by action of either first switch 884 or second switch 886. It is noted that first switch 884 acts as a switch control on a closed loop connecting tertiary coils 874 and 878 and second switch 886 acts as a switch control over a closed circuit loop connecting tertiary coils 876 and 880. If coils 874 and 878 are short circuited, then poles 864 and 868 will have a magnetic field that lags 90° behind the magnetic field in poles 866 and 870, respectively. If, however, the alternate tertiary coils 876 and 880 are short circuited, then the sense of magnetic field delay pattern will become reversed. For each short circuit choice selected by switches 884 and 886, an equivalent of a rotating magnetic field is set up and the direction of said rotation reverses depending upon which switch is closed. The stator 860 is placed in close proximity with a squirrel cage rotor within a pulley and a rotating magnetic field is produced upon the pulley in a direction that depends upon whether switch 884 or switch 886 is closed. This type of convenience in motor direction reversal is important because this reversal permits the translational movement of the scanner 630 in a first direction and subsequently in a second direction with reversal of direction being controlled by such switching.

Figure 38:
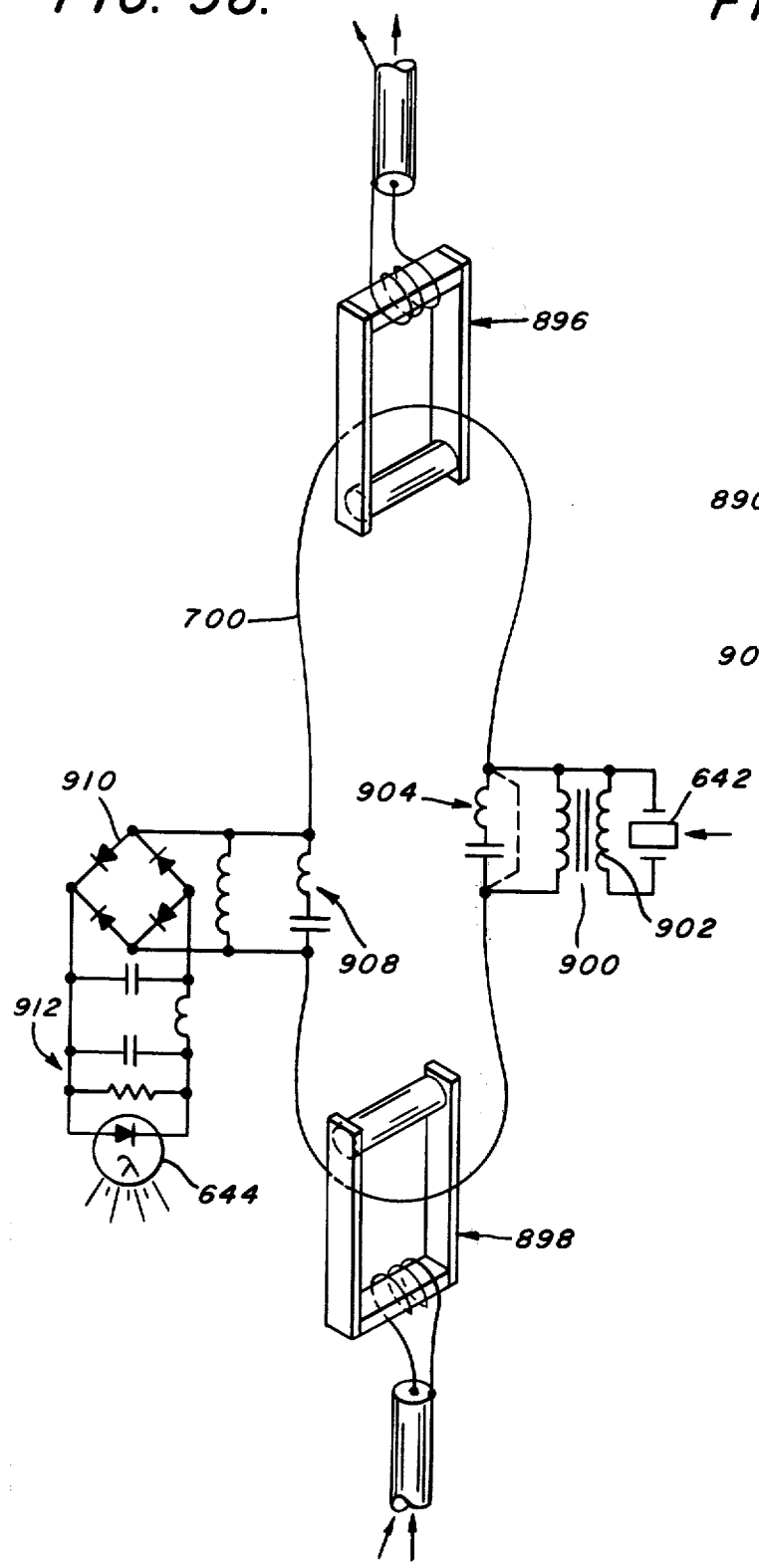
FIG. 38 is a circuit diagram showing electrical portions of the belt of FIG. 37 and portions of the commutation means.

Referring now to FIG. 37, there is shown the endless belt 632 to which are secured the receiving transducer 642 and light emitting diode 644 which are electrically connected in series through commutation spring 700 and transducer electronics unit 890 and diode electronics unit 892. The details of the transducer electronics unit 890 and light emitting diode electronics unit 892 are shown in FIG. 38 wherein the commutation spring 700 is indicated schematically passing through upper commutation transformer 896 and lower commutation transformer 898. The receiving transducer 642, which may be of the type marketed under the trade designation Glenite Type 2D3 Disc transducer, is connected to stepdown transformer 900 that has a shunt inductance referred to the primary 902 of about 200 microhenries, for example, and a turn ratio of about 10 to 1, for example. Secondary transformer 900 is connected across series resonant circuit 904 and is designed to prevent high frequency radio frequency current (at about 50 megahertz) used to operate light emitting diode 644 from interfering with operation of receiving transducer 642. A similar series resonant circuit (working at about 3 megahertz, for example) 908 is connected across the light emitting diode circuit to prevent interference by the transducer signal. Upper commutation transformer 896 receives acoustical function electrical signals at about 3 megahertz, for example, from the currents in commutation spring 700 or the lower commutation transformer 898 sends light emitting diode 644 power at about 50 megahertz, for example, into the same phosphor bronze commutation spring 700. The diode power passes into rectifier 910 and the output from this rectifier 910 goes into low pass filter 912 (direct current to about 100 kilohertz, for example) and the output of filter 912 operates light emitting diode 644. The rectifier bridge 910 may typically be comprised of 4 germanium diodes of Type 1N541, for example, and the light emitting diode 644 might be of the type sold by Motorola under the trade designation MLED 600.

Figure 39:
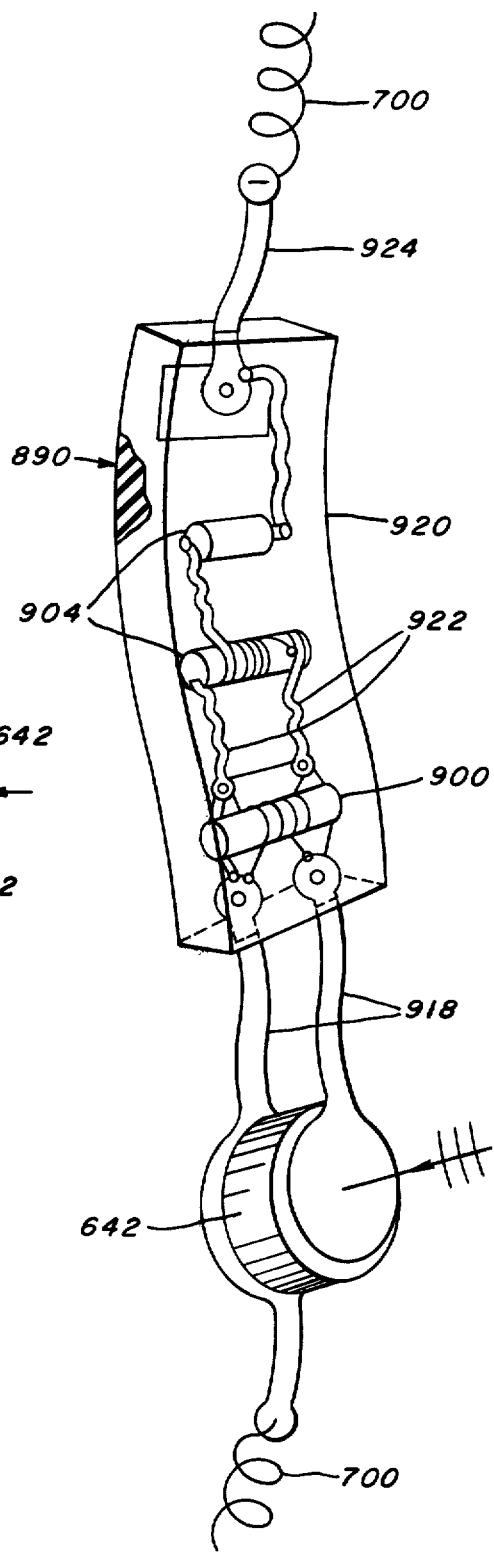
FIG. 39 is a partially schematic detail of a part of the electronic connection of the endless belt of FIG. 37.

In view of the desirability of having mechanically compliant electrical connections which will endure repeated cycles of severe bending over the pulleys 638, 640 during routine orbital and translational movement of the belt, a preferred approach to such joints has been created. Referring now to FIG. 39, there is shown by way of an example the transducer electronics unit 890 which in the form shown is contained within a resilient box 920 which is preferably of molded silicone rubber such as the material marketed under the designation Type 630 RTV silicone rubber manufactured by General Electric. The connection between transducer 642 and transducer electronics unit 890 is effected by means of conductive foil strips 918 which are preferably of relatively thin (about 0.001 to 0.003 inch) phosphor bronze or beryllium copper foil. These connectors pass through a wall of resilient box 920 and are electrically connected to transformer 900. At the other end of the transducer electronics unit 890, a similar connector 924 is used to connect with commutation spring 700. In order to eliminate the less desirable flexible copper wires and the like which will not withstand as many millions of flexural deformation cycles as will other connectors, it is preferred to replace such flexible copper wires with a miniature corrugated spring 922 such as those shown connecting the transformer 900 with resonant circuit 904. Such springs may preferably be composed of material of about 0.001 to 0.003 inch thickness and having a peak to peak bending amplitude of about 0.040 to 0.060 inch. A similar approach to resilient and durable electronics connections may be employed with the diode electronics unit 892.

Referring now to FIG. 40, a discussion of external signal processing means employed to communicate with and energize the scanner 630 will now be considered. As is shown in FIG. 40, a pulse generator 930 emits a signal to pulse amplifier 932 which in turn energizes insonifying transducer 934. The acoustical wave emitted by insonifying transducer 934 will pass through test specimen 936 which is in contact with resilient wall 938 of scanner 630 which contains receiving transducer 642. Disposed rearwardly of the scanner 630 is a photographic means 640 for recording the emissions of light emitting diode 644. In this instance, the photographic means 640 is shown as being a photographic film holder. Most of the external signal processing means will be housed within electronics box 810 shown in FIG. 33, for example. By way of example, it should be noted that pulse amplifier 932 will emit a pulse at about 300 volts positive going.

In operation, the acoustical function electrical signals correspond to acoustical imaging information and are commutated at upper commutation means 896 to send acoustical function electrical signals to band reject filter 942 which restricts the light emitting diode signals from entering logarithmic receiver 944. The output of logarithmic receiver 944 is quenched until the time delay generator 946 indicates that it is permissible to pass acoustical function electrical signals (generally this occurs after about a 100 microsecond delay) that do correspond to the imaging wave signals and not to spurious acoustical reverberations in the equipment or in the test specimen. Once the output of receiver 944 is screened by linear gate 948 as triggered by time delay generator 946, the output voltages so screened are peak detected by peak detector 952 and these peak values determine the actual intensity of light emitting diode 644 illumination. This intensity control is accomplished by controlling the amplitude of a radio frequency oscillator 956 by modulator 958 under command of peak detector 952. This modulated radio frequency signal is then boosted in strength by radio frequency power amplifier 962 to excite currents in commutation spring 700 which then causes responsive light emitting diode 644 illumination in proportion to the signal intensity from amplifier 962 which signal represents the logarithm of the acoustical signal amplitude received through the test specimen. When the operator pushes button 968 the scan time timer 970 renders the diagnostic system operational for a given period of, for example, 10 seconds. During this time the radio frequency oscillator 956 is turned on, thus activating light emitting diode 644. Also, during this time, an audio frequency oscillator 972 is turned on, thus activating audio frequency amplifier 976 and belt motors 980. As the entire diagnostic system is intended to be portable, a convenient recharger 982 is adapted by means of AC line plug 986 to recharge battery pack 984 that powers the diagnostic system. The battery pack 984 may conveniently be rechargeable nickel cadmium batteries.

While those skilled in the art will readily be able to employ the proper components for the various elements illustrated in FIG. 40 and a great number of those components have already been described in detail and have been the subject of illustrative examples with respect to the first embodiment, a couple of additional specific components will be considered by way of an example at this juncture. It is preferred that the modulator 958 be a wide band multiplier which has the following characteristics:

modulation capability 85–100%
modulation bandwidth DC to 100 KHz
carrier frequency 30–70 MHz tunable
input carrier power 0.1–1 watt
input modulation control voltage 0 to +5 volts DC A suitable specific integrated circuit for use in such location is Signetics type SIG 2402 T wide band multiplier.

Referring to FIG. 41, there is shown a form of linear gate 996 which is suitable for use in the present invention. The linear gate is preferably a field effect transistor that is activated to become a short circuit when it is desired to prevent signals from passing through to peak detector 952. The incoming signal at 992 from logarithmic receiver 944 passes through resistor 994. Field-effect transistor 996 shunts the signal from resistor 994, thereby preventing its passage at point 998, whenever the control signal at 1000 becomes positive by more than +10 volts, for example. Zener diode 1002 offsets the DC level of this control signal to a more negative voltage in order to turn transistor 996 "on" and "off" most effectively. Resistor 1004 keeps the zener diode 1002 always conducting, whether the control signal is zero or +10 volts.

Figures 42, 43:
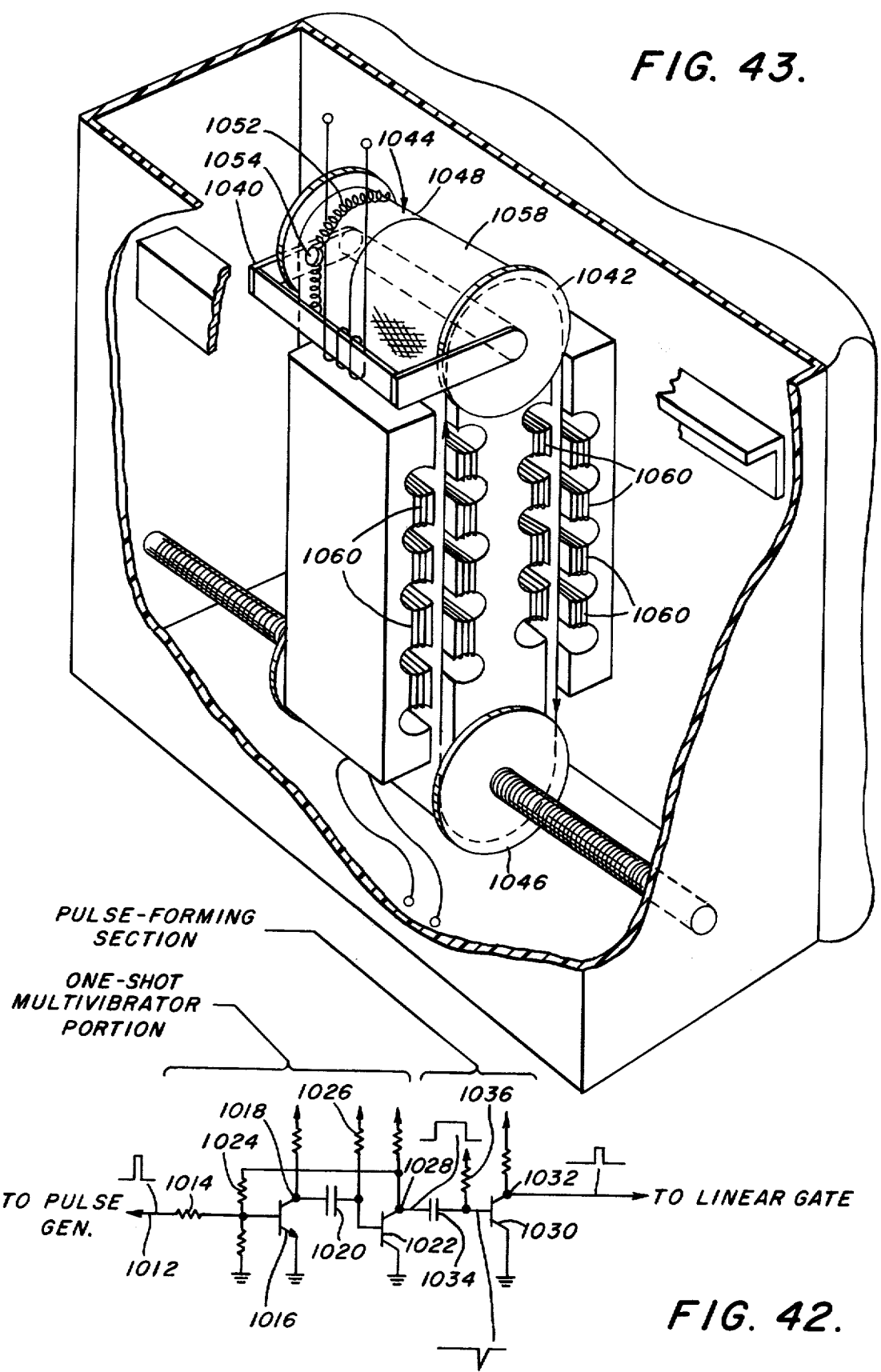
FIG. 42 is a circuit diagram of a time delay generator adapted for use in the block diagram of FIG. 40.
FIG. 43 shows a modified form of belt drive means adapted for use in the embodiment of FIG. 29.

The time delay generator 946 could consist, for example, of a one shot multivibrator with a pulse-forming circuit that operates on the tail end of the pulse from the one shot circuit, thereby causing a time delay equal to the length of the one shot pulse. An example of such a circuit is illustrated in FIG. 42. The trigger signal at 1012 coming from the pulse generator 930 passes through resistor 1014 to cause transistor 1016 to turn on, thus acting as a saturated switch. The voltage of collector 1018 swings sharply negative, thus causing capacitor 1020 to become negative with respect to ground potential, thereby turning transistor 1022 off. Such a turn-off action is fed back through resistor 1024 to sustain transistor 1016 on after cessation of the trigger signal at 1012. After a duration in time of about 100 microseconds, for example, resistor 1026 discharges capacitor 1020, and both transistor potentials return to their pretriggered values. In particular, the later fall of collector voltage at 1028 causes a momentary negative voltage pulse to occur at the base of transistor 1030, causing this transistor to momentarily turn off at the end of the pulse coming from the one shot multivibrator. Thus, collector 1032 of transistor 1030 becomes positive momentarily, and such a positive-going collector voltage becomes the control pulse to the linear gate. The actual time that the linear gate remains "on" is determined by the component values of capacitor 1034 and resistor 1036.

The scan time timer 970 (FIG. 40) may simply be the one shot multivibrator portion of the type shown in FIG. 42 in which circuit elements are suitably proportioned to cause the on-time available at point 1028 to last several seconds after a trigger voltage is applied through the operator's push button 968. The push button would be connected between a suitable battery voltage and resistor 1014.

Referring now to FIG. 43, there is shown an alternate method of propelling the endless belt of this embodiment. In this embodiment, there is shown a non-contacting commutation loop 1040 associated with upper pulley 1042. Endless belt 1044 is secured between upper pulley 1042 and lower pulley 1046. The endless belt has a non-conductive portion 1048 which contains the commutation spring 1052, receiving transducer 1054 and light emitting diode (not shown in this view). The other portion of the belt 1044 consists of a woven conductive endless portion 1058. This conductive portion 1058 may consist of a combination of metal and fabric woven threads so assembled as to create an electrically conductive sheet. Conductive endless sheet 1058 is placed between four sets of interlacing or staggered magnet structures 1060 of a linear induction motor. These magnet structures are driven by a low frequency alternating current (for example, about 60 hertz) to cause an upward magnetic field in the direction of the upwardly facing arrow and a downwardly traveling magnetic field in the direction of the downwardly facing arrow. These traveling magnetic fields drag the conductive portion 1058 of the endless belt 1044 along with the magnetic fields in a manner quite similar to the way an ordinary watt-hour meter drives the aluminum rotor plate.

Figure 44:
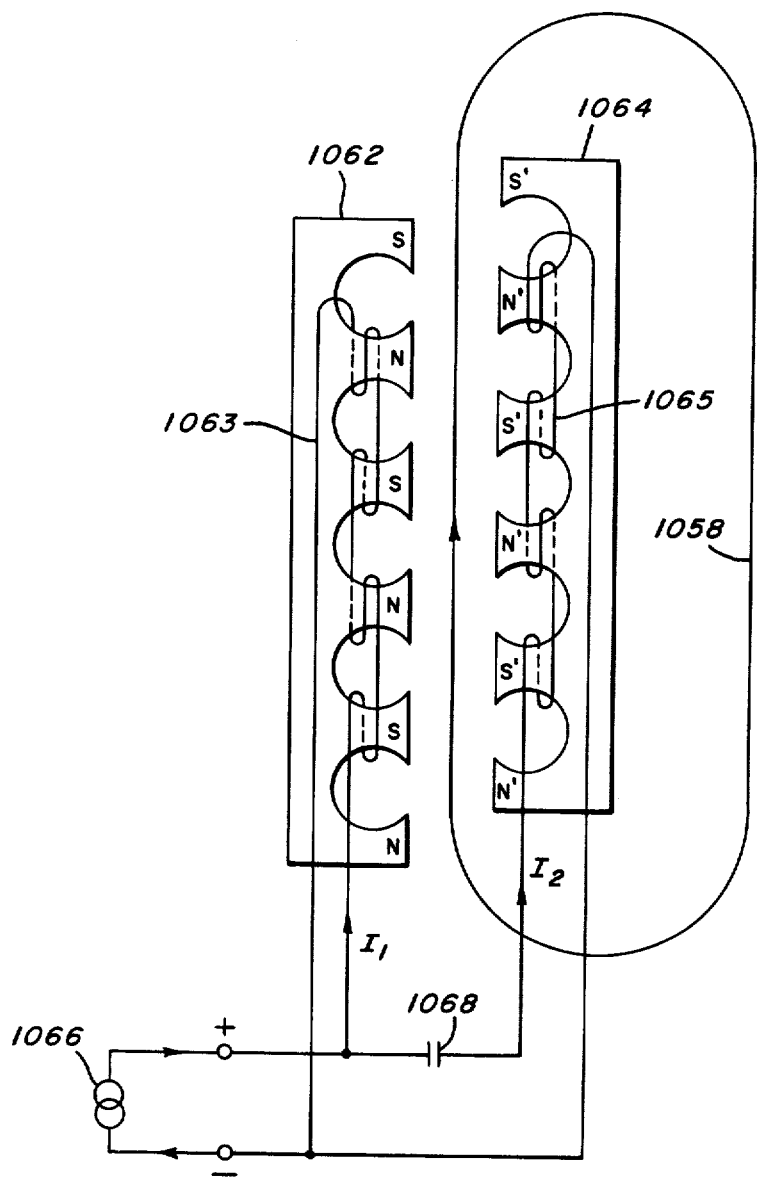
FIG. 44 is a partially schematic elevational view of the magnets of the belt drive means of FIG. 43 and associated electrical elements.

The full configuration of the magnets is shown in FIG. 44. The conductive portion 1058 of the endless belt 1044 passes through magnet pole pieces 1060 which are shown in detailed form in FIG. 44 as 1062 and 1064. Each pole piece may consist of a stack of laminated silicon transformer steel, each layer being from 0.010 to 0.025 inch thick, with from 40 to 100 layers being employed. As these pole structures might operate within a variety of liquids, the stacked lamination assemblies should preferably be cemented together and given a final coat of epoxy paint of the two-part variety. Such an epoxy paint coating, in several layers, can also obviate the need for additional spacers and insulators to prevent coils 1063 and 1065 from short-circuiting together with the metallic lamination structures. In operation, an alternating current source 1066 feeds power directly into coil 1063, and indirectly through capacitor 1068 into coil 1065. At any instant during the alternating current cycle, such as indicated by the + and − signs at 1066, the magnet structure 1062 has an alternating magnetic pole polarity designation, indicated by N, S, N, S, etc., representing "North" and "South" magnetic poles. Due to capacitor 1068 and the polarity of coil-windings 1065, the opposing pole polarities, N', S', N', S', etc., reach their maximum strength when the former poles pass through their zero-strength reversals. As this action is cyclic at the frequency of alternating current source 1066, the cumulative effect of both opposing and former pole configurations 1064 and 1062 is to generate a continuously traveling magnetic field pattern moving in the upward direction. On the opposing side of endless belt 1044 are two additional similar pole structures (not shown), similarly configured and electrically driven to cause a downward-traveling magnetic field. The conductive portion 1058 of belt 1044 drags along at a velocity slightly slower (65% to 95%) than the velocity of the magnetic field when this field configuration operates efficiently as an induction motor, or can also be made to provide greater drag force at relatively low (5% to 25% of field speed) velocities for an inefficient mode of operation, very similar to the action of an ordinary watt-hour meter. In this latter mode of operation, the conductive portion 1058 of endless belt 1044 would be woven with fewer strands of conductive fibers, so as to provide a higher resistance conductive portion 1058. The theory of such design approaches is well known in the art of induction motor design engineering.

Third Embodiment (FIGS. 45 Through 53)

Figure 45:
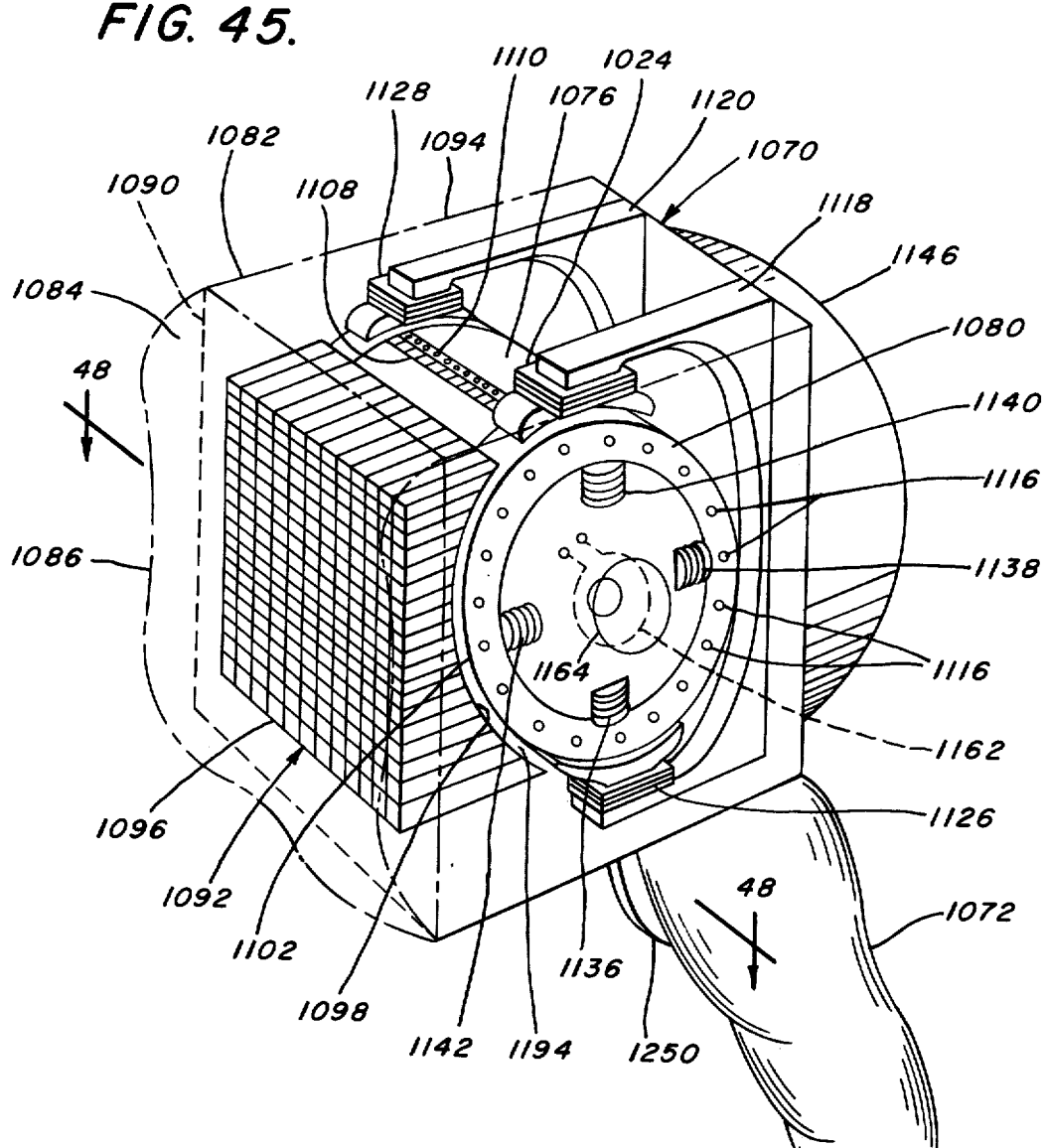
FIG. 45 illustrates a perspective partially schematic view of another embodiment of this invention.

Referring now to FIG. 45, there is shown a form of scanner 1070 which is of such size and weight as to be readily supported in one hand by means of handle 1072. For convenience of illustration, the outer walls have been shown schematically in terms of transparency, but the walls shown in this view actually would be opaque to facilitate better viewing through window 1150 (See FIG. 46), as described below. Electrical cable means 1074 are adapted to electrically energize scanner 1070. This embodiment may be of the real time (approximately 30 frames per second) through-transmission acoustical imaging type adapted for direct viewing purposes. In this embodiment, scanner 1070 has means for simultaneously processing acoustical signals from a linear array of transducers.

Figure 46:
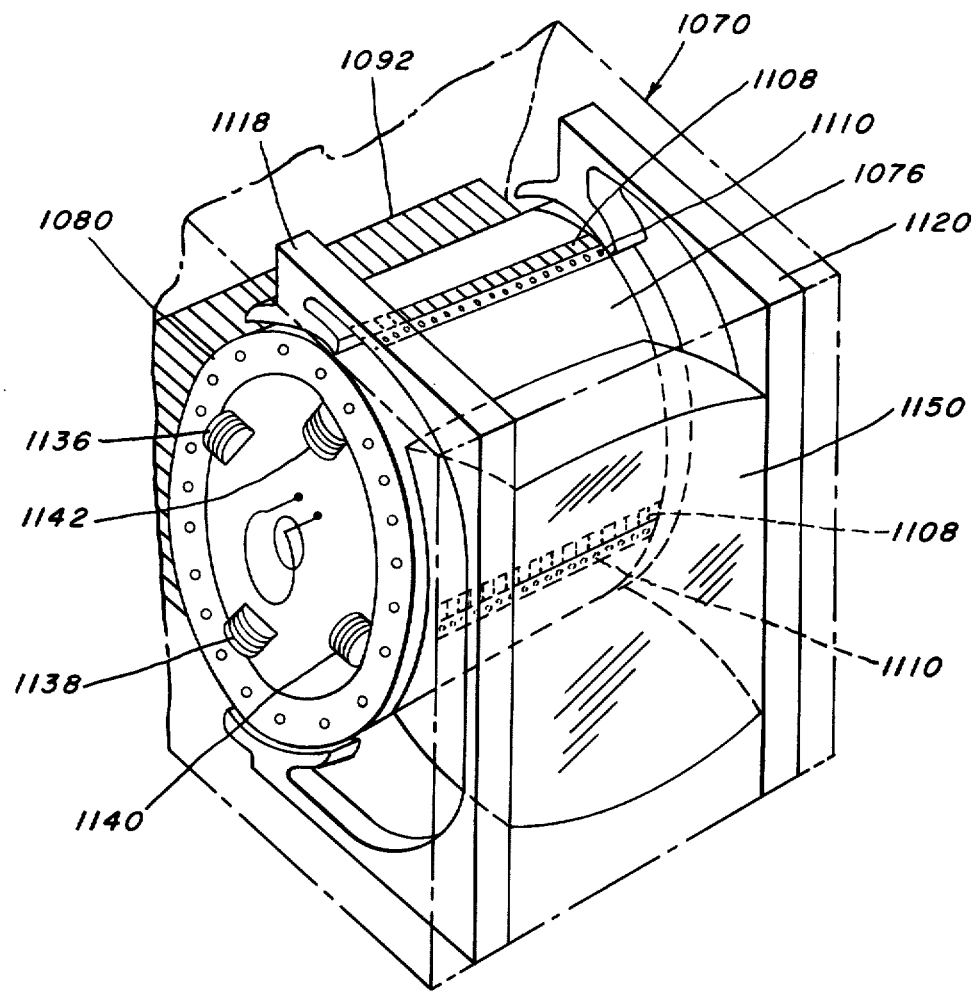
FIG. 46 is a fragmentary partially schematic perspective view of the embodiment shown in FIG. 45.
Figure 48:
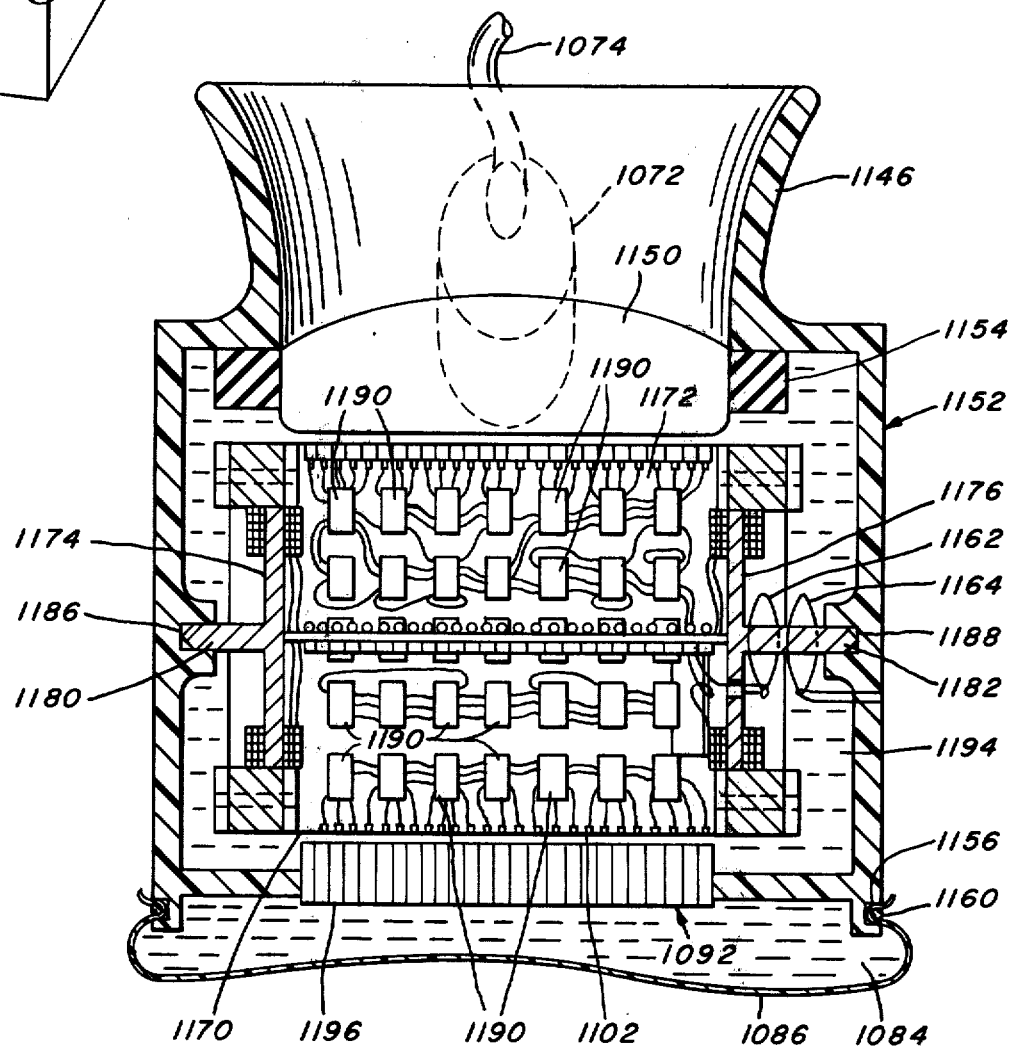
FIG. 48 is a cross sectional view of the embodiment shown in FIG. 45 taken through 48—48 of FIG. 45.

Referring now to FIGS. 45 and 46, it is seen that the scanner 1070 has a rotating drum 1076 which is provided within a sealed housing 1082 containing an acoustically conductive liquid (not shown in this view). The scanner 1070 has a second liquid chamber 1084 which has an outer resilient wall 1086 and is also filled with an acoustically conductive liquid (not shown). An areal sound pipe array 1092 passes through divider wall 1090 which separates chamber 1082 from chamber 1084 of sealed housing 1082. As is shown in FIGS. 45, 46 and 48, the sound pipe array 1092 has a generally flat forward face 1096 and a curved inner face 1098 which is of generally complementary curvature with respect to the outer surface 1102 of drum 1076 and is in relatively close proximity with respect thereto. The preferred average distance between inner surface 1098 and drum surface 1102 is about 0.050 to 0.150 inch, while any smooth surface which will provide effective acoustical coupling through the acoustically conductive liquid contained within the sealed enclosure 1082 will be suitable.

The sound pipe array 1092 is adapted to receive sound waves on the front substantially flat surface 1096 and transmit the acoustical waves through to the curved surface 1098. The acoustical waves with the aid of the conductive fluid will then be transmitted to the drum 1076. The sound pipe array 1092 may preferably consist of a bundle of a very large number, e.g., about 10,000 elements, for example, of small diameter Lucite rods embedded within a silicone rubber matrix. The silicone rubber may be of the type sold under the trade designation Type 615 RTV Silicone Rubber by General Electric.

As is shown in FIGS. 45 and 46, a linear array of receiving transducers 1108 is positioned on the circumference of the drum 1076 oriented generally parallel with the drum longitudinal axis. Preferably, about 40 to 150 individual transducers 1108 are within such array. A linear array of light emitting diodes 1110 is also positioned on the circumference of the drum oriented generally with the longitudinal axis of the drum and will preferably contain a number of light emitting diodes 1110 equal to the number of transducers 1108 in the array. In the form selected for illustration, the drum will have the array of transducers 1108 positioned closely adjacent the array of light emitting diodes 1110 and have four arrays of each provided on the exterior of drum 1076 circumferentially substantially equally spaced from each other.

Each array of receiving transducers 1108 and light emitting diodes 1110 consists preferably of about 40 to 125 elements with about 100 piezoelectric receiving transducers being preferred. It is preferred that the number of light emitting diodes 1110 in a given array equal the number of receiving transducers 1108 in the adjacent array.

It is contemplated that the flexible wall 1086 (FIGS. 45 and 48) will provide for complementary configuration with respect to the test specimen (not shown in these views). Secured within the drum 1076 is rotor 1080 which, in the form shown, is of the squirrel cage variety having squirrel cage shorting bars 1116 secured therein and oriented generally parallel to the longitudinal axis of the drum 1076. The rotor 1080 may conveniently be made of silicon transformer steel with outer plates of tinned copper sheet and the shorting bars 1116 may be made of tinned copper. The pair of stators 1118, 1120 are shown positioned adjacent the longitudinal ends of drum 1076. A pair of motor coils 1124, 1126 are secured to opposed ends of stator 1118. Stator 1120 is of similar configuration and has a similar pair of motor coils with coil 1128 being shown at the upper portion and the lower coil not being shown in FIG. 45. In the form shown, alternating current (AC) power, provided by the electrical cable 1074, passes through handle 1072 and by means of electrical connectors (not shown) serve to supply AC power to energize electrical coils 1124, 1126, 1128 and the fourth electrical coil located on stator 1120 in order to set up magnetid fields in stators 1118, 1120 which in turn establishes a motive torque in squirrel cage rotor 1080 which causes the drum to revolve about its longitudinal axis. The rotation may, for example, be on the order of 450 revolutions per minute or approximately 7.5 revolutions per second. Secured within the interior of drum 1076 and, in the form shown, attached to rotor 1080 are secondary coils 1136, 1138, 1140 and 1142 which have induced voltage build-up as a result of operation of the motor. This transformer action is employed, in a manner to be described in detail below, as a means for powering a number of internal signal handling means which preferably consist of integrated circuits which are housed within the rotating drum 1076.

Referring now to FIGS. 45 and 46, there is shown a portion of the means for permitting direct viewing or, in the alternative, photographing of the light emitting diode arrays 1110. As a convenient means of shutting out interfering light and permitting ready viewing of the illuminated light emitting diode arrays 1110, a hood 1146 which may be an annular tube-like object secured to the rear of sealed housing 1082 is provided. The hood 1146 is preferably composed of a material which is not translucent. Disposed rearwardly of drum 1076 is preferably a viewing window 1150 which in the form illustrated is a lens which may serve to magnify the swept acoustical image from the array of light emitting diodes 1110 and correct for cylindrical distortion inherent in the image. The correction for cylindrical distortion is accomplished by an aspheric lens design. If desired, the window 1150, whether in lens form or not, may serve as the rear wall of the sealed enclosure 1082. Such a construction is shown in FIG. 48. In the event that the window 1150 is not a lens, a separate lens may be provided, if desired. The window 1150 is secured to the housing shell 1152 by means of seal 1154. In the form illustrated, the housing shell is preferably composed of a molded rigid material such as plastic or neoprene, with neoprene being the preferred material. The joint between resilient wall 1086 and housing shell 1152 may conveniently be established by providing an annular recess 1156 within shell 1152 and inserting O-ring 1160 therewithin to secure the flexible wall in position.

As is shown in FIGS. 45 and 48, internal commutation antenna 1162 commutates signals received from external commutation antenna 1164 which in turn is operatively associated with external signal processing means (not shown in these figures).

In general, as is shown in FIG. 48, the principle of operation is that at a given instant the front quadrant 1170 of drum 1076 gathers acoustical information while the rear quadrant 1172 of drum 1076 displays such information in a through-transmission format with viewing being effected through rear window 1150.

As is illustrated in FIG. 48, the drum 1076 has end plates 1174, 1176 which have projections 1180, 1182 respectively which are rotatably secured respectively within journals 1186, 1188 of the outer housing 1152. Also shown in FIG. 48 somewhat schematically are internal electronic processing circuits 1190 which are in electrical contact with the arrays of light emitting diodes 1110 and receiving transducers 1108. These may advantageously be in the form of integrated circuits.

Figure 47:
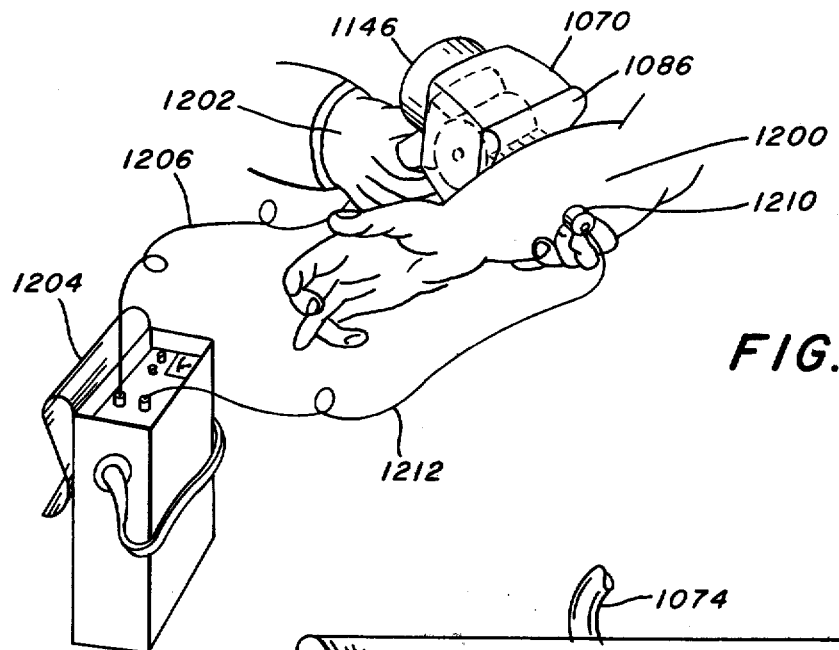
FIG. 47 illustrates a form of the embodiment of the invention shown in FIG. 45 in combination with a test specimen and external cooperating equipment.

Referring now to FIG. 47, the scanner 1070 is shown as employed in connection with a test specimen 1200, which in the form shown is a human arm. The scanner 1070 is shown as being held in the hand 1202 of the operator with the hood facing rearwardly and the flexible web 1086 in complementary acoustically coupled contact with the test specimen 1200. External electronics box 1204 contains external signal processing means (and also a power source) which serve to energize scanner 1070 through electrical conductor cable 1206. Cable 1206 also serves to communicate processing signals to and from the scanner 1070. Insonifying transducer 1210 is energized by means of the external signal processing means of external electronics box 1204 which provides high voltage pulses to operate the same through cable 1212. The external electronics box 1204 through cable 1206 provides energy to rotate drum 1076. The external signal processing means within box 1204 sends a command signal into the antenna commutation pair 1162, 1164 after an appropriate delayed time period, frequently in the nature of 100 microseconds, for example, after the high voltage pulses to insonifying transducer 1210, so that the scanner seeks acoustical imaging information at the right time, i.e., when the insonifying pulse has passed through the test specimen 1200.

Considering now FIG. 48 once again, a cycle of operation of the scanner 1070 will be considered. The arriving acoustical wave passing through the test specimen (not shown in this view) which specimen is in intimate complementary surface to surface contact with flexible wall 1086 causes the acoustical wave to pass through wall 1086 into the liquid within liquid chamber 1084 and then through the sound pipe array 1092 to an array of receiving transducers 1108 which is disposed within the second liquid chamber 1194 and faces sound pipe array 1092. Although both an array of light emitting diodes 1110 and receiving transducers 1108 are exposed to entering sound fields at front face 1170 of the drum 1076, only the transducers 1108 make a meaningful response which is that of sending electrical signals to the integrated circuits 1190 within the drum 1076. These integrated circuits 1190 cause the light emitting diodes 1110 at the same axial position as a particular predetermined transducer 1108 that has received an acoustical wave to be illuminated. If a number of transducers 1108 in the array receive an acoustical wave, all four of the light emitting diodes at the same drum axial position as each such transducer will be illuminated. The intensity of illumination of the predetermined light emitting diode 1110 may conveniently be either proportional to the intensity of the acoustical wave received by the particular transducer 1108 at the same drum axial position or proportional to the logarithm of the intensity of the sound field received in the preferred embodiments. As only one of the four light emitting diodes at the particular axial position is viewable through the rear window 1150, such light emitting diode 1110 will be viewed (or photographically recorded, if desired).

Figure 49:
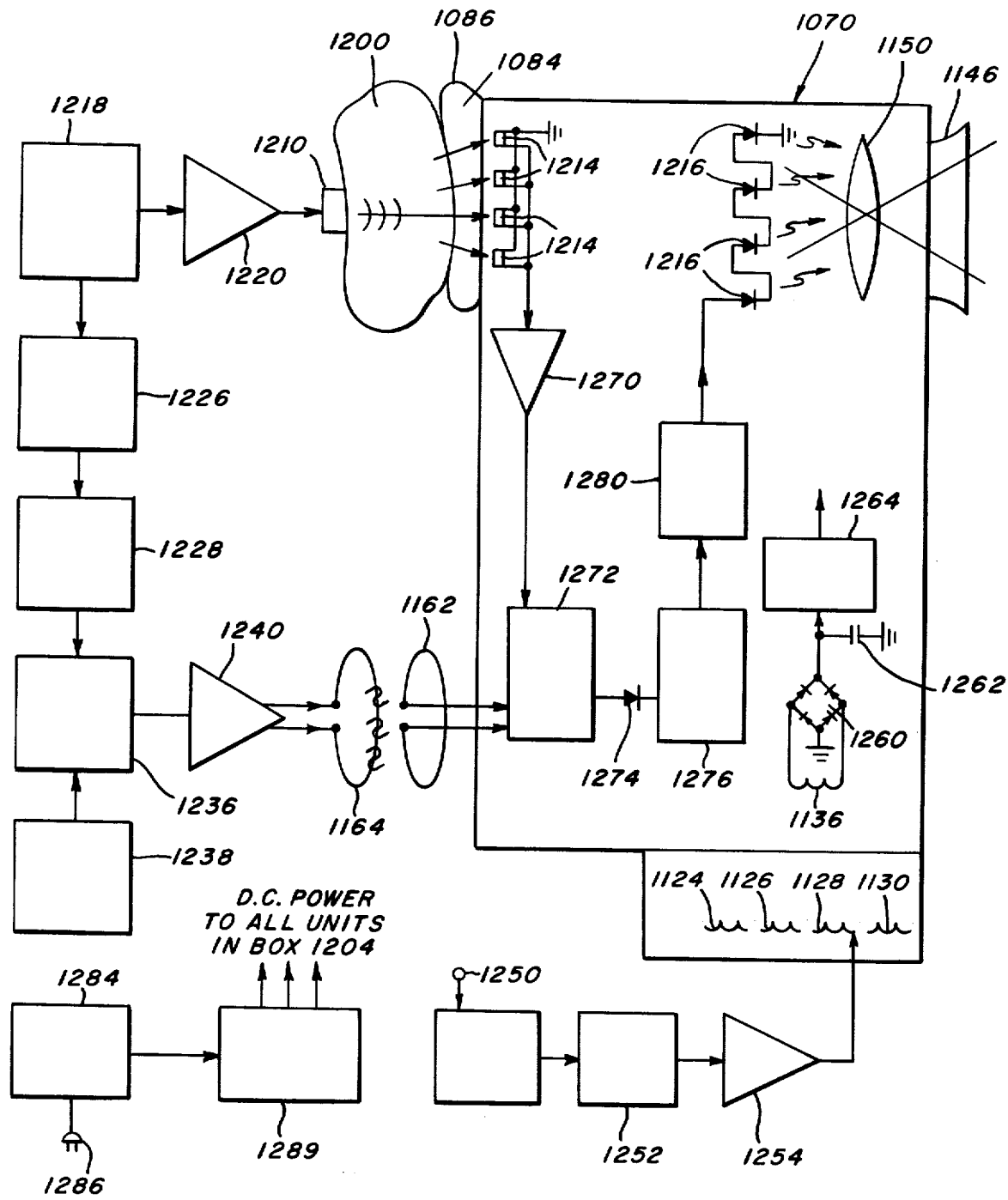
FIG. 49 is a block circuit diagram showing a form of circuit adapted for use with the embodiment of FIG. 45.

Referring now to FIG. 49, the cooperation between a preferred form of external signal processing means and the internal signal handling means of scanner 1070 will be considered. A pulse generator 1218 (which may, for example, be operated at about 2000 pulses per second) sends pulses to pulse amplifier 1220 that produces a high voltage output pulse to drive insonifying transducer 1210 which is in contact with test specimen 1200. The pulse generator 1218 also triggers the adjustable time delay generator 1226 which may, for example, produce a typical time delay of about 100 microseconds. The output of adjustable time delay generator 1226 initiates gate pulse 1228 which may, for example, be about 40 microseconds. The length of actual gate time which may range, for example, from about 20 to 50 microseconds, determines the length of time that the scanner 1070 may look for acoustical data. This "permission" to look for data is implemented by modulator 1236, the output of an associated radio frequency generator 1238 (which may, for example, be at 10 megahertz) and the resulting "on" burst of the RF signal as amplified by the radio frequency power amplifier 1240. The resulting "on" burst may, for example, have a 40 microsecond duration. The output of radio frequency power amplifier 1240 is fed into commutation antenna 1164 which in turn relays it by means of commutation antenna 1162 on drum 1076 to indicate when it is permissible to look for acoustical data.

When the operator presses push button switch 1250 (see FIGS. 45 and 49), an audio frequency oscillator 1252 (operating at, for example, 50 hertz) drives an audio frequency power amplifier 1254 and the output of this amplifier provides the power for drum motor field windings 1124, 1126, 1128, 1130. As a result, the drum 1076 rotates and derives its internal power from the induced voltage in secondary coils 1136, 1138, 1140, 1142.

Referring now to FIG. 49 and the internal signal handling means disposed within the scanner 1070 with reference to a particular secondary coil 1136, it will be appreciated that the remaining coils are joined to coil 1136 in either series or parallel combination to increase the available AC power to rectifier bridge 1260. The voltage induced in secondary coil 1136 will feed an integrated circuit rectifier bridge 1260 in order to produce raw direct current voltage across electrolytic capacitor 1262. The rectifier bridge may be that marketed under the trade designation MDA–922–1 by Motorola and may produce a 10 volt direct current with 2 volts ripple content. The electrolytic capacitor 1262 may have a capacitance of about 500 microfarads at 12 WV (working voltage). This raw direct current voltage is then regulated by integrated circuit regulator 1264. This may be of the type sold commercially under the designation Motorola MC 785 CP. This regulator 1264 serves to provide +5 volts direct current to all of the integrated circuits 1190 within the particular area with which it is associated.

Considering, for purposes of example, the four receiving transducers 1214 which will appear at substantially the same drum axial position with one being in each of the four arrays of transducers 1108, these four transducers will be connected electrically in parallel as will all transducers at the same axial position. The combined signal emerging from the four transducers 1214 goes to integrated circuit radio frequency amplifier 1270 (National Semiconductor Type LM172H is a suitable unit for this purpose) although at a given time only one of the four transducers 1214 receives any measurable sound field. The output of amplifier 1270 goes into gate 1272 (which may be I.C. Type LM 170) which is open to pass signals only when commutation antenna 1162 is receiving the "on" gate signal. The output of gate 1272 is rectified by diode detector 1274 (Type 1N914 is suitable) and the rectified signal representing the video information in acoustical imaging is peak-detected by peak detector 1276 and sent to light emitting diode driver 1280 (which may be I.C. LM324N) which in turn operates all four light emitting diodes 1216 at a given axial position, even though only one such diode 1216 is seen at a given time through window 1150.

As this is a real time scanner system, it may be operated as a portable system and a rechargeable nickel cadmium battery pack 1289 may advantageously be the power source in box 1204. It is adapted to be recharged by charger 1284 through AC line plug 1286. Battery pack 1289 is normally contained within box 1204. It will be appreciated that there is no direct connection between the battery pack 1289 and electronics within scanner 1070, as all control and operating power is sent to scanner 1070 through induction. This power unit 1289 is adapted to provide all of the power needed for the external signal processing means disposed in electronics box 1204. If desired, the scanner may be adapted to employ current directly from a wall outlet in lieu of the batteries.

Figures 50, 56:
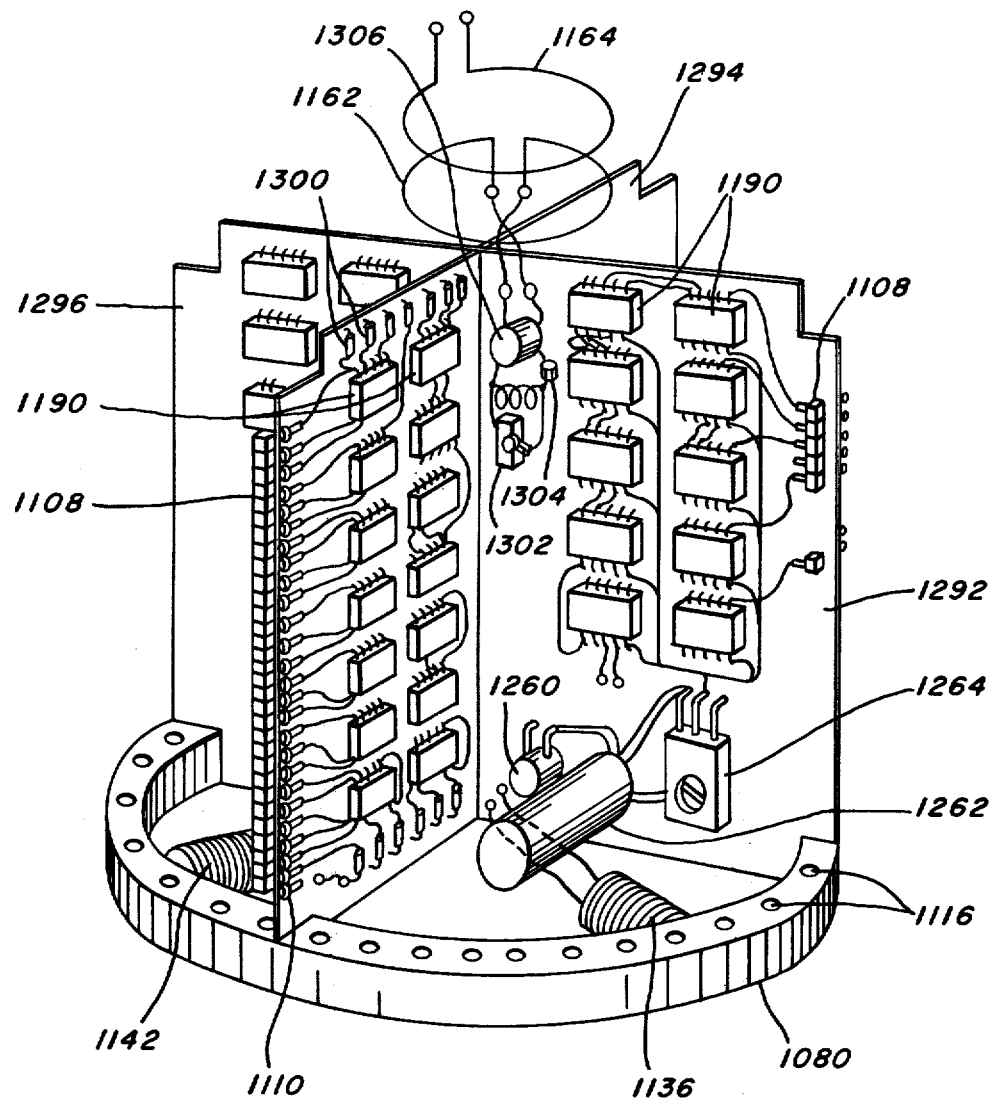
FIG. 50 is a fragmentary illustration of a portion of the drum interior.
FIG. 56 is a fragmentary detail of a form of linear transducer array.

Referring to FIG. 50, there is shown a broken away view of the drum 1076 illustrating a portion of the internal signal handling means. Adjacent arrays of transducers 1108 and light emitting diodes 1110 are shown connected to the internal signal handling means, a portion of which are mounted on boards 1290, 1292, 1294, 1296 which are generally radially oriented within the drum 1076. Secondary coils 1136, 1142 (shown in this view) have connections to the rectifier bridge 1260. The rectifier bridge 1260 is in turn connected to capacitor 1262 and regulator 1264. The dual in-line integrated circuits 1190, which will be discussed in greater detail below, are mostly amplifiers (such as LM172N manufactured by National Semiconductor Corp., for example) except for diodes 1300, the gate receiver circuit which consists of a tuned circuit 1302, a diode detector 1304, a transistor 1306 and several additional resistors (not shown) which is connected to commutation antenna 1162 which is coupled with commutation antenna 1164.

While most of the external signal processing means discussed in connection with FIG. 49 are of the conventional variety and a number of specific examples of the same have been presented above in connection with certain specific embodiments of the invention, some additional discussion will be provided for further guidance to those skilled in the art at this point.

The gate pulse generator 1228 may conveniently be a one shot multivibrator without a following pulse forming circuit and is identical in design to the one-shot multivibrator of FIG. 42, minus the pulse-forming circuit, and may have an active time of about 40 microseconds.

The multiplier 1236 should preferably be the wide band integrated circuit variety.

Consideration will now be given to a particular integrated circuit unit 1190 with reference to FIG. 52. It will be appreciated that the circuit portion numbered 1191 will be duplicated for each receiving transducer 1108 and each light emitting diode 1110. Only one circuit of gate receiver type collectively numbered 1209 consisting of elements 1302, 1304 and 1306 need be provided for the entire scanner electronics package 1070. In the operation of the particular circuit illustrated in FIG. 52, when a commutation antenna 1162 receives radio frequency energy, the gate receiver 1290 causes the voltage coming out of the emitter lead of the transistor 1330 to go to 0 volts. This 0 volts signal is provided to the squelch input connection indicated at 1332 of integrated circuit amplifier 1272 (which may be type LN370N sold by National Semiconductor Corp.) thereby activating this amplifier to pass on the signal from the previous amplifier 1270 to diode detector 1274. It will be understood that at least one of the four transducers 1214 is receiving acoustical signals all of the time and that the signals cannot pass through amplifier 1270, 1272 until the gate control input provides permission to process the correct acoustical signal, i.e., the signal received from the test specimen and not a reverberation from a previous pulse. Once a signal has been rectified by diode detector 1274, its peak amplitude is stored in peak detector 1276 and the slowly varying voltage decaying with about a 400 microsecond constant, for example, drives the light emitting diode amplifier 1280 which in turn lights up the light emitting diodes 1216 in an intensity proportional to the detected signal at diode detector 1274. This means that the light emitting diodes emit light in proportion to the received acoustical pressure at transducers 1214, but only at time intervals selected as being permissible by the gate receiver circuitry 1290 as cued by inner commutation antenna 1162.

Figures 52, 53:
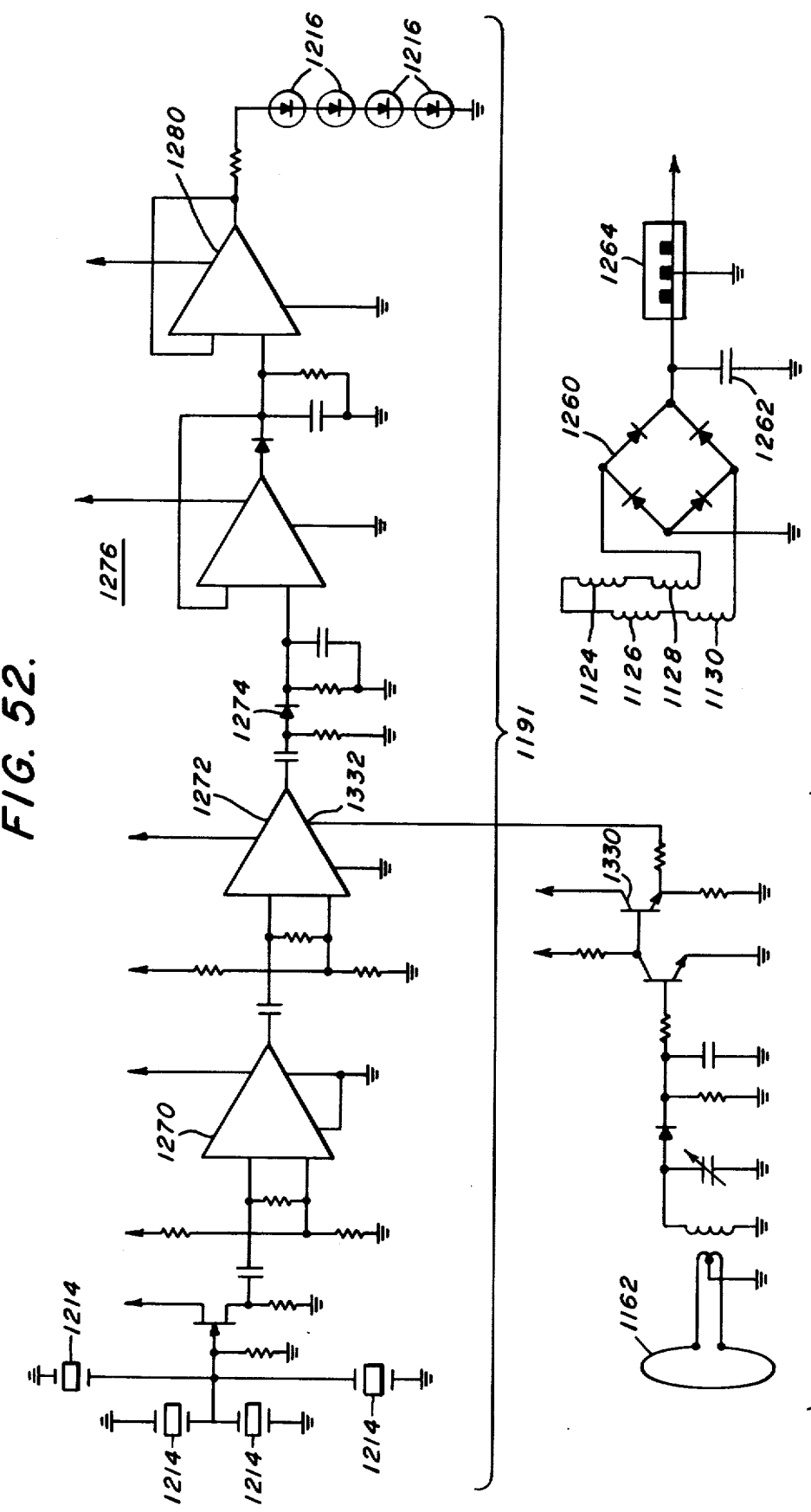
FIG. 52 is a detail of a form of integrated circuit adapted for use in the circuits illustrated in FIG. 50.
FIG. 53 is an illustration of another circuit portion adapted for use in the circuitry of FIG. 50.

FIG. 53 illustrates a detail of the secondary coils and related drum contained circuitry intermediate the coils 1124, 1126, 1128, 1130, rectifier 1260, capacitor 1262 and the integrated circuit regulator 1264.

Figure 51:
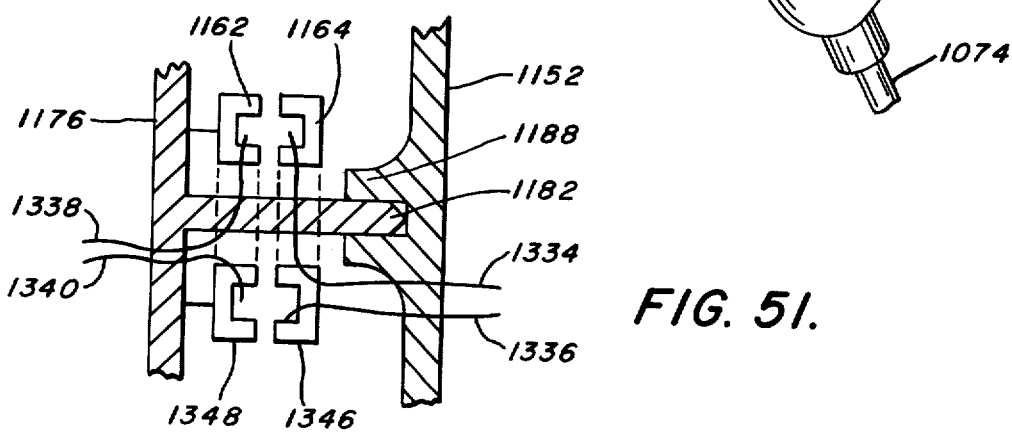
FIG. 51 is a fragmentary cross sectional view illustrating a detail of a form of the antenna commutation means of this invention.

Referring now to FIG. 51, there is shown a preferred form of arranging the magnetic commutation antennas 1162, 1164 within the sealed housing. As is shown in FIG. 51, one drum end plate 1176 has its projecting leg 1182 rotatably secured within journal 1188 of outer casing 1152. Electrical leads 1334, 1336 connect the antenna 1164 with the exterior of the sealed housing, while electrical leads 1338, 1340 connect antenna 1162 with the internal signal handling means. In the form illustrated in FIG. 51, generally channel shaped annular enclosures 1346 and 1348, respectively, protectively surround antennas 1164, 1162 and are secured to drum end wall projecting leg 1182 by any suitable means such as a silicone rubber adhesive (not shown). The material out of which cup-shaped protective member 1346, 1348 may be made could be that sold as Core No. A-43019-16 manufactured by Magnetics, Inc.

Fourth Embodiment (FIGS. 54 Through 63)

The fourth embodiment may be generally identical to the third embodiment in all respects except for the positions of the transducer and light emitting diode arrays and the presence of the sound pipe array in the third embodiment.

Figures 54, 63:
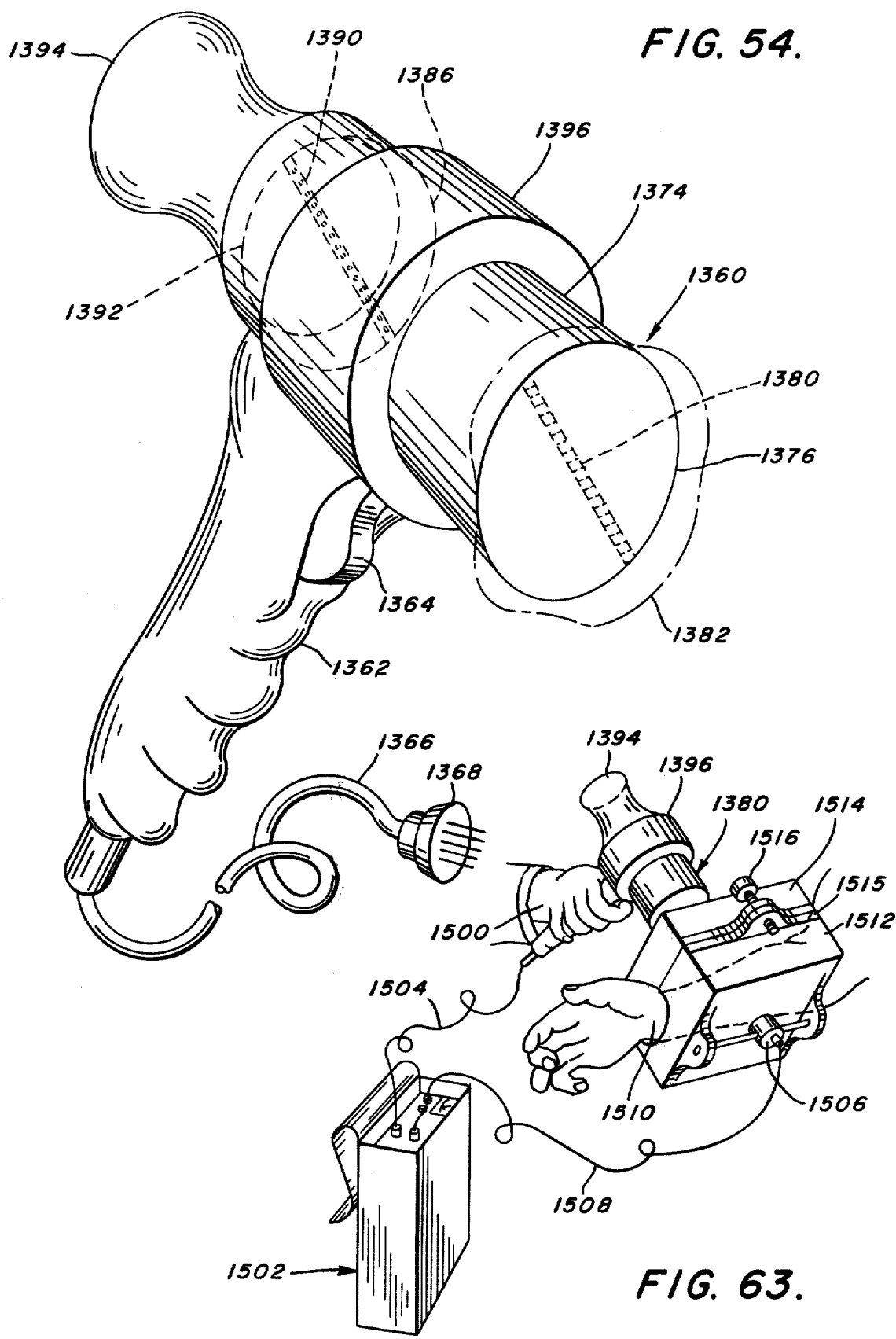
FIG. 54 illustrates a partially schematic view of a fourth embodiment of the invention which has a portable generally drum-like apparatus.
FIG. 63 illustrates the embodiment of FIG. 54 used in cooperation with a particular specimen holding device and associated external equipment.

Referring now to FIG. 54, there is shown a partially schematic view of an end viewing drum scanner 1360 which is adapted to be supported in one hand and is readily portable. For convenience of illustration, the scanner 1360 has been shown with transparent walls to permit illustration of interior components in FIG. 54. Generally, all walls except the viewing wall would be opaque. This scanner 1360 has a sealed housing and a handle grip 1362 into which is mounted a switch 1364 which is adapted to be urged into its outward "switch off" position by an internal spring whose resistance is overcome manually during operation of the scanner 1360. An electrical cable 1366 has an end plug 1368 which is adapted to be electrically coupled with a suitable source of electrical energy. Rotating drum 1374 has a front end plate 1376 upon which is mounted a plurality of receiving transducers in a linear array 1380. Secured to the rear of the drum 1374 and rotatable therewith is rear end plate 1386 upon which is mounted a linear array of light emitting diodes 1390. Disposed rearwardly of rear end plate 1386 is clear or transparent window 1392 which provides a rear closure for the rotating drum 1374. Hood 1394 facilitates viewing through clear window 1392. In the preferred form, the clear window 1392 will either be a magnifying lens or have a magnifying lens (not shown) positioned adjacent thereto.

The liquid filled sealed housing has a resilient outer wall 1382 which effects a seal with the outer housing member (not shown in this view). If desired, the sealed housing may be divided into two chambers as by providing an acoustically transparent rigid wall between drum 1374 and resilient outer wall 1382.

A collar 1396 is provided to contain some of the internal signal handling means and, as will be described more fully below, collar 1396 may also contain means for providing power to rotate drum 1374, means to energize internal signal handling means and commutation means. In general, the internal signal handling means (not shown in this view) may be substantially identical to that described in connection with the third embodiment, if desired. The collar 1396 may contain electrical windings, such as the stator of a conventional split-phase alternating current induction motor.

Referring now to FIG. 56, there is shown a convenient means of mounting the receiving transducer array 1380 for securement within electrically conductive front end plate 1376 which is preferably circular and composed of machined brass of a thickness of about 0.050 to 0.080 inch. In this method a stainless steel plate 1402, preferably about 0.002 inch thick, has a plurality of elongated transducers 1400 secured thereto by means of electrically conductive cement 1404. Electrically conductive hair wires 1406 are secured to the upper portion of the transducers 1400 by means of conductive cement 1408. The impinging acoustical waves will approach the transducer array 1380 in the direction indicated by the underlying arrow. The plate 1402 is essentially transparent to acoustical waves in the range of about 0.5 to 4 megahertz (MHz) frequency range while acting as a structural support member and an electrical shielding member. The transducers may preferably be cubic of about 0.050 inch on a side and resonate at about 2.3 MHz. The array of transducers 1380 preferably consists of about 25 to 75 transducers.

As is shown in FIG. 55, the plate 1402 is secured to drum front plate 1376, which has annular flange 1412, by means of fasteners 1320 which may conveniently be corrosion resistant screws. The hair wire 1406 provides electrical coupling between the transducers 1400 and epoxy terminal block 1416. Electrical lead 1418 connects the terminal block 1416 with R.F. amplifiers, similar to 1270 (see FIG. 52) (not shown in this view).

The transducers may be made from rectangular bar stock such as HS-21 material sold by Glenite, for example, and having dimensions of about 0.05 inch by 0.05 inch, for example. The preferred cement 1404, 1408 is an electrically conductive silver cement such as that sold under the trade designation Polycomp 21–30. The terminal block 1416 may preferably be a molded epoxy terminal block.

The electrical lead 1418 will connect the transducers 1400 with the internal signal handling means. A perspective view of the transducer array 1380 secured to the front end plate 1376 is shown generally in FIG. 60.

Referring now to FIGS. 57 and 59, there is shown the drum 1374 with the squirrel cage rotor portion 1430 and secondary coils 1432, 1434 which may conveniently be wound in the shorting bar slot locations of the squirrel cage rotor 1430. The rotor 1430 has a plurality of squirrel cage elements 1436. These secondary coils which may number about 2 to 4 serves as a means for energizing the internal signal handling means disposed within the drum 1374. As is shown in FIG. 59, secondary coils 1432, 1434 can be connected to a full wave rectifier bridge 1438 and to a capacitor 1439 in order to provide an internal unregulated direct current power supply within the drum 1374. A regulator (not shown) may also be provided similar to regulator 1264 (FIG. 49).

FIG. 58 shows an alternate means of establishing the light emitting diode array. In this form a plate 1446 is provided with a plurality of openings into which the individual light emitting diodes 1448 may be press fitted to create the light emitting diode array 1390, with or without the use of a liquid-sealant adhesive, such as General Electric Silicone Rubber 102, for example.

Referring now to the cross sectional view shown in FIG. 61, it is seen that a stator 1462 is housed within collar 1396 and is of the split-phase motor stator variety. The running windings 1454, 1456, 1458, 1460 are illustrated as being shaded in order to provide clarity of illustration, while the starting windings 1464, 1466, 1468, 1470 are illustrated as unshaded. It is noted that the region 1450 within rotor 1430 is the place within which the internal electronics circuits portion of the internal signal handling means (not shown in this view), which may conveniently be integrated circuits, would be positioned. In actual operation, the alternating current power is supplied from an external source, such as an electronics box (not shown in this view) through cable 1366 when the switch 1364 is in the proper position. This alternating current operates running windings 1454, 1456, 1458, 1460 directly and the starting windings 1464, 1466, 1468, 1470 through capacitor 1478 in order to effect a phase shift to such starting windings 1464, 1466, 1468, 1470. The switch 1364 on the pistol grip handle 1362 allows the operator to operate the scanner only when the switch is held in the "on" position by finger pressure.

Referring now to FIG. 62, there is shown the squirrel cage rotor 1430 with the individual integrated circuit units 1488 mounted upon circuit boards 1490 and anchored thereto by suitable means. These circuit units 1488 and the related internal electrical components may be essentially identical to those of the third embodiment, if desired. Internal commutation antenna 1484 is electrically connected with the integrated circuits 1488 by means of lead 1492. External commutation antenna 1486 receives signals through the exterior of the sealed housing so as to provide coordination between the external signal processing means and the internal electronic circuits 1488.

In operation, the flexible wall 1382 (FIG. 54) will be in intimate complementary relationship with the test specimen and the drum 1376 will contain an acoustically conductive liquid. When a predetermined receiving transducer 1400 receives an acoustical wave, the signal received will be converted to an acoustical function electrical signal which by means of internal signal handling means and external signal processing means will result in illumination of a predetermined light emitting diode with the degree of illumination being proportional to the intensity of the acoustical wave received by the individual transducer 1400.

Referring now to FIG. 63, there is shown the scanner 1380 of this embodiment which is being supported in hand 1500 of an operator. External electronics box 1502, which contains identical circuitry as that illustrated for the electronics box in the third embodiment of this invention, provides electrical energy to drive the drum electric motor and to communicate through commutation antenna 1484, 1486. Insonifying transducer 1506 receives energy from exterior electronics box 1502 through electrical lead 1508. While, in general, the insonifying transducer 1506 and the scanner 1380 would be in direct contact with the test specimen 1510 with an interposed acoustical couplant material, in this view a resilient acoustically conductive specimen holder consisting of two halves 1512, 1514 secured together by suitable clamping members 1515, 1516 serve to provide acoustical continuity between the test specimen 1510 and the insonifying transducer 1506 and scanner 1380.

As used in this application, reference to effecting acoustical contact between a test specimen and a scanner shall be deemed to include not only there being interposed an acoustical coupling material such as a grease, but also shall include various sorts of acoustically conductive clamping members such as a clamping member composed of sections 1512, 1514.

It will, therefore, be appreciated that the present invention has provided a light, portable, rapid ultrasonic scanning device of both the B-scan and through-scan varieties adapted to be used with a wide range of specimens including medical test specimens and in other forms of non-destructive testing such as on metal specimens. All of this is accomplished while maintaining rapid data collection, processing and producing high resolution imaging. The self-contained scanner units contain means for moving one or more receiving transducers and internal electronics for processing the received acoustical signals and converting the same into meaningful electrical signals which may be employed when coordinated with external electronics processing to provide video images through external means, such as a cathode-ray tube, for example. In addition, these units may provide a visual image preserved on photographic means, may be employed as a direct visual ultrasonic tester or may be employed with other convenient means of data readout and recording. The signals of the present invention are adapted for use with internal electrical integrated circuits and provide a lightweight instrument which may readily be held in one hand of the operator. In addition, novel transducer propulsion methods, signal processing and conversion methods and noncontacting commutation means are provided. The invention also provides the advantage of substituting high speed mechanical movement for unreliable manual movement of a transducer in tests such as B-scan operations.

It is contemplated that a scanner of this invention may have overall exterior dimensions of about 5 to 12 inches in length and 5 to 15 inches in transverse maximum dimension and may have a weight of about 3 to 12 pounds.

As a result of the apparatus of this invention, cumbersome and unpleasant tank immersion techniques are not required and other patient inconveniences in the case of medical specimens are eliminated. A flexible wall may be provided in the scanner so as to improve the efficiency of complementary contact between the scanner and test specimen.

All of the foregoing has been accomplished in such a fashion as to permit economical manufacture of highly reliable portable instruments which with a high degree of sensitivity and reliability, can provide increased mobility of the equipment and ready manual support therefor during use, coupled with reduced inconvenience such as would be required in the submergence technique in medical ultrasonics.

For convenience of reference and clarity of illustration herein, various words of orientation such as "front", "rear", "up", "down" and similar words have been employed, but it will be appreciated that, unless expressly indicated to the contrary in a particular use, these are purely illustrative and are not limiting upon the scope of the invention.

While for convenience of illustration the external signal processing means has been illustrated as being in a box which is physically separate from the sealed housing and such construction is a preferred approach, it will be appreciated that, if desired, the box or enclosure for the external signal processing means may be secured to or formed as part of the exterior of the sealed housing.

Whereas particular embodiments of the invention have been described above for purposes of illustration, it will be evident to those skilled in the art that numerous variations of the details may be made without departing from the invention as defined in the appended claims.

I claim:
1. An integrated closed ultrasonic scanner comprising
a sealed housing having at least one mechanically compliant wall,
an acoustically conductive liquid disposed within said sealed housing,
an endless belt disposed within said housing and mounted for orbital movement therewithin,
at least two piezoelectric transducers secured to said endless belt,
drive means disposed within said sealed housing for driving said endless belt to establish orbital movement of said transducers,
magnetic commutation means for energizing said transducers and transferring acoustical function electrical signals to the exterior of said sealed housing,
electrical cable means operatively associated with said magnetic commutation means and said drive means and being in communication with the exterior of said sealed housing for cooperation with external signal processing means and an electrical energy source,
a fresnel deflecting lens disposed between said endless belt and said mechanically compliant wall, and
means for reciprocating said fresnel lens in a direction generally perpendicular to the direction of travel of said orbiting transducers.

2. The ultrasonic scanner of claim 1 including
said drive means including a pair of rotatable pulleys disposed within said sealed housing,
said endless belt secured over said pulleys for movement therewith, and
said transducers disposed on the exterior of said endless belt.

3. The ultrasonic scanner of claim 2 including
said endless belt being an elastic fabric woven belt which is positioned over said pulleys in elastic tension.

4. The ultrasonic scanner of claim 2 including
said magnetic commutation means including a commutation spring secured to said endless belt and connecting said transducers electrically in series.

5. The ultrasonic scanner of claim 4 including
said magnetic commutation means including a shaft upon which one of said pulleys rotates, a pair of side members and an upper member all of which are magnetically conductive and cooperate to define a closed magnetic loop,
the length of said side members being greater than the radius of the pulley which rotates on said shaft,
said magnetic commutation means including an electrical coil wound around said magnetic loop and a Faraday shield surrounding said coil, and
said coil being in electrical communication with said cable means, whereby an electrical pulse within said electrical cable means will through inductive action of said coil excite magnetic pulses in said magnetic loop which in turn will induce currents in said commutation spring to energize said transducers.

6. The ultrasonic scanner of claim 1 including
said sealed housing having a substantially rigid wall which is sealingly secured to said mechanically compliant wall, and
said electrical cable means passing through said substantially rigid wall.

7. The ultrasonic scanner of claim 6 including said substantially rigid wall and said mechanically compliant wall each composed, at least in part, of electrically insulative plastic resins.

8. The ultrasonic scanner of claim 2 including said drive means including at least one electric motor disposed within said sealed housing.

9. The ultrasonic scanner of claim 8 including said electric motor having stator laminations provided with field windings disposed on opposed sides of one said pulley, said pulley serving as the armature of said electric motor, and electrically conductive means connecting said field windings with said electrical cable means.

10. The ultrasonic scanner of claim 9 including said stator laminations having first pole pieces to provide the main magnetic field and second pole pieces provided with shorting bars to provide quadrature phase delayed magnetic fields.

11. The ultrasonic scanner of claim 9 including two said electric motors disposed within said sealed housing, whereby said endless belt will be driven at both said pulleys.

12. The ultrasonic scanner of claim 1 including said fresnel lens being flexible, said fresnel lens reciprocating means including a slotted plate member secured to and oriented generally perpendicular to said fresnel lens, pawl means adapted to be received within said slotted plate member, and gear means moving said pawl means responsive to rotation of one said pulley.

13. The ultrasonic scanner of claim 12 including a said slotted plate member secured to said fresnel lens adjacent to each said pulley, each said plate having a pair of upwardly open slots, and said pawl means including a pawl element extending into each said upwardly open slot.

14. The ultrasonic scanner of claim 13 including said gear means associated with a first said pulley including a pair of worm gears being generally axially concentric with said pulley and secured to opposed sides of said pulley for rotation therewith, a pair of second gears meshed with said worm gears having an axis of rotation oriented generally transversely with respect to the axis of said worm gears, and a said pawl element eccentrically secured to each of said second gears.

15. The ultrasonic scanner of claim 14 including a pair of rotatably mounted wheels having eccentric pawl elements extending into the slots of the said plate member disposed closer to the second said pulley, and flexible shaft means connecting said second gears to said wheels, whereby rotation of said first pulley will effect responsive reciprocation of said fresnel lens.

16. The ultrasonic scanner of claim 12 including means for emitting an electrical signal through said electrical cable means responsive to pulley rotation, whereby electrical operation of said scanner may be coordinated with reciprocation of said fresnel lens.

17. The ultrasonic scanner of claim 16 including a highly reflective spot on one said pulley, a lamp disposed in position to shine on said reflective spot when said pulley is in a particular angular position, a photocell receiver disposed in position to receive the light from said lamp reflected by said spot, whereby a responsive reduction in photocell electrical resistance will be effected once for each pulley rotation, and said photocell electrically connected to said cable means.

18. The ultrasonic scanner of claim 1 including said drive means including a pair of rotatable pulleys upon which said endless belt is mounted serving as electric motor rotors and a pair of stators associated with each said rotor, one said stator of each said stator pair being an inner stator disposed between said pulleys and closely adjacent to the said pulley with which it is associated, and deformable linkage means connecting said inner stators.

19. The ultrasonic scanner of claim 18 including said deformable linkage means including a first link secured to a first said inner stator and a second link secured to a second said inner stator, and at least one additional link interposed between said first and second links and being rotatably secured to adjacent links.

20. The ultrasonic scanner of claim 19 including said first link rotatably secured to said first inner stator, said second link rotatably secured to said second inner stator, and compressibly resilient means interposed between at least two said rotatably connected links to maintain said linkage in a predetermined configuration in the absence of applied forces sufficient to compress said resilient means.

21. The ultrasonic scanner of claim 19 including each pair of said rotatably connected links having a pair of aligned openings into which a retainer pin is received.

22. The ultrasonic scanner of claim 18 including bracket means securing each said stator to the adjacent said pulley.

23. The ultrasonic scanner of claim 2 including said scanner having two said transducers, and said transducers being so positioned on said endless belt that the distances therebetween measured along the belt circumference will be generally equal regardless of whether the measurement is effected in a clockwise or in a counterclockwise direction.

24. The ultrasonic scanner of claim 23 including a piezoelectric receiving transducer overlying said endless belt, an acoustically absorptive material overlying said piezoelectric receiving transducer, and electrically conductive means connecting said piezoelectric receiving transducer with said electrical cable means.

25. The ultrasonic scanner of claim 23 including switch means to permit the reflected acoustical wave received by a said belt mounted transducer to be transmitted electrically to said external signal processing means solely when said belt mounted transducer is in predetermined positions.

26. The ultrasonic scanner of claim 25 including said switch means including a reed switch mounted in close proximity to said endless belt and permanent magnets mounted on said endless belt for operating said reed switch.

27. The ultrasonic scanner of claim 1 including
said fresnel lens having means for deflecting acoustical beams to simulate B-scan rocking action.

28. The ultrasonic scanner of claim 27 including
said fresnel lens deflecting means including a lenticular vane structure facing said mechanically compliant wall.

29. The ultrasonic scanner of claim 28 including
said lenticular vanes having a replication distance less than the diameter of said belt mounted transducers.

30. The ultrasonic scanner of claim 1 including
said external signal processing means including pulse generator means disposed exteriorly of said sealed housing for emitting periodic voltage pulses, and
internal signal handling means disposed within said sealed housing and being in communication with said electrical cable means, whereby said internal signal handling means will be in communication with said external signal processing means through said cable means to permit the processing of acoustical function electrical signals emerging from said sealed housing by said external signal processing means.

31. The ultrasonic scanner of claim 30 including
said external signal processing means including
a pulse amplifier adapted to receive signals from said pulse generator and transmit-receive means, and
said transmit-receive means adapted to receive pulses from said pulse amplifier and deliver such pulses to said cable means which in turn is adapted to deliver such pulses to said magnetic commutation means.

32. The ultrasonic scanner of claim 31 including
said transmit-receive means adapted to receive acoustical function electrical signals from said magnetic commutation means through said cable means.

33. The ultrasonic scanner of claim 32 including
said external signal processing means including logarithmic receiver means, cathode-ray tube visual display means and video amplifier means,
said logarithmic receiver means operatively associated with said transmit-receive means, and
said video amplifier means operatively associated with a variable intensity input of cathode-ray tube visual display means.

34. The ultrasonic scanner of claim 33 including
said external signal processing means including Y-sweep generator means operatively associated with said pulse generator means for emitting a ramp-function output waveform which will pass through Y-wave modifying means and be delivered to Y-deflection coils of said cathode-ray tube visual display means.

35. The ultrasonic scanner of claim 34 including
said internal signal handling means including switch means to permit the reflected acoustical beam received by a said belt mounted transducer to be transmitted electrically to said external signal processing means solely when said belt mounted transducer is in predetermined positions, and
said external signal processing means including X-sweep generator means to receive said acoustical function electrical signal and emit a ramp-function waveform which will pass through X-wave modifying means and be delivered to X-deflection coils of said cathode-ray tube visual display means.

36. The ultrasonic scanner of claim 35 including
said endless belt having two said transducers secured thereto in such position that when a first said transducer is facing downwardly toward the test subject, the second said transducer will be facing upwardly,
a piezoelectric receiving transducer overlying said second transducer and emitting a voltage pulse responsive to receipt of an acoustical pulse from said second transducer, and
said piezoelectric receiving transducer adapted to emit said voltage pulse after the leading edge of the master timing pulse from said pulse generator means has passed through said second transducer with the time interval between said master timing pulse and said voltage pulse being proportional to the distance between said second transducer and said piezoelectric receiving transducer.

37. The ultrasonic scanner of claim 36 including
said external signal processing means including means for processing said piezoelectric receiving transducer voltage pulse to establish a Y-offset adjustment signal responsive to changes in configuration of said endless belt.

38. The ultrasonic scanner of claim 37 including
said Y-wave modifying means including Y-modulator means receiving said Y-sweep generator ramp-function output, Y-mixer means and Y-deflection amplifier means,
said Y-mixer means for combining said Y-offset adjustment signal with the Y-multiplier means output signal, and
said Y-deflection amplifier means for receiving said Y-mixer means output, amplifying the same and introducing its output signal into Y-deflection output coils of said cathode-ray tube visual display means, whereby the Y-deflection line on said visual display means will be corrected for changes in contour of said endless belt.

39. The ultrasonic scanner of claim 38 including
said means for processing said piezoelectric receiving transducer voltage pulse including, in operative sequence, second logarithmic receiver means, second video amplifier means, threshold detector means, stop trigger means, integrator means and peak detector means,
said threshold detector means being adapted to compare an amplified voltage pulse received from said second video amplifier means with a reference voltage,
said integrator means being connected to said pulse generator means to receive signals therefrom, and
said peak detector means output being received in said Y-mixer means.

40. The ultrasonic scanner of claim 39 including
said X-wave modifying means including X-mixer means and X-deflection amplifier means.

41. The ultrasonic scanner of claim 40 including
said external signal processing means including signal modifying means responsive to reciprocation of said fresnel lens for adjusting for changes in acoustical beam orientation through the test subject.

42. The ultrasonic scanner of claim 41 including said signal modifying means receiving the output signal of said photocell means through said electrical cable means, and said signal modifying means including digital divide circuit means for emitting an output voltage pulse responsive to receipt of a predetermined number of photocell signals, ramp generator means for emitting a triangular waveform output responsive to receipt of said divide circuit voltage pulse, sine generator means receiving said triangular waveform and emitting a sine wave of voltage value and polarity proportional to fresnel lens position and third mixer means receiving the output of said sine wave generator.

43. The ultrasonic scanner of claim 42 including
said external signal processing means including means for computing a change factor resulting from changes in deflection caused by deformation of said endless belt, and
said third mixer means receiving the output of said change factor computing means.

44. The ultrasonic scanner of claim 43 including
said external signal processing means including cosine generator means and second sine generator means,
said cosine generator means for receiving an output signal from said third mixer means and operating said Y-modulator means, and
said second sine generator means for receiving an output signal from said third mixer means and operating X-modulator means.

45. An integrated closed ultrasonic scanner comprising
a sealed scanner housing,
an acoustically conductive liquid disposed within said sealed housing,
an endless belt disposed within said housing mounted for orbital movement in one direction and translational movement in another direction,
at least one transducer secured to said belt,
at least one light emiting diode secured to said belt,
drive means disposed within said sealed housing for driving said endless belt in said orbital direction and said translational direction,
magnetic commutation means for commutating acoustical function electrical signals from said transducer and energizing said light emitting diode, and
electrical cable means operatively associated with said drive means and said magnetic commutation means and being in communication with the exterior of said sealed housing for cooperation with external signal processing means and an electric power source means.

46. The ultrasonic scanner of claim 45 comprising
said drive means including a pair of rotatable pulleys disposed within said sealed housing, and
said endless belt secured over said pulleys for rotation therewith.

47. The ultrasonic scanner of claim 46 comprising
said magnetic commutation means including a commutation spring secured to said endless belt and electrically connecting said transducer and said light emitting diode in series.

48. The ultrasonic scanner of claim 47 including
said magnetic commutation means including for each said rotatable pulley a shaft upon which said pulley rotates, a pair of side members in contact with said shaft and an outer member all of which are magnetically conductive and cooperate to define a closed magnetic loop,
said magnetic commutation means including an electrical coil wound around each said magnetic loop,
each said coil being in electrical communication with said electrical cable means,
a first said magnetic loop and associated electrical coil for one said pulley operatively associated with other portions of said magnetic commutation means to commutate an acoustical function electrical signal from said transducer to said external signal processing means through said cable means, and
a second said magnetic loop and associated electrical coil for the other said pulley operatively associated with other portions of said magnetic commutation means in order that an electrical pulse within said cable means will through inductive action of said coil excite magnetic pulses in said magnetic loop which in turn will induce currents in said commutation spring to energize said light emitting diode.

49. The ultrasonic scanner of claim 48 including
each said magnetic commutation means including a Faraday shield surrounding said electrical coil.

50. The ultrasonic scanner of claim 48 including
said drive means including at least one electric motor disposed within said sealed housing, and
said electrical cable means energizing each said motor.

51. The ultrasonic scanner of claim 50 including
said sealed housing containing two said electrical motors,
said pulleys each serving as the armature of one said electric motor,
field windings secured to stators disposed on opposed sides of each said pulley, and
said electrical cable means energizing said field windings.

52. The ultrasonic scanner of claim 51 including
said pulleys containing squirrel cage induction motor armatures.

53. The ultrasonic scanner of claim 52 including
said stators having shading poles provided with shorting bars.

54. The ultrasonic scanner of claim 53 including
a first pulley shaft being externally threaded and being rotatably mounted, and
said first pulley having an internally threaded bore engaged with said first pulley shaft threads, whereby rotation of said first pulley to establish orbital motion of said endless belt will establish translational movement of said first pulley along said first pulley shaft.

55. The ultrasonic scanner of claim 54 including
a second pulley shaft being rotatably mounted for synchronous rotation with the second pulley.

56. The ultrasonic scanner of claim 55 including
said second pulley shaft and said second pulley being so configurated as to permit substantially free relative sliding movement of said second pulley along said second pulley shaft.

57. The ultrasonic scanner of claim 55 including
gear means connecting said first and second pulley shafts, whereby rotation of said second pulley shaft responsive to rotation of said second pulley will establish responsive rotation of said first pulley shaft.

58. The ultrasonic scanner of claim 57 including
said gear means including a first gear fixedly secured to said first pulley shaft and a second gear fixedly secured to said second pulley shaft, a third gear engaged with said first gear, a fourth gear engaged with said second gear, and a rotatably mounted shaft connecting said third and fourth gears, and
said gears being so configurated that said first gear rotates at a slower speed than said second pulley shaft responsive to rotation of said second pulley shaft.

59. The ultrasonic scanner of claim 48 including
each said pulley shaft being composed of ferrite.

60. The ultrasonic scanner of claim 46 including
said sealed housing having front and rear faces,
said rear face being optically transparent, and
said front face being acoustically transparent.

61. The ultrasonic scanner of claim 60 including
said light emitting diode having a convex converging lens that focuses the light output at about ⅛ to ¼ inch from the portion of said endless belt to which it is secured.

62. The ultrasonic scanner of claim 60 including
means for recording at least certain portions of the output of the light emitted by said light emitting diode.

63. The ultrasonic scanner of claim 62 including
said recording means including photographic record making means disposed exteriorly of said sealed scanner housing adjacent to said rear face.

64. The ultrasonic scanner of claim 63 including
said photographic record making means being a camera, and
said camera containing means for developing a picture of the photographically recorded images of said light emitting diode.

65. The ultrasonic scanner of claim 46 including
the front face of said housing being mechanically compliant.

66. The ultrasonic scanner of claim 65 including
said electric power source means disposed exteriorly of said housing in communication with said cable means, and
said external signal processing means disposed exteriorly of said housing in communication with said cable means.

67. The ultrasonic scanner of claim 66 including
an insonifying transducer disposed exteriorly of said sealed housing and adapted to emit an acoustical wave which will pass through the test specimen and be received by said endless belt mounted transducer.

68. The ultrasonic scanner of claim 46 including
a test specimen holder disposed exteriorly of said housing and in contact with the front face thereof composed of a material which will permit free transmission of dilatational ultrasonic waves, and
said test specimen holder having a portion which is generally complementary with respect to at least a portion of said test specimen, whereby interposing an acoustical coupling material between said test specimen and said test specimen holder will establish substantially continuous acoustical contact between said test specimen and said sealed housing.

69. The ultrasonic scanner of claim 68 including
said test specimen holder having an outwardly open recess serving as said test specimen complementary portion, and
vacuum pump means in communication with said holder recess, whereby said vacuum pump means will urge said test specimen into intimate acoustical coupling with said specimen holder.

70. The ultrasonic scanner of claim 69 including
said recess having the general configuration of a human female breast.

71. The ultrasonic scanner of claim 69 including
an insonifying transducer mounted on the side of said specimen holder opposite from the side on which said sealed housing is in contact with said test specimen holder.

72. The ultrasonic scanner of claim 68 including
said test specimen holder composed of a material selected from the group consisting of silicone rubber, vinylsols and plastisols.

73. The ultrasonic scanner of claim 68 including
said test specimen holder having a generally cylindrical exterior surface,
a coupling ring mounted for relative rotation about said specimen holder exterior surface,
said sealed housing having a curved front face secured in surface to surface contact with the exterior surface of said coupling ring, and
an insonifying transducer secured to said ring at a position generally diametrically opposed to said sealed housing and oriented for acoustical transmission in the direction of said sealed housing.

74. The ultrasonic scanner of claim 73 including
photographic record making means disposed on the opposite side of said endless belt from said sealed housing front face for recording at least a portion of the output of said light emitting diode.

75. The ultrasonic scanner of claim 74 including
said photographic record making means including a photographic plate holder of generally complementary curvature to said sealed housing curved front face.

76. The ultrasonic scanner of claim 51 including
means for reversing the direction of orbital movement of said endless belt to thereby effect a reversal in the direction of translation of said endless belt.

77. The ultrasonic scanner of claim 76 including
said reversing means including means for electrically reversing the direction of rotation of said pulleys.

78. The ultrasonic scanner of claim 77 including
alternating current power means operatively associated with said electrical cable means to excite said field winding of each said stator,
each said stator having first and second pole pieces depending from one side of the stator body and third and fourth pole pieces depending from a second side of the stator body,
said field winding disposed on said stator body,
tertiary coils wound around each of said first, second, third and fourth pole pieces,
said first pole tertiary coil electrically connected in series to said third pole tertiary coil, with first switch means in said circuit, and
said second pole tertiary coil electrically connected in series to said fourth pole tertiary coil, with second switch means in said circuit, whereby closing said first switch will result in rotation of said pulleys in a first direction and closing said second switch in lieu of said first switch will effect pulley rotation in the opposite direction.

79. The ultrasonic scanner of claim 48 including
a transducer electronics unit secured to said endless belt adjacent to said transducer,
said transducer electronics unit being electrically connected to said transducer and to said commutation spring,
said transducer electronics unit having means for energizing said transducer and receiving signals therefrom while resisting passage of high frequency radio-frequency current into said transducer,
a diode electronics unit secured to said endless belt adjacent to said light emitting diode,
said diode electronics unit being electrically connected to said light emitting diode and said commutation spring, and
said diode electronics unit having means for receipt of radio frequency current to energize said diode and resist passage of transducer signals into said diode.

80. The ultrasonic scanner of claim 45 including
said transducer and said light emitting diode each disposed on the exterior of said endless belt.

81. The ultrasonic scanner of claim 79 including
said transducer electronics unit having resonant circuit means in series with said commutation spring and a step down transformer in parallel relationship therewith, and
said diode electronics unit having resonant circuit means in series with said commutation spring, rectifier means receiving the output of said resonant circuit means, filter means receiving the output of said rectifier means and having an output operating said light emitting diode.

82. The ultrasonic scanner of claim 79 including
said transducer electronics unit and diode electronics unit being sufficiently elastic as to survive repeated cycles of belt travel over said pulleys without loss of electrical continuity.

83. The ultrasonic scanner of claim 82 including
the electronic components with said electronics units being connected to each other by resilient conductive members, and
said electronics units having resilient enclosures.

84. The ultrasonic scanner of claim 83 including
said resilient conductive members being corrugated springs.

85. The ultrasonic scanner of claim 67 including
said external signal processing means including pulse generator means, pulse amplifier means receiving input from said pulse generator means and delivering amplified pulses to said insonifying transducer, and
said external signal processing means also including
band reject filter means receiving acoustical imaging signals from one pulley commutation means through said cable means,
logarithmic receiver means obtaining a signal from said band reject filter means,
time delay generator means receiving input from said pulse generator means and delivering output signals to linear gate means which prevents passage of the logarithmic receiver means output signal until said time delay generator means permits, and
peak detector means receiving signals from said linear gate means having its output pass through modulator means through radio frequency power amplifier means to the other said pulley commutation means.

86. The ultrasonic scanner of claim 67 including
power means disposed exteriorly of said sealed housing for energizing said insonifying transducer, and
said external signal processing means including means for receiving the belt mounted transducer acoustical function electrical signals and creating responsive lighting of said light emitting diode in proportion to the logarithm of said acoustical function electrical signal.

87. The ultrasonic scanner of claim 85 including
said external signal processing means also including manually activated switch means for initiating operation of (1) scan time timer means which operate said scanner for a predetermined time period and (2) radio frequency carrier oscillator means which through said modulator means activates said light emitting diode and (3) audio frequency oscillator means which emits a signal through audio frequency amplifier means to activate said electric motors.

88. The ultrasonic scanner of claim 87 including
switch means for establishing translation of said endless belt in a first direction or in a second reverse direction.

89. The ultrasonic scanner of claim 45 including
said endless belt having an endless portion composed of an electrically conductive material,
said drive means including a number of replicating magnets defining a gap within which said conductive portion of said endless belt passes, and
alternating current means energizing said magnets, whereby said magnets will generate magnetic fields which establish orbital movement of said endless belt.

90. The ultrasonic scanner of claim 89 including
said transducer and said light emitting diodes secured to electrically nonconductive portions of said endless belt.

91. An integrated closed ultrasonic scanner comprising
a sealed housing,
an acoustically conductive liquid disposed within said sealed housing,
a rotatable drum disposed within said sealed housing,
at least two rows of transducers disposed on the circumference of said drum generally aligned with the central axis of said drum,
said rows of transducers spaced circumferentially from each other,
at least two rows of light emitting diodes disposed on the circumference of said drum generally aligned with the central axis of said drum,
drive means for rotating said drum,
commutation means for coordinating operation of an insonifying transducer disposed exteriorly of said sealed housing with the operation of internal signal handling means disposed within said sealed housing,
external signal processing means for energizing said insonifying transducer and coordinating operation of said commutation means with operation of said insonifying transducer,
an array of sound pipes having a generally curved surface adjacent to said drum and a generally flat surface on the other side thereof, whereby acoustical waves impinging upon said flat surface will be transmitted to said drum transducer through said curved surfaces, and a wall of said sealed housing adjacent to said sound pipe array flat surface being flexible.

92. The ultrasonic scanner of claim 91 including said rows of light emitting diodes spaced circumferentially from each other.

93. The ultrasonic scanner of claim 91 including said external signal processing means having means for energizing said drive means.

94. The ultrasonic scanner of claim 93 including said sealed housing having two chambers, and said rotatable drum disposed within a first said chamber.

95. The ultrasonic scanner of claim 94 including a flexible wall defining at least part of said second chamber.

96. The ultrasonic scanner of claim 95 including said commutation means being noncontacting magnetic means.

97. The ultrasonic scanner of claim 96 including said drum having at least four rows of said transducers and at least four rows of said light emitting diodes.

98. The ultrasonic scanner of claim 97 including said drum having the same number of rows of said transducers and said light emitting diodes, and each said row of transducers disposed closely adjacent to a row of said light emitting diodes.

99. The ultrasonic scanner of claim 98 including said rows of transducers being spaced substantially equally about the circumference of said drum.

100. The ultrasonic scanner of claim 99 including each said row of transducers having the same number of transducers and each like numbered transducer of each row being in substantially the same axial position on said drum, each said row of light emitting diodes having the same number of diodes and each like numbered light emitting diode of each row being in substantially the same axial position on said drum, and the number of said transducers in a row being equal to the number of said light emitting diodes in a row.

101. The ultrasonic scanner of claim 94 including said first chamber having a viewer window in the wall opposite the wall having the said sound pipe array.

102. The ultrasonic scanner of claim 101 including said viewer window being a magnifying lens.

103. The ultrasonic scanner of claim 102 including said viewer window being hooded and said lens having means for correcting for cylindrical distortion of said image.

104. The ultrasonic scanner of claim 101 including a magnifying lens disposed adjacent to said viewer window.

105. The ultrasonic scanner of claim 91 including said drive means disposed within said housing, and said drive means including an alternating current motor having a squirrel cage rotor secured within or formed integrally with said rotatable drum and stators disposed adjacent said rotor energized by field windings.

106. The ultrasonic scanner of claim 105 including internal signal handling means disposed within said drum for energizing predetermined light emitting diodes responsive to receipt of acoustical waves by predetermined transducers.

107. The ultrasonic scanner of claim 106 including secondary coils secured to the interior of said rotor for energizing said internal signal handling means.

108. The ultrasonic scanner of claim 106 including said commutation means being antenna means connecting said internal signal handling means with the exterior of said sealed housing.

109. The ultrasonic scanner of claim 108 including switch means for operating said scanner, and handle means secured to the exterior of said scanner.

110. The ultrasonic scanner of claim 108 including said internal signal handling means having means for energizing all light emitting diodes at the same axial position on said drum when a transducer at the same axial position on said drum receives an acoustical wave from an insonifying transducer through a specimen with the intensity of light emitting diode illumination being related to the intensity of the acoustical wave received by said insonifying transducer.

111. The ultrasonic scanner of claim 107 including said internal signal handling means including a. rectifier bridge means electrically connected to said secondary coils for receiving voltage therefrom and emitting direct current voltage, and b. for said adjacent rows of said adjacent transducers and light emitting diodes (1) electrolytic capacitor means for smoothing said direct current voltage received from said rectifier bridge and (2) voltage regulator means regulating said voltage received from said capacitor means and (3) conductor means electrically connecting said voltage regulator means with said transducers and said light emitting diodes through internal circuit means.

112. The ultrasonic scanner of claim 111 including all said transducers in the same axial position on said drum being electrically connected in parallel relationship, commutation antenna means for receiving time reference signals from said external signal processing means for coordinating transfer of signals from said transducers to said light emitting diodes, and said internal circuit means including as to each set of said transducers in the same axial position a. radio frequency amplifier means for receiving the combined signal from said set of transducers, b. gate means for permitting passage of the output of said radio frequency amplifier solely when said commutation antenna means is receiving a predetermined signal, c. diode means for rectifying the output of said gate means, d. peak detector means receiving the output of said diode means, and e. light emitting diode driver means for energizing all light emitting diodes in the same axial position as said transducer set responsive to receipt of the output of said peak detector means, whereby each receipt of an insonifying transducer signal by a said transducer will result in responsive illumination of all said light emitting diodes at the same axial position as said transducer.

113. The ultrasonic scanner of claim 108 including said external signal processing means having means for energizing said insonifying transducer and controlling through said commutation antenna means the period within which the internal signal handling means will process acoustical signals received by said rows of transducers.

114. The ultrasonic scanner of claim 113 including said external signal processing means including
   a. pulse generator means energizing said insonifying transducer through pulse amplifier means,
   b. adjustable time delay generator means receiving signals from said pulse generator means and initiating output from gate pulse generator means,
   c. modulator means receiving the output from said gate pulse generator means and radio frequency generator means, and
   d. radio frequency power amplifier means receiving the output of said modulator and emitting output to said commutation antenna means.

115. The ultrasonic scanner of claim 113 including said external signal processing means including switch means for initiating operation of audio frequency oscillator means which in turn drives audio frequency power amplifier means, electrical conductor means connecting said audio frequency power amplifier means with said stator field windings.

116. The ultrasonic scanner of claim 107 including said external signal processing means including rechargeable battery means.

117. An integrated closed ultrasonic scanner comprising
   a sealed housing,
   an acoustically conductive liquid disposed within said sealed housing,
   a rotatable drum disposed within said sealed housing,
   a front wall of said drum oriented generally transversely to the longitudinal axis of said drum and rotatable therewith,
   a substantially linear array of receiving transducers secured to said front wall,
   a rear wall of said drum oriented generally transversely to the longitudinal axis of said drum and rotatable therewith,
   a substantially linear array of light emitting diodes secured to said rear wall,
   drive means for rotating said drum,
   internal signal handling means disposed within said sealed housing for energizing predetermined light emitting diodes responsive to acoustical signals received by predetermined receiving transducers,
   external signal processing means disposed exteriorly of said sealed housing for energizing said drive means and cooperating with said internal signal handling means, and
   commutation means connecting said internal signal handling means with said external signal processing means.

118. The ultrasonic scanner of claim 117 including a portion of said sealed housing adjacent said drum front wall being defined by a flexible wall, whereby intimate acoustical contact between a test specimen of irregular configuration and said flexible wall may be effected.

119. The ultrasonic scanner of claim 117 including a transparent viewing window secured to said sealed housing rearwardly of said rear wall.

120. The ultrasonic scanner of claim 119 including a light shielding hood projecting rearwardly from said viewing window.

121. The ultrasonic scanner of claim 119 including said viewing window including a magnifying lens.

122. The ultrasonic scanner of claim 119 including a magnifying lens disposed adjacent to said viewing window.

123. The ultrasonic scanner of claim 117 including said drive means including an electric motor disposed within said housing, and
said motor having a rotor which is secured to or formed as a unit with said drum.

124. The ultrasonic scanner of claim 123 including said electric motor having an annular split-phase alternating current induction motor stator disposed within said housing in surrounding relationship with respect to said rotor.

125. The ultrasonic scanner of claim 124 including said stator having running windings and starting windings,
said external signal processing means including alternating current supply means for energizing said stator windings,
electric switch means interposed between said current supply means and said stator windings, and
capacitor means electrically interposed between said switch means and said starting windings.

126. The ultrasonic scanner of claim 117 including said commutation means being magnetic.

127. The ultrasonic scanner of claim 123 including said rotor being a squirrel cage rotor, and
secondary coils secured to the interior of said rotor for energizing said internal signal handling means.

128. The ultrasonic scanner of claim 126 including said commutation means being noncontacting antenna means.

129. The ultrasonic scanner of claim 128 including said internal signal handling means having means to energize a predetermined light emitting diode responsive to receipt by a predetermined receiving transducer of an acoustical wave generated by an externally disposed insonifying transducer and passed through a test specimen with the intensity of the illumination of said light emitting diode being related to the intensity of the acoustical wave received by said receiving transducer.

130. The ultrasonic scanner of claim 117 including said sealed housing being generally cylindrical and having an axial length of about 5 to 12 inches and a diameter of about 5 to 15 inches.

131. The ultrasonic scanner of claim 117 including said front wall having an elongated slot to which is secured a metal sheet-like element on which said array of transducers is secured.

132. The ultrasonic scanner of claim 130 including the number of receiving transducers being equal to the number of light emitting diodes, and
said scanner having about 25 to 75 transducers.

133. The ultrasonic scanner of claim 129 including said internal signal handling means including fullwave rectifier bridge means for receiving output from from said secondary coils and emitting direct current voltage, capacitor means smoothing the output of said rectifier bridge means and voltage regulator means regulating said voltage received from said capacitor means.

134. The ultrasonic scanner of claim 133 including said internal signal handling means including circuit means receiving said direct current voltage from said voltage regulator and converting the acoustical signal received by said receiving transducer into a responsively energized light emitting diode.

135. The ultrasonic scanner of claim 134 including
said commutation antenna means adapted to receive time reference signals from said exterior signal processing means for coordinating transfer of signals from said transducer to said light emitting diodes, and said circuit means including for each said receiving transducer
  a. radio frequency amplifier means for receiving the output signal from said receiving transducer,
  b. gate means for permitting passage of the output of said radio frequency amplifier solely when said commutation antenna means is receiving a predetermined signal,
  c. diode means for rectifying the output of said gate means,
  d. peak detector means receiving the output of said diode means, and
  e. light emitting diode driver means for energizing a predetermined light emitting diode responsive to receipt of the output of said peak detector means.

136. The ultrasonic scanner of claim 135 including
said external signal processing means having means for energizing an insonifying transducer and controlling through said commutation antenna means the period within which the internal signal handling means will process acoustical signals received by said array of transducers.

137. The ultrasonic scanner of claim 136 including
said external signal processing means including
  a. pulse generator means energizing said insonifying transducer through pulse amplifier means,
  b. adjustable time delay generator means receiving signals from said pulse generator means and initiating output from gate pulse generator means,
  c. modulator means receiving the output from said gate pulse generator means and radio frequency generator means, and
  d. radio frequency power amplifier means receiving the output of said modulator means and emitting output to said commutation antenna means.

138. The ultrasonic scanner of claim 137 including
said external signal processing means including switch means for initiating operation of audio frequency oscillator means which in turn drives audio frequency power amplifier means, and electrical conductor means connecting said audio frequency power amplifier means with said stator field windings.

139. The ultrasonic scanner of claim 118 including
said housing divided into two chambers by an acoustically transparent rigid wall disposed between said drum and said flexible wall.

140. The ultrasonic scanner of claim 129 including
said external signal processing means including rechargeable battery means powering said scanner.

* * * * *